(12) United States Patent
Jessell et al.

(10) Patent No.: US 7,312,081 B2
(45) Date of Patent: Dec. 25, 2007

(54) GENETIC DEMONSTRATION OF REQUIREMENT FOR NKX6.1, NKX2.2 AND NKX6.2 IN VENTRAL NEURON GENERATION

(75) Inventors: Thomas M. Jessell, Bronx, NY (US); James Briscoe, London (GB); Johan Ericson, Hasselby (SE); John L. R. Rubenstein, San Francisco, CA (US); Maike Sander, Hamburg (DE)

(73) Assignees: The Trustees of Columbia University in the City of New York, New York, NY (US); The Regents of the University of California, Alameda, CA (US)

( * ) Notice: Subject to any disclaimer, the term of this patent is extended or adjusted under 35 U.S.C. 154(b) by 500 days.

(21) Appl. No.: 10/362,437

(22) PCT Filed: Aug. 31, 2001

(86) PCT No.: PCT/US01/27256

§ 371 (c)(1),
(2), (4) Date: Aug. 1, 2003

(87) PCT Pub. No.: WO02/18545

PCT Pub. Date: Mar. 7, 2002

(65) Prior Publication Data

US 2004/0053210 A1   Mar. 18, 2004

Related U.S. Application Data

(63) Continuation-in-part of application No. 09/654,462, filed on Sep. 1, 2000, which is a continuation-in-part of application No. 09/569,259, filed on May 11, 2000.

(51) Int. Cl.
*C12N 5/00*    (2006.01)
*C12N 5/02*    (2006.01)

(52) U.S. Cl. .................. 435/377; 435/325; 435/375

(58) Field of Classification Search ............... 424/93.1, 424/93.2, 93.21; 514/44
See application file for complete search history.

(56) References Cited

U.S. PATENT DOCUMENTS

| | | | |
|---|---|---|---|
| 6,235,885 B1 | 5/2001 | Jessell et al. |
| 6,387,656 B1 | 5/2002 | Jessell et al. |
| 6,566,092 B1 | 5/2003 | Jessell et al. |
| 2002/0197678 A1 | 12/2002 | Jessell et al. |
| 2003/0104374 A1 | 6/2003 | Jessell et al. |
| 2004/0005602 A1 | 1/2004 | Jessell et al. |

FOREIGN PATENT DOCUMENTS

| WO | WO95/23223 A1 | 8/1995 |
|---|---|---|
| WO | WO99/00516 A2 | 1/1999 |
| WO | WO 00/09676 A2 | 2/2000 |
| WO | WO 00/18884 A1 | 4/2000 |
| WO | WO 01/84933 A1 | 11/2001 |
| WO | WO 02/18545 A1 | 3/2002 |

OTHER PUBLICATIONS

Inoue et al. (1997) Isolation, characterization, and chromosomal mapping of the human Nkx6.1 gene (NKX6A), a new pancreatic islet homeobox gene. Genomics 40: 367-370.*
Komuro et al. (1993) Gtx: a novel murine homeobox-containing gene, expressed specifically in glial cells of the brain and germ cells of testis, has a transcriptional repressor activity in vitro for a serum-inducible promoter. EMBO Journal 12(4): 1387-1401.*
McKusick, V.A. Online Mendelian Inheritance in Man, OMIM (TM). Johns Hopkins University, Baltimore, MD. MIM No. 605955: Last edited: Aug. 11, 2005. World Wide Web URL: http://www.ncbi.nlm.nih.gov/omim/.*
U.S. Appl. No. 09/569,259, filed May 11, 2000 on behalf of Thomas M. Jessell et al.
U.S. Appl. No. 09/654,462, filed Sep. 1, 2000 on behalf of Thomas M. Jessell et al.
International Search Report issued on Aug. 29, 2001 in connection with PCT International Application No. PCT/US01/15290, filed May 11, 2001, International Publication No. WO01/84933 A1, published Nov. 15, 2001, on behalf of The Trustees of Columbia University in the City of New York.
International Search Report issued on Jan. 15, 2002 in connection with PCT International Application No. PCT/US01/27256, filed Aug. 31, 2001, International Publication No. WO02/18545 A1, published Mar. 7, 2002, on behalf of The Trustees of Columbia University in the City of New York.
Supplementary Partial European Search Report issued on Aug. 19, 2004 in connection with European Patent Application No. 01968382, filed Aug. 31, 2001 on behalf of the Trustees of Columbia University in the City of New York.
Supplementary Partial European Search Report issued on Dec. 12, 2004 in connection with European Patent Application No. 01968382, filed Aug. 31, 2001 on behalf of the Trustees of Columbia University in the City of New York.
Cai, J. et al. (2001) "Mice lacking the *Nkx6.2* (*Gtx*) homeodomain transcription factor develop and reproduce normally," *Molecular and Cellular Biology* 21: 4399-4403.

(Continued)

*Primary Examiner*—Anne-Marie Falk
(74) *Attorney, Agent, or Firm*—John P. White; Cooper & Dunham LLP

(57) ABSTRACT

This invention provides a method of converting a stem cell into a ventral neuron which comprises introducing into the stem cell a nucleic acid which expresses homeodomain transcription factor Nkx6.1 or Nkx6.2 protein in the stem cell so as to thereby convert the stem cell into the ventral neuron. Provided are methods of diagnosing a motor neuron degenerative disease in a subject. Also provides is a method of treating neuronal degeneration in a subject which comprises implanting in diseased neural tissue of the subject a neural stem cell which is capable of expressing homeodomain Nkx6.1 or Nkx6.2 protein under conditions such that the stem cell is converted into a motor neuron after implantation, thereby treating neuronal degeneration in the subject.

4 Claims, 22 Drawing Sheets

OTHER PUBLICATIONS

Campbell, G. et al., (1999) "Transducing the Dpp Morphogen Gradient in the Wing of Drosophila: Regulation of Dpp Targets by brinker", *Cell* 96: 553-562.

Chiang, C. et al., (1996) "Cyclopia and Defective Axial Patterning in Mice Lacking Sonic Hedgehog Gene Function", *Nature* 383: 407-413.

Dasen, J.S. et al., (1999) "Combinatorial Codes in Signaling and Synergy: Lessons From Pituitary Development", *Curr. Opin. Genet. & Dev.* 9: 566-574.

Ding, Q. et al., (1998) "Diminished Sonic Hedgehog Signaling and Lack of Floor Plate Differentiation in Gli2 Mutant Mice", *Development* 125: 2533-2543.

Doetsch, F. et al., (1999) "Subventricular Zone Astrocytes Are Neural Stem Cells in the Adult Mammalian Brain", *Cell* 97: 703-716.

Erskine, L. et al. (1998) "Progenitor Dispersal and the Origin of Early Neuronal Phenotypes in the Chick Embryo Spinal Cord" *Dev. Biol.* 199: 26-41.

Funayama, N. et al. (1999) "Coelom Formation: Binary Decision of the Lateral Plate Mesoderm is Controlled by the Ectoderm" *Development* 126: 4129-4138.

Gage, F.H. (2000) "Mammalian Neural Stem Cells", *Science* 287:1433-1438.

Huang, A.M. et al. (1997) "An Anteroposterior Dorsal Gradient in the Drosophila Embryo", *Genes & Dev.* 11: 1963-1973.

Ingham, P.W. (1998) "Transducing Hedgehog: The Story So Far" *EMBO J.* 17: 3505-3511.

Jazwinska, A. et al. (1999) "The Drosophila Gene brinker Reveals a Novel Mechanism of Dpp Target Gene Regulation", *Cell* 96: 563-573.

Johansson, C.B. et al. (1999) "Identification of a Neural Stem Cell in the Adult Mammalian Central Nervous System", *Cell* 96: 25-34.

Kraut, R. et al. (1991) "Spatial Regulation of the Gap Gene giant During Drosophila Development", *Development* 111: 601-609.

Krishnan, V. et al. (1997) "Mediation of Sonic Hedgehog-Induced Expression of COUP-TFII by a Protein Phosphatase", *Science*, 278: 1947-1950.

Lawrence, P.A. et al. (1996) "Morphogens, Compartments, and Pattern: Lessons from Drosophila?", *Cell* 85: 951-961.

Lewis, K.E. et al. (1999) "Expression of ptc and gli Genes in talpid³ Suggest Bifurcation in Shh Pathway" *Development* 126: 2397-2407.

Mansouri, A. et al. (1998) "Pax3 and Pax7 are Expressed in Commissural Neurons and Restrict Ventral Neuronal Identity in the Spinal Cord", *Mech. Dev.* 78: 171-178.

Marti, E. et al. (1995) "Distribution of Sonic Hedgehog Peptides in the Developing Chick and Mouse Embryo", *Development* 121: 2537-2547.

Matise, M.P. et al. (1998) "Gli2 is Required for Induction of Floor Plate and Adjacent Cells, But Not Most Ventral Neurons in the Mouse Central Nervous System", *Development* 125: 2759-2770.

McDowell, N. et al. (1999) "Activin as a Morphogen in Xenopus Mesoderm Induction", *Semin. Cell & Dev. Biol.* 10: 311-317.

Minami, M. et al. (1999) "Brinker is a Target of Dpp in Drosophila that Negatively Regulates Dpp-dependent Genes", *Nature* 398: 242-246.

Papin, C. et al. (2000) "Gradual Refinement of Activin-Induced Thresholds Requires Protein Synthesis" *Dev. Biol.* 217: 166-172.

Pierani, A. et al. (1999) "A Sonic Hedgehog-Independent Retinoid-Activated Pathway of Neurogenesis in the Ventral Spinal Cord", *Cell* 97: 903-915.

Roelink, H. et al. (1995) "Floor Plate and Motor Neuron Induction by Different Concentrations of the Amino-Terminal Cleavage Product of Sonic Hedgehog Autoproteolysis", *Cell* 81: 445-455.

Rowitch, D.H. et al. (1999) "Sonic hedgehog Regulates Proliferation and Inhibits Differentiation of CNS Precursor Cells", *J. Neurosci.* 19: 8954-8965.

Ruiz i Altaba, A. (1999) "Gli Proteins and Hedgehog Signaling: Development and Cancer", *Trends Genet.* 15: 418-425.

Sharma, K. et al. (1998) "LIM Homeodomain Factors Lhx3 and Lhx4 Assign Subtype Identities for Motor Neurons", *Cell* 95: 817-828.

Smith, J.C. (1995) "Mesoderm-Inducing Factors and Mesodermal Patterning", *Curr. Opin. Cell Biol.* 7: 856-861.

Tanabe, Y. et al. (1998) "Specification of Motor Neuron Identity by the MNR2 Homeodomain Protein", *Cell* 95: 67-80.

Wu, X. et al. (1998) "Two Distinct Mechanisms for Differential Positioning of Gene Expression Borders Involving the Drosophila Gap Protein Giant", *Development* 125: 3765-3774.

Horner et al. (2000) "Regenerating the Damaged Central Nervous System", 407: 963-970.

Jackowski (1995) "Neural Injury Repair" pp. 303-317.

Hamburger, V. et al. (1951) "A Series Of Normal Stages In The Development Of The Chick Embryo", *J. Morphol.* 88: 49-92.

Langman, J. et al. (1966) "Behavior of Neuroepithelial Cells During Closure Of The Neural Tube", *J. Comp. Neur.* 127: 399-411.

Leber, S.M. et al. (1995) "Migratory Paths Of Neurons And Glia In The Embryonic Chick Spinal Cord", *J. Neurosci.* 15: 1236-1248.

Muramatsu, T. et al. (1997) "Comparison Of Three Nonviral Transfection Methods For Foreign Gene Expression In Early Chicken Embryons In Ovo", *Biochem. Biophys. Res. Commun.* 230: 376-380.

Sander, M. et al. (2000) "Ventral Neural Patterning By Nkx Homeobox Genes: Nkx6.1 Controls Somatic Motor Neuron And Ventral Interneuron Fates", *Genes & Development* 14(17): 2134-2139.

Struhl, G. et al. (1992) "Control of Drosophila Body Pattern By The hunchback Morphogen Gradient", *Cell* 69: 237-249.

Yamada, T. et al. (1993) "Control of Cell Pattern In The Neural Tube: Motor Neuron Induction By Diffusible Factors From Notochord And Floor Plate", *Cell* 73: 673-686.

Basler, K. et al. (1993) "Control of cell pattern in the neural tube: Regulation of cell differentiation by dorsalin-1, a novel TGF beta family member", *Cell* 73: 687-702.

Briscoe, J., and Ericson, J. (2001) "Specification of neuronal fates in the ventral neural tube", *Curr. Opin Neurobiol.* 11: 43-49.

Briscoe, J. et al. (2001) "A hedgehog-insensitive form of patched provides evidence for direct long-range patterning activity of Sonic hedgehog in the neural tube", *Molecular Cell* 7: 1279-1291.

Cai, J. et al. (1999) "Expression and regulation of the chicken Nkx-6.2 homeobox gene suggest its possible involvement in the ventral neural patterning and cell fate specification", *Dev. Dyn.* 216: 459-468.

Davis, C.A. et al. (1991) "Examining pattern formation in mouse, chicken and frog embyros with an En-specific antiserum", *Development* 111: 287-298.

Eberhard, D. et al. (2000) "Transcriptional repression by Pax5 (BSAP) through interaction with corepressors of the Groucho family" *EMBO J.* 19: 2292-2303.

Hoshiyama, D. et al. (1998) "Sponge Pax cDNA related to Pax-2/5/8 and ancient gene duplications in the Pax family", *J. Mol. Evol.* 47: 640-648.

Jörgensen, M.C. et al. (1999) "Cloning and DNA-binding properties of the rat pancreatic beta-cell-specific factor Nkx6.1", *FEBS Lett.* 461: 287-294.

Kraut, R. and Levine, M. (1991) "Mutually repressive interactions between the gap genes giant and Kruppel define middle body regions of the Drosophila embryo" *Development* 111: 611-621.

Komuro, I. et al. (1993) "Gtx: a novel murine homeobox-containing gene, expressed specifically in glial cells of the brain and germ cells of testis, has a transcriptional repressor activity in vitro for a serum-inducible promoter" *EMBO* 12: 1387-1401.

Lee, S. et al. (2001) "Cloning, expression and chromosomal location of NKX6B to 10q26, a region frequently deleted in brain tumors", *Mammalian Genome* 12: 157-162.

Mombaerts, P. et al. (1996) "Visualizing an olfactory sensory map", *Cell* 87: 675-686.

Moran-Rivard, L. et al. (2001) "Evxl is a postmitotic determinant of V0 interneuron identity in the spinal cord", *Neuron* 29: 385-399.

Muhr, J. et al. (2001) "Groucho-mediated transcriptional repression establishes progenitor cell pattern and neuronal fate in the ventral neural tube", *Cell* 104: 861-873.

Novitch, B. et al. (2001) "Coordinate regulation of motor neuron subtype identity and pan-neural properties by the bHLH repressor Olig2", *Neuron* 31: 773-789.

Nutt, S.L. et al. (1999) "Commitment to the B-lymphoid lineage depends on the transcription factor Pax5", *Nature* 401: 556-562.

Pabst, O. et al. (2000) "NKX2 gene expression in neuroectoderm but not in mesendodermally derived structures depends on sonic hedgehog in mouse embryos", *Dev. Genes. Evol.* 210: 47-50.

Peters, T. et al. (2000) "Organization of mouse Iroquois homeobox genes in two clusters suggests a conserved regulation and function in vertebrate development", *Genome Res.* 10: 1453-62.

Pierani, A. et al. (2001) "Control of interneuron fate in the developing spinal cord by the progenitor homeodomain protein Dbx1" *Neuron* 29: 367-384.

Rolink, A.G. et al. (1999) "Long-term in vivo reconstitution of T-cell development by Pax5-deficient B-cell progenitors", *Nature* 401: 603-606.

Schaeren-Wiemers, N. and Gerfin-Moser, A. (1993) "A single protocol to detect transcripts of various types and expression levels in neural tissue and cultured cells: in situ hybridization using digoxigenin-labeld cRNA probes", *Histochemistry* 100: 431-440.

Shoji, H. et al. (1996) "Regionalized expression of the Dbx family homeobox genes in the embryonic CNS of the mouse", *Mech. Dev.* 56: 25-39.

Stanojevic, D., Small, S. and Levine, M. (1991) "Regulation of a segmentation stripe by overlapping activators and repressors in the Drosophila embryo", *Science* 254: 1385-1387.

Tanaka, M., Yamasaki, N., Izumo, S. (2000) "Phenotypic characterization of the murine Nkx2.6 homeobox gene by gene targeting", *Mol. Cell. Biol.* 20: 2874-2879.

Toresson, H., Potter, S.S. and Campbell, K. (2000) "Genetic control of dorsal-ventral identity in the telencephalon: Opposing roles for Pax6 and Gsh2", *Development* 127: 4361-4371.

Wang, C.C. et al. (2000) "Conserved linkage of NK-2 homeobox gene pairs Nkx2-2/2-4 and NK-2-1/2-9 in mammals", *Mamm. Genome* 11: 466-468.

Yun, K., Potter, S. and Rubenstein, J.L. (2001) "Gsh2 and Pax6 play complementary roles in dorsoventral patterning of the mammalian telencephalon", *Development* 128: 193-205.

Anderson, S.A. et al. (1997) "Interneuron Migration from Basal Forebrain to Neocortex: Dependence on DLx Genes", *Science* 278:474-476.

Arber, S. et al. (1999) "Requirement for the Homeobox Gene Hb9 in the Consolidation of Motor Neuron Identity", *Neuron* 23:659-674.

Briscoe, J. et al. (2000) "A Homeodomain Protein Code Specifies Progenitor Cell Identity and Neuronal Fate in the Ventral Neural Tube", *Cell* 101:435-445.

Burrill, J.D. et al. (1997) "PAX2 is expressed in multiple spinal cord interneurons, including a population on EN1+ interneurons that require PAX6 for their development", *Development* 124:4493-4503.

Chu, H. et al. (1998) "Formation and specification of ventral neuroblasts is controlled by vnd in Drosophila neurogenesis", *Genes & Dev.* 12:3613-3624.

Goulding, M.D. et al. (1991) "Pax-3, a novel murine DNA binding protein expressed during early neurogenesis", *EMBO J.* 10:1135-47.

Hammerschmidt, M. et al. (1997) "The world according to hedgehog", *Trends Genet* 13:14-21.

Hebrok, M. et al. (1998) "Notochord repression of endodermal Sonic hedgehog permits pancreas development", *Genes & Dev.* 12: 1705-1713.

Inoue, H. et al. (1997) "Isolation, characterization, and chromosomal mapping of the human Nkx6.1 gene (NKX6A), a new pancreatic islet homeobox gene", *Genomics* 40:367-370.

Matise, M.P. et al. (1997) "Expression Patterns of Development Control Genes in Normal and Engrailed-1 Mutant Mouse Spinal Cord Reveal Early Diversity in Developing Interneurons", *J. Neurosci.* 17:7805-7816.

McDonald, J. A. et al. (1998) "Dorsoventral patterning in the Drosophila central nervous system: the vnd homeobox gene specifies ventral column identity", *Genes & Dev.* 12:3603-3612.

Pattyn, A. et al., (1997) "Expression and interactions of the two closely related homeobox genes Phox2a and Phox2b during neurogensis", *Development* 124:4065-4075.

Rubenstein, J.L. et al. (1998) "Patterning of the embryonic forebrain", *Curr. Opin. Neurobiol.* 8:18-26.

Rubenstein, J.L. et al. (1998) "Regionalization of the Prosencephalic Neural Plate", *Annu. Rev. Neurosci.* 21:445-477.

Sussel, L. et al. (1999) "Loss of Nkx2.1 homeobox gene function results in a ventral to dorsal molecular respecification within the basal telencephalon: evidence for a transformation of the pallidum into the striatum", *Development* 126:3359-3370.

Tanabe, Y. et al. (1996) "Diversity and Pattern in the Developing Spinal Cord", *Science* 274:1115-23.

Thaler, J. et al. (1999) "Active Suppression of Interneuron Programs within Developing Motor Neurons Revealed by Analysis of Homeodomain Factor HB9", *Neuron* 23:675-687.

Tsuchida, T. et al. (1994) "Topographic Organization of Embryonic Motor Neurons Defined by Expression of LIM Homeobox Genes", *Cell* 79:957-970.

Valerius, M. T. et al. (1995) "Gsh-1: A Novel Murine Homeobox Gene Expressed in the Central Nervous System", *Dev. Dyn.* 203:337-51.

Weiss, J. B. et al. (1998) "Dorsoventral pattering in the Drosophila central nervous system: the intermediate neuroblasts defective homeobox gene specifies intermediate column identity", *Genes & Dev.* 12:3591-3602.

Mirmira et al. (2000) "Beta-Cell Differentiation Factor Nkx6.1 Contains Distinct DNA Binding Interference And Transcriptional Repression Domains", *J. Biol. Chem.* 275(19):14743-14751.

Oster et al. (1998) "Homeobox Gene Product Nkx 6.1 Immunoreactivity In Nuclei Of Endocrine Cells Of Rat And Mouse Stomach", *J. Histochem. And Cytochem.* 46(6):717-721.

Schwitzgebel et al. (2000) "Expression Of Neurogenin3 Reveals An Islet Cell Precursor Population In The Pancreas", *Genes & Development* 127:3533-3542.

Friedman, T. (Jun. 1997) "Overcoming The Obstacles To Gene Therapy", *Scientific American*, pp. 96-101.

Orkin, S.H and Motulsky, A.G. (1995) "Report And Recommendations Of The Panel To Assess The NIH Investment In Research On Gene Therapy".

Verma, I.M. and Somia, N. (1997) "Gene Therapy—Promises, Problems and Prospects", Nature 389: 239-242.

"Stem Cells: Scientific Progress and Future Research Directions" (Jun. 2001) Department of Health and Human Services, pp. 1-9.

Briscoe, J. et al. (1999) "Homeobox Gene Nkx2.2 and specification of Neuronal Identity by Graded Sonic Hedgehog Signalling", *Nature* 398:622-627.

Ericson, J. et al. (1996) "Two Critical Periods of Sonic Hedgehog Signaling Required for the Specification of Motor Neuron Identity", *Cell* 87:661-673.

Ericson, J. et al. (1997) "Pax6 Controls Progenitor Cell Identity and Neuronal Fate in Response to Graded Shh Signaling", *Cell* 90:169-180.

Ericson, J. et al. (1997) "Graded Sonic Hedgehog Signaling and the Specification of Cell Fate in the Ventral Neural Tube", *Cold Spring Harb. Symp. Quant. Biol.* 62:451-466.

Lumsden, A. et al. (1996) "Patterning the Vertebrate Neuraxis", *Science* 274:1109-1115.

Pabst, O. et al. (1998) "Nkx-9 is a Novel Homeobox Transcription Factor Which Demarcates Ventral Domains in the Developing Mouse CNS", *Mech. Dev.* 73:85-93.

Qiu, M. et al. (1998) "Control of Anteroposterior and Dorsoventral Domains of Nkx-6.1 Gene Expression Relative to Other Nkx Genes During Vertebrate CNS Development", *Mech. Develop.* 72:77-88; and.

Palmer, T.D. et al. (1999) "Fibroblast growth factor-2 activates a latent neurogenic program in neural stem cells from diverse regions of the adult CNS," *The Journal of Neuroscience* 19: 8487-8497.

* cited by examiner

Figure 6

```
  1 mlavgamegt rqsafllssp plaalhsmae mktplypaay pplpagppss sssssssssp
 61 spplgthnpg glkppatggl sslgsppqql saatphginn ilsrpsmpva sgaalpsasp
121 sgssssssss asassasaaa aaaaaaaaaa sspagllagl prfsslsppp pppglyfsps
181 aaavaavgry pkplaelpgr tpifwpgvmq sppwrdarla ctphqgsill dkdgkrkhtr
241 ptfsgqqifa lektfeqtky lagperarla yslgmtesqv kvwfqnrrtk wrkkhaaema
301 takkkqdset erlkgasene eedddynkpl dpnsddekit qllkkhksss ggggglllha
361 sepesss
```

Figure 7

```
  1 cgtgggatgt tagcggtggg ggcaatggag ggcacccggc agagcgcatt cctgctcagc
 61 agccctcccc tggccgccct gcacagcatg gccgagatga agacccccgct gtaccctgcc
121 gcgtatcccc cgctgcctgc cggccccccc tcctcctcgt cctcgtcgtc gtcctcctcg
181 tcgccctccc cgcctctggg cacccacaac ccaggcggcc tgaagccccc ggccacgggg
241 gggctctcat ccctcggcag cccccccgcag cagctctcgg ccgccacccc acacggcatc
301 aacaatatcc tgagccggcc ctccatgccc gtggcctcgg gggccgccct gccctccgcc
361 tcgccctccg gttcctcctc ctcctcttcc tcgtccgcct ctgcctcctc cgcctctgcc
421 gccgccgcgg ctgctgccgc ggccgcagcc gccgcctcat ccccggcggg gctgctggcc
481 ggactgccac gctttagcag cctgagcccg ccgccgccgc cgcccgggct ctacttcagc
541 cccagcgccg cggccgtggc cgccgtgggc cggtacccca agccgctggc tgagctgcct
601 ggccggacgc ccatcttctg gcccggagtg atgcagagcc cgccctggag ggacgcacgc
661 ctggcctgta cccctcgtga gt
```

Figure 8

```
  1 tcacagatca aggatccatt ttgttggaca aagacgggaa gagaaaacac acgagaccca
 61 cttttrccgg acagcagatc ttcgccctgg agaagacttt cgaacaaaca aaatacttgg
121 cggggcccga gagggctcgt ttggcctatt cgttggggat gacagagagt caggtcaagg
181 tgagt
```

Figure 9

```
  1 cctcaggtct ggttccagaa ccgccggacc aagtggagga agaagcacgc tgccgagatg
 61 gccacggcca agaagaagca ggactcggag acagagcgcc tcaaggggc  ctcggagaac
121 gaggaagagg acgacgacta caataagcct ctggatccca actcggacga cgagaaaatc
181 acgcagctgt tgaagaagca caagtccagc agcggcggcg gcggcggcct cctactgcac
241 gcgtccgagc cggagagctc atcctgaacg ccg
```

FIGURE 18

```
   1 aagcttggcc tgtctgcacc cagcaccccc gggtgtcctc ctgggagggc tggaccttgt
  61 ctcttggcag caccgtgggg ccctcagagc cctccatcta gttccgggca gggcagggcc
 121 ccttcccaac accatcggct gcctctggtc actcccaccc aggggcacag ggaatctctg
 181 aacacccctt ccctggggag caggaagact tgaaacctcc ttggccaggc agggcggtt
 241 tctactgtgc ccaccagacc cccaggctaa gccagcaggg agactggaag gcccagtgtc
 301 cagcccctgc cctgcctcag ggtggctgct cgccctctcc cctcccaccc cacctggaca
 361 gcctcggtcc tcagggcgct gtanggagtg aggcacctgt gggatggagc ctcagcgtgg
 421 gtgcgagaca tgctgcaggg cccaggtgcg gagccgcgtg tgaacgggca ggcggcccgc
 481 agcgtctccg tcacgagaag gaagtggatg ctcgtgacaa cagaagaact cggttcgggg
 541 gaagaacttg gttgttcagg ggaagaactc ggaccattct ctgtgtgtct ctctctgtgc
 601 tttcggtaag tgctgctccs ttggctgctg catttacaag tgactttaa agaacagaag
 661 ctggaaggaa acctggggct caggattcag ggaggggcc ctgcaaggtg ggaggggccc
 721 ggccagggcc caggctgtgc aaggaacttc aggcccagtg aagctagagg gtccacaaag
 781 gctgggcagg ggccaccctg aagggggtgct cagagagttc aggcaagctc tccctccct
 841 gccatccagg tcctcccagc ccctgccctc ttagccccc ttcagggcct cctcaacccg
 901 cgggtgttcc agattccaca gcctggccca tatcttccag ggagagtgtt cgggtgccg
 961 ggcacccact gtggccccac cccagcttca tcaaagcctc cctccctgtc ctgggccaht
1021 cggcctgggg aaaagcggca ccctctcccc agagcctgat cctccamttc atgtggacct
1081 gtaggtgttg gcaagtgggc aagaggccgc catagcctgg gaagaggggg cacctggacg
1141 ccccacctac agctgggtac cccaaaagct gccgggctct acctggacac cctccagctc
1201 aggagatggg gtggggttga gtttggtcta aacagcaaga cctcaggctc agctgggaaa
1261 tgccacggcg ccaggcccca catccagcat gtcctgtggc tcaggcttcc tggaggcacc
1321 tccacagtac ctgctcctcc cggtgggaag tcaggtgcgc ggtcctccct ctccaacccg
1381 caccgggct ctgaaaattg ctctgaggcc tgcagctgtc acacttgcgt tcattcaccc
1441 acccagcagc atgaattcag tcctggaggc gcccagagga cagagccct gcatccatcc
1501 atgtcctgag caaggtggcg aggaggcgga catcagacac atccactaat gccttcggca
1561 ggggccagt gccaagaggg gcagccgtgc tgagtgggag tgtgggggct gcaccagacc
1621 gggtggccag ggaggcgtcc ctcaagctga gaccgcgtgg aggaggtgag ccctgtgaag
1681 tgggggggca gagtggccgg ggtgggtgag cctgggggcc acgaggggac cagtggaggg
1741 cctggcaggc atgggatggc attaggtgga aacaggtgga ggtggagact cgcgatctct
1801 gaaataaagc cgctgctagc aggctggtgc tcagcaggca gtgctggaag tgtgagaagg
1861 ggccaggcta ggccaggatg aggagtggag cctcctctgc ccacctaggg gcgtcaactc
1921 ccacccctgg gcggtcccca ccccagcct cagcgctcat ggcctttcag acccggctgg
1981 gtccatgagc ccagtgggac gccggggctg cctggctggg atctgcgcct gcctcccagc
2041 ccttccccgc tgccctggca gggctgcccc cagagggcac gggagatggg gttggggtct
2101 gtcctgcgtg ggaggcaggg cccccttgag ttgtgttgtg gggtggggtt ttctctagcc
2161 cccccttcccc ttccagcaat tccagagcgt cctggtgggc tcctctgttt ccaagcaaca
2221 gaaggcaccc cgcctgggcc cgggctcctg ggggtcctgg taaccccacg ccgctgcttc
2281 cgtgggtggg gcccacagag gggtcccttg agtcatcttg ggccttttt ggttctttgg
2341 tcatgaggac cccagggagg ccccgtctgt gtctggaatg cctggtgcgg ttaccttgtc
2401 aagcctggag aggccgggaa tgcgctcact tcgggaaaaa agacaatgca gggcctttgc
2461 cgggaactgc taggagaccc ccggcctggg ggcgcggtca gggcgggcag cttggcaact
2521 cgcctagggc tgcgcgggac aagtcacctc agtgataaat cagagtttgt gaactctatg
2581 gcctgggcgg ccgaaggcga acgcaggctc cttccctctg tggagttccc ccgtcgcccc
2641 tcagccccca gcgcggggac accgggcct argccggctc tccttccggg ccgacacccc
2701 cgccgtcctc cccgtcgccc gctccctgc agacgccgcg ggggtgcgg gggagcgcgt
2761 ttgctgctct gacccgcccg cgcccgggcc ggagcccgct gcgttcacgg tgcaccccc
2821 ggacagcccg ggcgcggtaa gagcccaca aatacaggct gaacgagtaa aacaaacttg
2881 aatggcctct gccaaaaccc gcgctctcgg ttttccarcg cggagcgttc gcgccgatgc
2941 cggcagcctt cctcgcggga catctgctcg cgggccagga ggtggcatcg cggacctctc
3001 caggcagcgg ggccgccggg cggcggagcc caggcaaaga catcgcggtc kgaggcgctc
3061 ggaccttccc gggaggaggg ggagttgcct cggtggtttc cgagaggcg gcaccggggg
3121 acgcaggaga aaaggtgcgg gcggggccg gagaggggac gggcccgga gtgggcgccg
3181 ggaagcgtag gaggtgaagc caccggaccc acgcgcagct cggcgaggag gagggcggga
3241 aagccgtgg ggcgcaggcc ggggagccgg gtaggacgcg gcacctgcgg agcgcgccaa
3301 gacttccacg gcttacaaga acgtgggaga gggacccccc cttacccggc tcctctgcgc
```

FIGURE 18(CONT.)

```
3361 ccccaactca ccctggcccc tcatcccgcg ccctgagcc ctggagagcc gcgcgctccg
3421 cagccagtga cacggccagcc ccacccgcga ccccacgcgt tccctcggca gcccagggag
3481 gaccgggggg cgcagacaga cccaggggtt atcggccgc agcgcagcgc ctccaggtcc
3541 atgttcctc agccataaaa cagcgctagc gacgcccct gccccgcccc tccaggctgt
3601 gagaagagcc agagcctgtc ccgagcgcgg cttcctcccg ccgttccgcc cgcgcgcgcc
3661 tcctgggcct cagttcggga gacccgcacc cctcccggcc cgcccagggt ctgcccggcc
3721 gcgcagagtg ggggatccca gggcgacagc agccccgcc cccaactccc cctgcccgcc
3781 cccccggcc ccgcagttcc cgcgtctcag ctcagagccc gagccttggg cgcgggcgcc
3841 gtcgccttgg ggtgctggga ggggcccgaa cccgacccgg gagggcccctt cctcgtgtct
3901 cctccgaggg agcggggcgc aggacaggcc ggggcgggtc tcggggccgg acgggcgctg
3961 ggggttcccg ggccaggctc cgcgggggcg gatcaccggt ggggcggccg cgcccaatcg
4021 aatcccaatc ccagtcgaat cgagtgcgga gtcgacgggg gaagcgaacc ccccgtgaac
4081 gcgggctgc acctcagtgg agccggaaag ccgccggggc agccccgagc gcgcacacac
4141 ccggcggccg caccactgcc ccggagtttg gccgcaggtg gcttttccaa gccgccatcc
4201 aggagcggcc gacggcgcca agtcccgcc tcgacctgca caaacgaaa acggacgctg
4261 gaggggggcg aggggcgga cgtgagaccc cggccccgaa ccccgggcgc cgccttcctc
4321 cgcggcacag gcccgagaga ggccacgcag cggcgttccc tgcgcacaga ctcgggctcc
4381 ccacgagccg tgggccacag ccacagccgc cccgtgtccc taaatcaata cgagacgtca
4441 ccacagacgt cggagcgttt gctcgcggcc gccgtgcgcg gggctcggag tcatctcacc
4501 gcccggtctg cgggatggat gagcgagcgg ctcccggtgc cgtggggggcg gggggacac
4561 cggcccccg cgcgcgtcta aggccgcgtt tctgccgctg cgcccccagc ccgcacccac
4621 gttcggcccc tggacagggc ttccgcgctg aggccgtcct ggtctctgtt ctccccggccg
4681 gggattcgcg agaggcggcc cgtgggcgaa gtcgtgggcc caggtcacat cctgggggac
4741 ccccagcggg agacctggag gccgatgacg gggaagtgcc gagccgcgcg tgtggtcccg
4801 ggacccgcct ccccgccccg ctcccgcctg cctcactcct ccaccgcgcc ggccgcgtgt
4861 cggcgaaacc agaggcagct ccgtgcgagc ctcgcccggc cgtgaggccc gtggattccg
4921 tggactcgag gcccgcgtcc tccgccctcc tgtggccccg acctgccgg agcgcgttcc
4981 ccgccggcgt ccgctgccgc tcacacccac cccagccacg ggcggccgag cagtcgcgac
5041 tgggacgcgg gccgggactc ttccccgagt ggggcgctcc gagcgcgcgg gcgggtcctc
5101 aaatctgcat tctttccgtt aataaaatac gttctcgtat tttttcctga tttcgcatga
5161 aaacctttgc ctaactacac tcccatccaa gcgggattta tttcgtcccc ggggagataa
5221 atcggggcga atttacagcc cgggaggcac ctgccgcgct aatgggccct tcatggagtg
5281 cgcggccggc ggggcgcgc gggcggggg ggggcgccgg ccaatggccg gaccgcgggg
5341 tccgcagcca atcagcgcgc gcgccgcgcc ccggcggagc cccgttatc agcgcgtccg
5401 tcccgcgcgg cgccgctccg accggccccg ggagccgccg ccgccgccgc ccgcccgccc
5461 gccccgcgcc ggagccgccc gcccgcccc cgcgcccgcc gcccccgcgct gcagccgacg
5521 cccgcccggg ccgcgcgcaa acttcccggg ccggcgggca ggggcgggcgg cggcggggcc
5581 cggatgggag cccgggccgg cggcggcggc gcccatggac actaaccgcc cgggcgcgtt
5641 cgtgctgagc agtgccccgc tggccgcgct gcacaacatg gccgagatga agacgtcgct
5701 gttcccctac gcgctgcagg gtccggccgg cttcaaggcg cccgcgctgg ggggcctggg
5761 cgcgcagctc ccgctcggga ccccgcacgg catcagcgac atcctgggcc ggcccgtggg
5821 cgcggcgggc ggggcctcc tgggggggct gccccggctc aacgggctcg cgtcgtccgc
5881 cggcgtttac ttcgggcccg cggccgctgt ggcgcgcggc tacccaagc ccctggccga
5941 gctgccgggg cgcccgccca tcttctggcc cggcgtggtg cagggcgcgc cctggaggga
6001 cccgcgtctg gctggcccgg gtgagtggcc cgcgcgggg gtgcgggcg ggtgggcgcg
6061 gaggggggacc ccgccggccg ctgacctccc tcccttcccc tcccttgcag ccccggccgg
6121 cggcgtcctg gacaaggacg ggaagaagaa gcactcgcgc ccgaccttct cgggccagca
6181 gatcttcgcg ctggagaaaa ccttcgagca gaccaagtac ctggcggggcc cggagcgcgc
6241 gcgtctcgcc tactcgctgg gcatgaccga gagccaggtg aaggtgagcg cggcgggct
6301 cgggagagca gagccgggg cccgcgtcct gcgaacggcc ccagcgccag ccccgggccc
6361 cgcggccgcc tgaccgcccc gtccactccc aggtctggtt ccagaaccgc cggaccaagt
6421 ggcgcaagcg gcacgcggcg gagatggcgt cggccaagaa gaagcaggac tcggacgccg
6481 agaagctgaa ggtgggcggc tcggacgcgg aggacgacga cgaatacaac cggcccctgg
6541 accccaactc ggacgacgag aagatcacgc ggctgctcaa gaagcacaaa ccctcgaact
6601 tggcgctggt cagcccgtgc ggcggcggcg cggggacgc cttgtgagga cccgcgggt
6661 ggggcgaat ctattttgc agaatccggg ggcggccccg ggtgggcgcg agtcgctttg
6721 tatcatcaat aaattattta acgggtcccc gtcggagccg tcgctccgga gcctgcgccg
6781 cgtgtttctt ccgtctcgaa cccggagcga gcggcccct ccccggcccc ggcttcgccc
6841 ctgcgcccgc ctcgggtcct ccgggttccc ggtgcggasg ctgcgggccc cggcaggcg
6901 cgaggaggcg gcgaaggcgc agggaagggg cccgccccgc gggaaggaac cgcagcgaca
6961 gccgccagga gcccgggtcg gmgccggga cggagcagca ggtacggccc ggcccgcctc
7021 gcctcggggc ggattcggac gcgcttgggg gttccgcgaaa gggcggtga gccgcgtacc
7081 cgcctcgagt cccgccggga ggttttttctt cttccgtttt cccgcttttg ggccacgtac
7141 tcgttgccac cggcacccgg ttcccgctcg gcgagggct tcgctctgat tatttccaaa
7201 gtccctctgc gcatcagcgg atcccatagg cccgccctgg gctcagccgg tggaaccggg
7261 tctgatccgc tgcacggagg cccttcggtc accatcccgc cagatcttcc cgcggtggaa
7321 agcagtttct tccgaactag gaccgcaaag agaaatccga aataattccg cccgcggagc
7381 ggcggggcct cccgtgggtc acgcggggtc agggagccgg aggcccctg ggcaaggccc
7441 gcaagcgccc agccgggggg ctcgggggac ccgtcttcct gccctgaaat gccgccagct
```

FIGURE 18(CONT.)

```
 7501 ccgccggggc tgtgactgcg gctgacaaaa cccctccarc ctcccgcarc ctctgttggc
 7561 cggggctgcc matccgctgc awcttaatgg gcgtggctgt tgagttttaa ttttaaaaa
 7621 ttaaatgtaa ataatgatat cactgcggtg gtacgatttc tcttggcatt tgcggaagcg
 7681 ttaaagggaa atagaaaggg cttaaactcg gcgcgttttg ttttaggctc ttagcagcct
 7741 tctttacaag gaagcaactc gaagggcaga agcaacgctt ttctgtgggg agccctctc
 7801 agctcagagc agaggggctt cttaaagttt tgaggaaggc aaagcgttga tataatcccg
 7861 ttttaaaatg ttgagggata aatcctttat tacagtagaa agtccaaaag gctgtgtttc
 7921 tcctctcaat gaacggctta gtgttttgtg acagcgtgtg atacagtgaa attccaggat
 7981 ttctaatgag cttgatctca aataaaggct atacangagg ccgctcccct gagttagcat
 8041 ttcaaaggtg gcaggagaag ggaaggaag aaaaagcaac acggggacta ttttcaccac
 8101 ggtcaatttt attgcttagg aaccagaccg gtcacttcca aaggccctc agaacgacca
 8161 acagctgaaa cccgcggggc ggactccgtg ttgaaccgcg gacagcggca accacagcag
 8221 cgacacggac ctgtgcttcc accaagaaca gattccgcag cggacagcag tcacttgcag
 8281 tggtagtatt tatcccacac aaacacccag ctaatgcctt cacccccggtc ccaggaactc
 8341 tgtagtgttc taaagtaaaa atcaataaaa acatacattt gtgtttcatc aacagactct
 8401 ctaatcacct tctaatgctg tacttactgc tataggagaa aaatatttgc aacaaggtta
 8461 tgacatgggt tgtctgtagc ggagcaatga ggaaatgtac agttttgttt ctctttaata
 8521 tttttatata cagcccatgt taaaagcagt ttctattgga agcaaactag gctatttcta
 8581 tttctcccat gatattattg ttgtaacgta ggatacttgg caccataaaa cagtaacaaa
 8641 agacagacaa acggtttaca aaattcttaa aaggtacacc caggctagct ataaacttca
 8701 cattcagttc ttaatattac acagaagaac ggcatgggag taacggcccg ctggtgcaga
 8761 cgtgctgtgg ggccgatttt acccacgatg gcgaggccat gtgtgttttt tacgaatttg
 8821 tgtgttgatg gacacacagc tgagctccta gactccaatg ccgcctgctg atgggactct
 8881 cctgtgcgtt cactactggaa agtatattta gcataagttt tggtaagatt tataaattat
 8941 ttttaaaaag tatatattta tatatattta tatatatata aaaatggaaa gcagctgcag
 9001 tgtgattcaa aaaccatgtg acacggcgca gagtcagtgc cgcggaagga gcatcggcag
 9061 agacagaccc ccttgccatg ctcagggcca cgctgccggc cggcagaggg agtgcccgtc
 9121 tcggcttccc cagcccctgg acacacctcc acctggcaga ggggtccct ggacacagtg
 9181 gggggtctct gtgctgaaga agcccctcca ctggcaatca ttaaaaactg aaaactgtga
 9241 agtctacggt acagaccctc tttgctgtct attagagttt tgacaacagg actgtgactt
 9301 atttaaaaaa aaaaaaaaac caatatttct acttaatgtc acatagacag acgagacagt
 9361 gaggtatgtg gggctgctcc ggaatggtcc ggaggctgaa gcgaagtgtg gggctggccg
 9421 tctagcaggt ggcgcttggg cgggttctcg atgcagcttt caagagtgcg tattcggtcc
 9481 acggctacag ggaggctcac gaagtgtcct ctcgtggcgc tggcatctct tcccaccacg
 9541 tcactgcacg acacaacact tgtgcacatg ggcatgaggt ttacctgccc cgggcatgat
 9601 tcggaaggcc aggaacacgg gcttgtggtc tcccatgcag acgttgggcc caatgtggtc
 9661 ataggtgaca accttctcct cgctctccga ccgcagcacc agctccttgg cagacgggga
 9721 catgaggatg cggtcacacc aggctgggca ccgggtgttc atgtactgct caccctggcg
 9781 ggcgtcctca ctgtacgggt agctgggagg gaacgagatg tccagttcat acagtctgtc
 9841 cttaaagaca gacaactcct tgtcaaactc caagagcgcg gtgccgttgt tgtctcggaa
 9901 aacctcctgg ttgaagtagt cgaagagttt cttttctaac tggagcataa ccttccggtc
 9961 gttgtccgac tcacgaaata tgagcttcac cacttcattg gtgtcggcgg cccggaccgt
10021 ctgcatcggt ggttttgctg agagcgtctc cacgacagac ttggaatcca gccggaagtt
10081 gaaatcacca aatacaaagt aggaaaccct ctcgaatcgc tgatcaatga ttctgtccag
10141 cacgtagccc agtgccttgt gccggattcc cgagtacacg gaagggcttg tttcccaggc
10201 gaccagattg gaagcatcat ggaaaagatg gatattcacc aagtcaaagg cacagtctgc
10261 aatcaccacc tcgtccggat gaagcctttt cttgaccatt tgcactcggg gaagtagtct
10321 gcgaaacttc tccttctcca gcatgggcgt gctctctaag gtatccgagt agatctcttt
10381 gccagcgacc tttctatact tcttagcttt aaagtcaaac tggtagatgt tttttaagga
10441 ctcatgaaga aaataaaagc tt
```

FIGURE 19

```
  1 mdtnrpgafv lssaplaalh nmaemktslf pyalggpagf kapalgggiga qlplgtphgi
 61 sdilgrpvga agglligglp rlnglassag vyfgpaaava rgypkplael pgrppifwpg
121 vvqgapwrdp rlagpapagg vldkdgkkkh srptfsgqqi falektfeqt kylagperar
181 layslgmtes qvkvwfqnrr tkwrkrhaae masakkkgds daeklkvggs daedddeynr
241 pldpnsddek itrllkkhkp snlalvspcg ggagdal
```

FIGURE 20

```
               ⇩            ⇩⇩          ⇩⇩                                                                                                                          ⇩
mNK6.3         MESNLQGTFLLNNTQLAQFSEMKAPMCQYSVQNSFY*****************************************KLSPPGLG****
rNkx6.1        MLAVGAMEGPRQSAFLLSSPPLAALHSM*AEMKTPLYPAAYPELPTGPPSSSSSSSSPSPPLGAHRPGGLKPPAAGGLSS
mNkx6.2        MDANRPGAFVLSSAPLAALHNM*AEMKTSLFPYALQ*****************************G****PAGFKTPA
cNkx6.2        MDANRQSAFVLGSTPLAALHNM*AEMKSSLFPYALQ*********************************N****PSSFKAPA

⇩⇩⇩⇩⇩  ⇩⇩  ⇩⇩⇩ ⇩⇩
mNK6.3         *****PQLAAGTPHGITDILSRPVATPNSSLLSGYPHVAGFGGLSSQ************************************
rNkx6.1        LGSPPQQLSAATPHGINDILSRPSMPVASGAALPSASPSGSSSSSSASATSASALAAAAAAAAAASSPAGLLAGLPRFS
mNkx6.2        LGSLGAQLPLGTPHGISDILGRPVGAAGGGLIGSLPRLNGLASSA*******************************
cNkx6.2        LGGLNTQLPLGTPHGISDILGRPVGARGNLLGGLPRINGLAASA***********************************

⇩  ⇩                                      ⇩  ⇩⇩               ⇩ ⇩  ⇩ ⇩⇩⇩⇩   ⇩⇩⇩    ⇩
mNK6.3         ******GVYYGPQVGSFSKAGNEYPTRTRNC*******WADTGQ**DWRGSARPCS*NTPDPLSDTTHKKKHTRPTFTG
rNkx6.1        SLSPPPPPGLYFSPS*AAAVAVGRYPKPLAEL*GRTPIFWPGVMQSPPWRDARLACTPHQGSILLDKDGKRKHTRPTFSG
mNkx6.2        *******GVYFGPAAAV**A*RGYPKPLAELPGRPPIFWPGVVQGSPWRDPRLAGSAQAG*GVLDKDGKKKHSRPTFSG
cNkx6.2        *******GVYFGPAAVS****RYPKPLAELPGRPPIFWEGVVQGSPWRDPRLTCPAQTG*MVLDKDGKKKHSRPTFSG

⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩⇩   ⇩ ⇩                        ⇩⇩⇩          ⇩⇩
mNK6.3         HQIFALEKTFEQTKYLAGPERARLAYSLGMTESQVKVWFQNRRTKWRKKSALEPSSTPRAPGGASGDRAASEN*EDDE*YN
rNkx6.1        QQIFALEKTEEQTKYLAGPERARLAYSLGMTESQVKVWFQNRRTKWRKKHAAEMATAKKKQDSETERLKGTSENEEDDDYN
mNkx6.2        QQIFALEKTFEQTKYLAGPERARLAYSLGMTESQVKVWFQNRRTKWRKRKHAAEMASAKKKQDSDAEKLKVGGSDAEDDEYN
cNkx6.2        QQIFALEKTEEQTKYLAGPERARLAYSLGMTESQVKVWFQNRRTKWRKRHAAEMASAKKKHDSETEKLKESSDN*EDDDEYN

⇩⇩⇩⇩ ⇩⇩ ⇩⇩⇩  ⇩⇩ ⇩⇩      ⇩
mNK6.3         KPLDPDSDNEKIRLLLRKHRAAFSVLSLGAHSV
rNkx6.1        KPLDPNSDDEKITQLLKKHKSSGGSLLIHASEAEGSS
mNkx6.2        RPLDPNSDDEKITRLLKKHKPSNLALVSPCGGSAGDAL
cNkx6.2        KPLDPNSDDEKITRLLKKHKSTNLALVSPCSTSSDTL
``` yellow = EnH1 domain including the TN peptide
green = HD

SEQUENCE LISTING

```
<160> NUMBER OF SEQ ID NOS: 10

<210> SEQ ID NO 1
<211> LENGTH: 367
<212> TYPE: PRT
<213> ORGANISM: Human

<400> SEQUENCE: 1

Met Leu Ala Val Gly Ala Met Glu Gly Thr Arg Gln Ser Ala Phe Leu
1               5                   10                  15

Leu Ser Ser Pro Pro Leu Ala Ala Leu His Ser Met Ala Glu Met Lys
                20                  25                  30

Thr Pro Leu Tyr Pro Ala Ala Tyr Pro Pro Leu Pro Ala Gly Pro Pro
            35                  40                  45

Ser Ser Ser Ser Ser Ser Ser Ser Ser Ser Pro Ser Pro Pro Leu
    50                  55                  60

Gly Thr His Asn Pro Gly Gly Leu Lys Pro Pro Ala Thr Gly Gly Leu
65                  70                  75                  80

Ser Ser Leu Gly Ser Pro Pro Gln Gln Leu Ser Ala Ala Thr Pro His
                85                  90                  95

Gly Ile Asn Asn Ile Leu Ser Arg Pro Ser Met Pro Val Ala Ser Gly
            100                 105                 110

Ala Ala Leu Pro Ser Ala Ser Pro Ser Gly Ser Ser Ser Ser Ser Ser
        115                 120                 125

Ser Ser Ala Ser Ala Ser Ser Ala Ser Ala Ala Ala Ala Ala Ala
    130                 135                 140

Ala Ala Ala Ala Ala Ala Ser Ser Pro Ala Gly Leu Leu Ala Gly Leu
145                 150                 155                 160
```

```
Pro Arg Phe Ser Ser Leu Ser Pro Pro Pro Pro Gly Leu Tyr
            165                 170                 175

Phe Ser Pro Ser Ala Ala Ala Val Ala Ala Val Gly Arg Tyr Pro Lys
                180                 185                 190

Pro Leu Ala Glu Leu Pro Gly Arg Thr Pro Ile Phe Trp Pro Gly Val
            195                 200                 205

Met Gln Ser Pro Pro Trp Arg Asp Ala Arg Leu Ala Cys Thr Pro His
210                 215                 220

Gln Gly Ser Ile Leu Leu Asp Lys Asp Gly Lys Arg Lys His Thr Arg
225                 230                 235                 240

Pro Thr Phe Ser Gly Gln Gln Ile Phe Ala Leu Glu Lys Thr Phe Glu
                245                 250                 255

Gln Thr Lys Tyr Leu Ala Gly Pro Glu Arg Ala Arg Leu Ala Tyr Ser
            260                 265                 270

Leu Gly Met Thr Glu Ser Gln Val Lys Val Trp Phe Gln Asn Arg Arg
            275                 280                 285

Thr Lys Trp Arg Lys Lys His Ala Ala Glu Met Ala Thr Ala Lys Lys
            290                 295                 300

Lys Gln Asp Ser Glu Thr Glu Arg Leu Lys Gly Ala Ser Glu Asn Glu
305                 310                 315                 320

Glu Glu Asp Asp Asp Tyr Asn Lys Pro Leu Asp Pro Asn Ser Asp Asp
                325                 330                 335

Glu Lys Ile Thr Gln Leu Leu Lys Lys His Lys Ser Ser Ser Gly Gly
            340                 345                 350

Gly Gly Gly Leu Leu Leu His Ala Ser Glu Pro Glu Ser Ser Ser
            355                 360                 365

<210> SEQ ID NO 2
<211> LENGTH: 682
<212> TYPE: DNA
<213> ORGANISM: Human

<400> SEQUENCE: 2
cgtgggatgt tagcggtggg ggcaatggag ggcacccggc agagcgcatt cctgctcagc      60
agccctcccc tggccgccct gcacagcatg gccgagatga agaccccgct gtaccctgcc     120
gcgtatcccc cgctgcctgc cggccccccc tcctcctcgt cctcgtcgtc gtcctcctcg     180
tcgccctccc cgcctctggg cacccacaac ccaggcggcc tgaagccccc ggccacgggg     240
gggctctcat ccctcggcag ccccccgcag cagctctcgg ccgccacccc acacggcatc     300
aacaatatcc tgagccggcc ctccatgccc gtggcctcgg gggccgccct gccctccgcc     360
tcgccctccg gttcctcctc ctcctcttcc tcgtccgcct ctgcctcctc cgcctctgcc     420
gccgccgcgg ctgctgccgc ggccgcagcc gccgcctcat cccggcgggg gctgctggcc     480
ggactgccac gctttagcag cctgagcccg ccgccgccgc cgcccgggct ctacttcagc     540
cccagcgccg cggccgtggc cgccgtgggc cggtacccca agccgctggc tgagctgcct     600
ggccggacgc ccatcttctg gcccggagtg atgcagagcc cgccctggag ggacgcacgc     660
ctggcctgta ccctcgtga gt                                                682

<210> SEQ ID NO 3
<211> LENGTH: 185
<212> TYPE: DNA
<213> ORGANISM: Human

<400> SEQUENCE: 3
```

-continued

```
tcacagatca aggatccatt ttgttggaca aagacgggaa gagaaaacac acgagaccca      60 cttttttccgg acagcagatc ttcgccctgg agaagacttt cgaacaaaca aaatacttgg    120
cggggcccga gagggctcgt ttggcctatt cgttggggat gacagagagt caggtcaagg    180
tgagt                                                                 185
```

<210> SEQ ID NO 4
<211> LENGTH: 273
<212> TYPE: DNA
<213> ORGANISM: Human

<400> SEQUENCE: 4

```
cctcaggtct ggttccagaa ccgccggacc aagtggagga agaagcacgc tgccgagatg      60
gccacggcca agaagaagca ggactcggag acagagcgcc tcaagggggc ctcggagaac    120
gaggaagagg acgacgacta caataagcct ctggatccca actcggacga cgagaaaatc    180
acgcagctgt tgaagaagca caagtccagc agcggcggcg cggcggcct cctactgcac    240 gcgtccgagc cggagagctc atcctgaacg ccg                                  273
```

<210> SEQ ID NO 5
<211> LENGTH: 10462
<212> TYPE: DNA
<213> ORGANISM: Human
<220> FEATURE:
<221> NAME/KEY: misc_feature
<222> LOCATION: (384)..(384)
<223> OTHER INFORMATION: Where "N" = A, G, C or T
<220> FEATURE:
<221> NAME/KEY: misc_feature
<222> LOCATION: (620)..(620)
<223> OTHER INFORMATION: Where "N" = G or C
<220> FEATURE:
<221> NAME/KEY: misc_feature
<222> LOCATION: (1019)..(1019)
<223> OTHER INFORMATION: Where "N" = A, C or T
<220> FEATURE:
<221> NAME/KEY: misc_feature
<222> LOCATION: (1067)..(1067)
<223> OTHER INFORMATION: Where "N" = A or C
<220> FEATURE:
<221> NAME/KEY: misc_feature
<222> LOCATION: (2672)..(2672)
<223> OTHER INFORMATION: Where "N" = G or A
<220> FEATURE:
<221> NAME/KEY: misc_feature
<222> LOCATION: (2918)..(2918)
<223> OTHER INFORMATION: Where "N" = G or A
<220> FEATURE:
<221> NAME/KEY: misc_feature
<222> LOCATION: (3051)..(3051)
<223> OTHER INFORMATION: Where "N" = G or T
<220> FEATURE:
<221> NAME/KEY: misc_feature
<222> LOCATION: (6879)..(6879)
<223> OTHER INFORMATION: Where "N" = G or C
<220> FEATURE:
<221> NAME/KEY: misc_feature
<222> LOCATION: (6978)..(6978)
<223> OTHER INFORMATION: Where "N" = G or A
<220> FEATURE:
<221> NAME/KEY: misc_feature
<222> LOCATION: (6982)..(6982)
<223> OTHER INFORMATION: Where "N" = A or C
<220> FEATURE:
<221> NAME/KEY: misc_feature
<222> LOCATION: (7539)..(7539)
<223> OTHER INFORMATION: Where "N" = G or A
<220> FEATURE:
<221> NAME/KEY: misc_feature
<222> LOCATION: (7549)..(7549)
<223> OTHER INFORMATION: Where "N" = G or A
<220> FEATURE:
<221> NAME/KEY: misc_feature
<222> LOCATION: (7571)..(7571)
<223> OTHER INFORMATION: Where "N" = A or C
<220> FEATURE:
<221> NAME/KEY: misc_feature
<222> LOCATION: (7582)..(7582)
<223> OTHER INFORMATION: Where "N" = A or T
<220> FEATURE:
<221> NAME/KEY: misc_feature
<222> LOCATION: (8016)..(8016)
<223> OTHER INFORMATION: Where "N" = A, G, C or T

<400> SEQUENCE: 5

```
aagcttggcc tgtctgcacc cagcaccccc gggtgtcctc ctgggagggc tggaccttgt    60
ctcttggcag caccgtgggg ccctcagagc cctccatcta gttccgggca gggcagggcc   120
ccttcccaac accatcggct gcctctggtc actcccaccc aggggcacag ggaatctctg   180
aacacccctt ccctggggag caggaagact tgaaacctcc ttggccaggc cagggcggtt   240
tctactgtgc ccaccagacc cccaggctaa gccagcaggg agactggaag gcccagtgtc   300
cagcccctgc cctgcctcag ggtggctgct cgccctctcc cctcccaccc cacctggaca   360
gcctcggtcc tcagggcgct gtanggagtg aggcacctgt gggatggagc ctcagcgtgg   420
gtgggagaga tgctgcaggg cccaggtgcg gagccgcgtg tgaacgggca ggcggccccgc   480
agcgtctccg tcacgagaag gaagtggatg ctcgtgacaa cagaagaact cggttcgggg   540
gaagaacttg gttgttcagg ggaagaactc ggaccattct ctgtgtgtct ctctctgtgc   600
tttcggtaag tgctgctccn ttggctgctg catttacaag tgactttttaa agaacagaag   660
ctggaaggaa acctgggct caggattcag ggagggggcc ctgcaaggtg gaggggccc    720
ggccagggcc caggctgtgc aaggaacttc aggcccagtg aagctagagg gtccacaaag   780
gctgggcagg ggccaccctg aagggggtgct cagagagttc aggcaagctc tccctcccct   840
gccatccagg tcctcccagc ccctgccctc ttagccccc ttcagggcct cctcaacccg    900
cgggtgttcc agattccaca gcctggccca tatcttccag ggagagtgtt cgggtgcccg   960
ggcacccact gtggccccac cccagcttca tcaaagcctc cctccctgtc ctgggccant  1020
cggcctgggg aaaagcggca ccctctcccc agagcctgat cctccanttc atgtggacct  1080
gtaggtgttg gcaagtgggc aagaggccgc catagcctgg gaagaggggg cacctggacg  1140
ccccacctac agctgggtac cccaaaagct gccgggctct acctggacac cctccagctc  1200
aggagatggg gtggggttga gtttggtcta aacagcaaga cctcaggctc agctgggaaa  1260
tgccacggcg ccaggcccca catccagcat gtcctgtggc tcaggttcc tggaggcacc   1320
tccacagtac ctgctcctcc cggtgggaag tcaggtgcgc ggtcctccct ctccaacccg  1380
caccgggct ctgaaaattg ctctgaggcc tgcagctgtc acacttgcgt tcattcaccc   1440
acccagcagc atgaattcag tcctggaggc gcccagagga cagagcccct gcatccatcc  1500
atgtcctgag caaggtggcg aggaggcgga catcagacac atccactaat gccttcggca  1560
gggggccagt gccaagaggg gcagccgtgc tgagtgggag tgtggggct gcaccagacc   1620
gggtggccag ggaggcgtcc ctcaagctga ccgcgtgg aggaggtgag ccctgtgaag    1680
tggggggggca gagtggccgg ggtgggtgag cctgggggcc acgaggggac cagtggaggg  1740
cctggcaggc atgggatggc attaggtgga acaggtgga ggtggagact cgcgatctct   1800
gaaataaagc cgctgctagc aggctggtgc tcagcaggca gtgctggaag tgtgagaagg  1860
ggccaggcta ggccaggatg aggagtggag cctcctctgc ccacctaggg gcgtcaactc  1920
```

-continued

```
ccacccctgg gcggtcccca ccccagccct cagcgctcat ggcctttcag acccggctgg    1980
gtccatgagc ccagtgggac gccggggctg cctggctggg atctgcgcct gcctcccagc    2040
cctttcccgc tgccctggca gggctgcccc cagagggcac gggagatggg gttggggtct    2100
gtcctgcgtg ggaggcaggg ccccttcgag ttgtgttgtg gggtggggtt ttctctagcc    2160
ccccttcccc ttccagcaat tccagagcgt cctggtgggc tcctctgttt ccaagcaaca    2220
gaaggcaccc cgcctgggcc cgggctcctg ggggtcctgg taaccccacg ccgctgcttc    2280
cgtgggtggg gcccacagag gggtcccttg agtcatcttg ggcctttttt ggttctttgg    2340
tcatgaggac cccaggagg ccccgtctgt gtctggaatg cctggtgcgg ttaccttgtc    2400
aagcctggag aggccgggaa tgcgctcact tcgggaaaaa agacaatgca gggcctttgc    2460
cgggaactgc taggagaccc ccggcctggg ggcgcggtca gggcgggcag cttggcaact    2520
cgcctagggc tgcgcgggac aagtcacctc agtgataaat cagagtttgt gaactctatg    2580
gcctgggcgg ccgaaggcga acgcaggctc cttccctctg tggagttccc ccgtcgcccc    2640
tcagccccca gcgcggggac accggggcct angccggctc tccttccggg ccgacacccc    2700
cgccgtcctc cccgtcgccc gctcccctgc agacgccgcg gggtgccgg gggagcgcgt    2760
ttgctgctct gacccgcccg cgcccgggcc ggagcccgct gcgttcacgg tgcacccccc    2820
ggacagcccg ggcgcggtaa gagccccaca aatacaggct gaacgagtaa aacaaacttg    2880
aatggcctct gccaaaaccc gcgctctcgg ttttccancg cggagcgttc gcgccgatgc    2940
cggcagcctt cctcgcggga catctgctcg cgggccagga ggtggcatcg cggacctctc    3000
caggcagcgg ggccgccggg cggcggagcc caggcaaaga catcgcggtc ngaggcgctc    3060
ggaccttccc gggaggaggg ggagttgcct cggtggtttc cgagagggcg gcaccggggg    3120
acgcaggaga aaaggtgcgg gcggggggccg gagagggggac ggggcсcсgga gtgggcgccg    3180
ggaagcgtag gaggtgaagc caccggaccc acgcgcagct cggcgaggag gagggcggga    3240
aagcgcgtgg ggcgcaggcc ggggagccgg gtaggacgcg gcacctgcgg agcgcgccaa    3300
gacttccacg gcttacaaga acgtgggaga gggacccccc cttacccggc tcctctgcgc    3360
ccccaactca ccctggcccc tcatcccgcg cccctgagcc ctggagagcc gcgcgctccg    3420
cagccagtga cacgccagcc ccacccgcga ccccacgcgt tccctcggca gcccagggag    3480
gaccggggg cgcagacaga cccagggttt atcgggccgc agcgcagcgc ctccaggtcc    3540
atgtttcctc agccataaaa cagcgctagc gacgccccct gccccgcccc tccaggctgt    3600
gagaagagcc agagcctgtc ccgagcgcgg cttcctcccg ccgttccgcc cgcgcgcgcc    3660
tcctgggcct cagttcggga gacccgcacc cctcccggcc cgcccagggt ctgcccggcc    3720
gcgcagagtg ggggatccca gggcgacagc agcccccgcc ccaactccc cctgcccgcc    3780
ccccccggcc ccgcagttcc cgcgtctcag ctcagagccc gagccttggg gcgggcgcc    3840
gtcgccttgg ggtgctggga ggggcccgaa cccgacccgg gagggcссстт cctcgtgtct    3900
cctccgaggg agcggggcgc aggacaggcc ggggcgggtc tcgggccgg acgggcgctg    3960
ggggttcccg gccaggctc cgcggggcc gatcaccggt ggggcggccg cgcccaatcg    4020
aatcccaatc ccagtcgaat cgagtgcgga gtcgacgggg gaagcgaacc ccccgtgaac    4080
gcggggctgc acctcagtgg agccggaaag ccgccggggc agccccgagc gcgcacacac    4140
ccggcggccg caccactgcc ccggagtttg gccgcaggtg gcttttccaa gccgccatcc    4200
aggagcggcc gacggcgcca agtccccgcc tcgacctgca caaaacgaaa acggacgctg    4260
gagggggggcg agggggcgga cgtgagaccc cggccccgaa ccccgggcgc cgccttcctc    4320
```

-continued

```
cgcggcacag gcccgagaga ggccacgcag cggcgttccc tgcgcacaga ctcgggctcc    4380
ccacgagccg tgggccacag ccacagccgc cccgtgtccc taaatcaata cgagacgtca    4440
ccacagacgt cggagcgttt gctcgcggcc gccgtgcgcg gggctcggag tcatctcacc    4500
gcccggtctg cggatggat gagcgagcgg ctcccggtgc cgtgggggcg gggggacac     4560 cggcccccg cgcgcgtcta aggccgcgtt tctgccgctg cgcccccagc ccgcacccac    4620
gttcgggccc tggacagggc ttccgcgctg aggccgtcct ggtctctgtt ctcccggccg    4680
gggattcgcg agaggcggcc cgtgggcgaa gtcgtgggcc caggtcacat cctgggggac    4740
ccccagcggg agacctggag gccgatgacg gggaagtgcc gagccgcgcg tgtggtcccg    4800
ggacccgcct cccgccccg ctcccgcctg cctcactcct ccaccgcgcc ggccgcgtgt     4860
cggcgaaacc agaggcagct ccgtgcgagc ctcgcccggc cgtgaggccc gtggattccg    4920
tggactcgag gcccgcgtcc tccgccctcc tgtggccccg acctgcccgg agcgcgttcc    4980
ccgccggcgt ccgctgccgc tcacacccac cccagccacg ggcggcggag cagtcgcgac    5040
tgggacgcgg gccgggactc ttccccgagt ggggcgctcc gagcgcgcgg gcgggtcctc    5100
aaatctgcat tctttccgtt aataaaatac gttctcgtat ttttcctga tttcgcatga    5160 aaacctttgc ctaactacac tcccatccaa gcgggattta tttcgtcccc gggagataa     5220 atcggggcga atttacagcc cgggaggcac ctgccgcgct aatgggccct tcatggagtg    5280
cgcggccggc gggggcgcgc gggcgggggg ggggcgccgg ccaatggccg gaccgcgggg    5340
tccgcagcca atcagcgcgc gcgccgcgcc ccggcggagc cccgttatc agcgcgtccg     5400 tcccgcgcgg cgccgctccg accggccccg ggagccgccg ccgccgccgc ccgcccgccc    5460
gccccgcgcc ggagccgccc gcccgccccc cgcgcccgc gccccgcgct gcagccgacg     5520
cccgccgggg ccgcgcgcaa acttcccggg ccggcgggca ggggcggcgg cggcggggcc    5580
cggatgggag cccgggccgg cggcggcggc gcccatggac actaaccgcc cgggcgcgtt    5640
cgtgctgagc agtgccccgc tggccgcgct gcacaacatg gccgagatga agacgtcgct    5700
gttcccctac gcgctgcagg gtccggccgg cttcaaggcg cccgcgctgg ggggcctggg    5760
cgcgcagctc ccgctcggga ccccgcacgg catcagcgac atcctgggcc ggcccgtggg    5820
cgcggcgggc gggggcctcc tgggggggct gccccggctc aacgggctcg cgtcgtccgc    5880
cggcgtttac ttcgggcccg cggccgctgt ggcgcgcggc taccccaagc ccctggccga    5940
gctgccgggg cgcccgccca tcttctggcc cggcgtggtg cagggcgcgc cctggaggga    6000
cccgcgtctg gctggcccgg gtgagtggcc ccgcggggg gtgcggggcg ggtgggcgcg    6060 gaggggacc ccgccggccg ctgacctccc tcccttcccc tcccttgcag ccccggccgg    6120
cggcgtcctg acaaggacg ggaagaagaa gcactcgcgc ccgaccttct cgggccagca    6180
gatcttcgcg ctggagaaaa ccttcgagca gaccaagtac ctggcgggcc ggagcgcgc     6240 gcgtctcgcc tactcgctgg gcatgaccga gagccaggtg aaggtgagcg cggcggggct    6300
cgggagagca gagccggggg cccgcgtcct gcgaacggcc ccagcgccag cccgggccc     6360 cgcggccgcc tgaccgcccc gtccactccc aggtctggtt ccagaaccgc cggaccaagt    6420
ggcgcaagcg gcacgcggcg gagatggcgt cggccaagaa gaagcaggac tcggacgccg    6480
agaagctgaa ggtgggcgc tcggacgcgg aggacgacga cgaatacaac cggcccctgg     6540
accccaactc ggacgacgag aagatcacgc ggctgctcaa gaagcacaaa ccctcgaact    6600
tggcgctggt cagcccgtgc ggcggcggcg cggggggacg cttgtgagga cccgcggggt    6660
```

-continued

```
gggggcgaat ctattttgc agaatccggg ggcggcccg ggtgggcgcg agtcgctttg      6720
tatcatcaat aaattattta acgggtcccc gtcggagccg tcgctccgga gcctgcgccg      6780
cgtgtttctt ccgtctcgaa cccggagcga ggcggcccct cccggcccc ggcttcgccc       6840
ctgcgcccgc ctcgggtcct ccgggttccc ggtgcggang ctgcgggccc cgggcaggcg      6900
cgaggaggcg gcgaaggcgc agggaagggg cccggcccgc gggaaggaac cgcagcgaca      6960
gccgccagga gcccgggncg gngccgggga cggagcagca ggtacggccc ggcccgcctc      7020
gcctcggggc ggattcggac gcgcttgggg gttcccgaaa gggcgggtga gccgcgtacc      7080
cgcctcgagt ccccgcggga ggttttctt cttccgttt cccgctttgg ggccacgtac        7140
tcgttgccac cgggcacccg ttcccgctcg gccgagggct tcgctctgat tatttccaaa      7200
gtccctctgc gcatcagcgg atcccatagg cccgccctgg gctcagccgg tggaaccggg      7260
tctgatccgc tgcacggagg cccttcggtc accatcccgc cagatcttcc cgcggtggaa      7320
agcagtttct tccgaactag gaccgcaaag agaaatccga ataattccg cccgcggagc       7380
ggcggggcct cccgtgggtc acgcgggtc agggagccgg aggccccctg gcaaggccc        7440
gcaagcgccc agccggggg ctcggggac ccgtcttcct gccctgaaat gccgccagct        7500
ccgccggggc tgtgactgcg gctgacaaaa cccctccanc ctcccgcanc ctctgttggc      7560
cggggctgcc natccgctgc ancttaatgg gcgtggctgt tgagttttaa ttttaaaaa       7620
ttaaatgtaa ataatgatat cactgcggtg gtacgatttc tcttggcatt tgcggaagcg      7680
ttaaagggaa atagaaggg cttaaactcg gcgcgtttg ttttaggctc ttagcagcct       7740
tctttacaag gaagcaactc gaagggcaga agcaacgctt ttctgtgggg agcccctctc      7800
agctcagagc agaggggctt cttaaagttt tgaggaaggc aaagcgttga tataatcccg      7860
ttttaaaatg ttgagggata aatcctttat tacagtagaa agtccaaaag gctgtgttc       7920
tcctctcaat gaacggctta gtgttttgtg acagcgtgtg atacagtgaa attccaggat      7980
ttctaatgag cttgatctca aataaaggct atacangagg ccgctcccct gagttagcat      8040
ttcaaaggtg gcaggagaag ggaaaggaag aaaaagcaac acggggacta ttttcaccac       8100
ggtcaatttt attgcttagg aaccagaccg gtcacttcca aaggcccctc agaacgacca      8160
acagctgaaa cccgcgggc ggactccgtg ttgaaccgcg gacagcggca accacagcag       8220
cgacacggac ctgtgcttcc accaagaaca gattccgcag cggacagcag tcacttgcag      8280
tggtagtatt tatcccacac aaacacccag ctaatgcctt caccccggtc ccaggaactc      8340
tgtagtgttc taaagtaaaa atcaataaaa acatacattt gtgtttcatc aacagactct      8400
ctaatcacct tctaatgctg tacttactgc tataggagaa aaatatttgc aacaaggtta      8460
tgacatgggt tgtctgtagc ggagcaatga ggaaatgtac agttttgttt ctctttaata      8520
tttttatata cagcccatgt taaaagcagt ttctattgga agcaaactag gctatttcta      8580
tttctcccat gatattattg ttgtaacgta ggatacttgg caccataaaa cagtaacaaa      8640
agacagacaa acggtttaca aaattcttaa aaggtacacc caggctagct ataaacttca      8700
cattcagttc ttaatattac acagaagaac ggcatgggag taacgcccg ctggtgcaga       8760
cgtgctgtgg ggccgatttt acccacgatg gcgaggccat gtgtgttttt tacgaatttg      8820
tgtgttgatg gacacacagc tgagctccta gactccaatg ccgcctgctg atgggactct      8880
cctgtgcgtt catactggaa agtatattta gcataagttt tggtaagatt tataaattat      8940
ttttaaaaag tatatattta tatatattta tatatatata aaaatggaaa gcagctgcag      9000
tgtgattcaa aaaccatgtg acacggcgca gagtcagtgc cgcggaagga gcatcggcag      9060
```

-continued

| | |
|---|---|
| agacagaccc ccttgccatg ctcagggcca cgctgccggc cggcagaggg agtgcccgtc | 9120 |
| tcggcttccc cagcccctgg acacacctcc acctggcaga gggggtccct ggacacagtg | 9180 |
| gggggtctct gtgctgaaga agcccctcca ctggcaatca ttaaaaactg aaaactgtga | 9240 |
| agtctacggt acagaccctc tttgctgtct attagagttt tgacaacagg actgtgactt | 9300 |
| atttaaaaaa aaaaaaaaac caatatttct acttaatgtc acatagacag acgagacagt | 9360 |
| gaggtatgtg gggctgctcc ggaatggtcc ggaggctgaa gcgaagtgtg gggctggccg | 9420 |
| tctagcaggt ggcgcttggg cgggttctcg atgcagcttt caagagtgcg tattcggtcc | 9480 |
| acggctacag ggaggctcac gaagtgtcct ctcgtggcgc tggcatctct tcccaccacg | 9540 |
| tcactgcacg acacaacact tgtgcacatg gcatgaggt ttacctgccc cgggcatgat | 9600 |
| tcggaaggcc aggaacacgg gcttgtggtc tcccatgcag acgttgggcc caatgtggtc | 9660 |
| ataggtgaca accttctcct cgctctccga ccgcagcacc agctccttgg cagacgggga | 9720 |
| catgaggatg cggtcacacc aggctgggca ccgggtgttc atgtactgct caccctggcg | 9780 |
| ggcgtcctca ctgtacgggt agctgggagg aacgagatg tccagttcat acagtctgtc | 9840 |
| cttaaagaca gacaactcct tgtcaaactc caagagcgcg gtgccgttgt tgtctcggaa | 9900 |
| aacctcctgg ttgaagtagt cgaagagttt cttttctaac tggagcataa ccttccggtc | 9960 |
| gttgtccgac tcacgaaata tgagcttcac cacttcattg gtgtcggcgg cccggaccgt | 10020 |
| ctgcatcggt ggttttgctg agagcgtctc cacgacagac ttggaatcca gccgaaagtt | 10080 |
| gaaatcacca aatacaaagt aggaaaccct tcgaatcgc tgatcaatga ttctgtccag | 10140 |
| cacgtagccc agtgccttgt gccggattcc cgagtacacg aagggcttg tttcccaggc | 10200 |
| gaccagattg gaagcatcat ggaaagatg gatattcacc aagtcaaagg cacagtctgc | 10260 |
| aatcaccacc tcgtccggat gaagcctttt cttgaccatt tgcactcggg gaagtagtct | 10320 |
| gcgaaacttc tccttctcca gcatgggcgt gctctctaag gtatccgagt agatctcttt | 10380 |
| gccagcgacc tttctatact tcttagcttt aaagtcaaac tggtagatgt tttttaagga | 10440 |
| ctcatgaaga aaataaaagc tt | 10462 |

<210> SEQ ID NO 6
<211> LENGTH: 277
<212> TYPE: PRT
<213> ORGANISM: Human

<400> SEQUENCE: 6

Met Asp Thr Asn Arg Pro Gly Ala Phe Val Leu Ser Ser Ala Pro Leu
1               5                   10                  15

Ala Ala Leu His Asn Met Ala Glu Met Lys Thr Ser Leu Phe Pro Tyr
            20                  25                  30

Ala Leu Gln Gly Pro Ala Gly Phe Lys Ala Pro Ala Leu Gly Gly Leu
        35                  40                  45

Gly Ala Gln Leu Pro Leu Gly Thr Pro His Gly Ile Ser Asp Ile Leu
    50                  55                  60

Gly Arg Pro Val Gly Ala Ala Gly Gly Leu Gly Gly Leu Pro
65                  70                  75                  80

Arg Leu Asn Gly Leu Ala Ser Ser Ala Gly Val Tyr Phe Gly Pro Ala
                85                  90                  95

Ala Ala Val Ala Arg Gly Tyr Pro Lys Pro Leu Ala Glu Leu Pro Gly
            100                 105                 110

Arg Pro Pro Ile Phe Trp Pro Gly Val Val Gln Gly Ala Pro Trp Arg

-continued

```
                115                 120                 125
Asp Pro Arg Leu Ala Gly Pro Ala Pro Ala Gly Val Leu Asp Lys
    130                 135                 140
Asp Gly Lys Lys Lys His Ser Arg Pro Thr Phe Ser Gly Gln Gln Ile
145                 150                 155                 160
Phe Ala Leu Glu Lys Thr Phe Glu Gln Thr Lys Tyr Leu Ala Gly Pro
                165                 170                 175
Glu Arg Ala Arg Leu Ala Tyr Ser Leu Gly Met Thr Glu Ser Gln Val
            180                 185                 190
Lys Val Trp Phe Gln Asn Arg Arg Thr Lys Trp Arg Lys Arg His Ala
        195                 200                 205
Ala Glu Met Ala Ser Ala Lys Lys Gln Asp Ser Asp Ala Glu Lys
    210                 215                 220
Leu Lys Val Gly Gly Ser Asp Ala Glu Asp Asp Glu Tyr Asn Arg
225                 230                 235                 240
Pro Leu Asp Pro Asn Ser Asp Asp Glu Lys Ile Thr Arg Leu Leu Lys
                245                 250                 255
Lys His Lys Pro Ser Asn Leu Ala Leu Val Ser Pro Cys Gly Gly Gly
            260                 265                 270
Ala Gly Asp Ala Leu
        275

<210> SEQ ID NO 7
<211> LENGTH: 262
<212> TYPE: PRT
<213> ORGANISM: Mouse

<400> SEQUENCE: 7

Met Glu Ser Asn Leu Gln Gly Thr Phe Leu Asn Asn Thr Gln Leu
1               5                   10                  15
Ala Gln Phe Ser Glu Met Lys Ala Pro Met Cys Gln Tyr Ser Val Gln
            20                  25                  30
Asn Ser Phe Tyr Lys Leu Ser Pro Pro Gly Leu Gly Pro Gln Leu Ala
        35                  40                  45
Ala Gly Thr Pro His Gly Ile Thr Asp Ile Leu Ser Arg Pro Val Ala
    50                  55                  60
Thr Pro Asn Ser Ser Leu Leu Ser Gly Tyr Pro His Val Ala Gly Phe
65                  70                  75                  80
Gly Gly Leu Ser Ser Gln Gly Val Tyr Tyr Gly Pro Gln Val Gly Ser
                85                  90                  95
Phe Ser Lys Ala Gly Asn Glu Tyr Pro Thr Arg Thr Arg Asn Cys Trp
            100                 105                 110
Ala Asp Thr Gly Gln Asp Trp Arg Gly Ser Ala Arg Pro Cys Ser Asn
        115                 120                 125
Thr Pro Asp Pro Leu Ser Asp Thr Ile His Lys Lys His Thr Arg
    130                 135                 140
Pro Thr Phe Thr Gly His Gln Ile Phe Ala Leu Glu Lys Thr Phe Glu
145                 150                 155                 160
Gln Thr Lys Tyr Leu Ala Gly Pro Glu Arg Ala Arg Leu Ala Tyr Ser
                165                 170                 175
Leu Gly Met Thr Glu Ser Gln Val Lys Val Trp Phe Gln Asn Arg Arg
            180                 185                 190
Thr Lys Trp Arg Lys Lys Ser Ala Leu Glu Pro Ser Ser Thr Pro
        195                 200                 205
```

```
Arg Ala Pro Gly Gly Ala Ser Gly Asp Arg Ala Ala Ser Glu Asn Glu
    210                 215                 220
Asp Asp Glu Tyr Asn Lys Pro Leu Asp Pro Asp Ser Asp Asn Glu Lys
225                 230                 235                 240
Ile Arg Leu Leu Leu Arg Lys His Arg Ala Ala Phe Ser Val Leu Ser
                245                 250                 255
Leu Gly Ala His Ser Val
            260

<210> SEQ ID NO 8
<211> LENGTH: 365
<212> TYPE: PRT
<213> ORGANISM: Rat

<400> SEQUENCE: 8

Met Leu Ala Val Gly Ala Met Glu Gly Pro Arg Gln Ser Ala Phe Leu
1               5                   10                  15
Leu Ser Ser Pro Pro Leu Ala Ala Leu His Ser Met Ala Glu Met Lys
                20                  25                  30
Thr Pro Leu Tyr Pro Ala Ala Tyr Pro Pro Leu Pro Thr Gly Pro Pro
            35                  40                  45
Ser Ser Ser Ser Ser Ser Ser Ser Ser Pro Ser Pro Pro Leu
    50                  55                  60
Gly Ala His Asn Pro Gly Gly Leu Lys Pro Pro Ala Ala Gly Gly Leu
65                  70                  75                  80
Ser Ser Leu Gly Ser Pro Pro Gln Gln Leu Ser Ala Ala Thr Pro His
                85                  90                  95
Gly Ile Asn Asp Ile Leu Ser Arg Pro Ser Met Pro Val Ala Ser Gly
            100                 105                 110
Ala Ala Leu Pro Ser Ala Ser Pro Ser Gly Ser Ser Ser Ser Ser Ser
        115                 120                 125
Ser Ser Ala Ser Ala Thr Ser Ala Ser Ala Ala Ala Ala Ala Ala Ala
    130                 135                 140
Ala Ala Ala Ala Ala Ala Ala Ser Ser Pro Ala Gly Leu Leu Ala Gly
145                 150                 155                 160
Leu Pro Arg Phe Ser Ser Leu Ser Pro Pro Pro Pro Pro Gly Leu
                165                 170                 175
Tyr Phe Ser Pro Ser Ala Ala Ala Val Ala Ala Val Gly Arg Tyr Pro
            180                 185                 190
Lys Pro Leu Ala Glu Leu Pro Gly Arg Thr Pro Ile Phe Trp Pro Gly
        195                 200                 205
Val Met Gln Ser Pro Pro Trp Arg Asp Ala Arg Leu Ala Cys Thr Pro
    210                 215                 220
His Gln Gly Ser Ile Leu Leu Asp Lys Asp Gly Lys Arg Lys His Thr
225                 230                 235                 240
Arg Pro Thr Phe Ser Gly Gln Gln Ile Phe Ala Leu Glu Lys Thr Glu
                245                 250                 255
Glu Gln Thr Lys Tyr Leu Ala Gly Pro Glu Arg Ala Arg Leu Ala Tyr
            260                 265                 270
Ser Leu Gly Met Thr Glu Ser Gln Val Lys Val Trp Phe Gln Asn Arg
        275                 280                 285
Arg Thr Lys Trp Arg Lys Lys His Ala Ala Glu Met Ala Thr Ala Lys
    290                 295                 300
Lys Lys Gln Asp Ser Glu Thr Glu Arg Leu Lys Gly Thr Ser Glu Asn
305                 310                 315                 320
```

-continued

```
Glu Glu Asp Asp Asp Tyr Asn Lys Pro Leu Asp Pro Asn Ser Asp
                325                 330                 335

Asp Glu Lys Ile Thr Gln Leu Leu Lys His Lys Ser Ser Gly Gly
            340                 345                 350

Ser Leu Leu His Ala Ser Glu Ala Glu Gly Ser Ser
        355                 360             365
```

<210> SEQ ID NO 9
<211> LENGTH: 277
<212> TYPE: PRT
<213> ORGANISM: Mouse

<400> SEQUENCE: 9

```
Met Asp Ala Asn Arg Pro Gly Ala Phe Val Leu Ser Ser Ala Pro Leu
1               5                   10                  15

Ala Ala Leu His Asn Met Ala Glu Met Lys Thr Ser Leu Phe Pro Tyr
            20                  25                  30

Ala Leu Gln Gly Pro Ala Gly Phe Lys Thr Pro Ala Leu Gly Ser Leu
        35                  40                  45

Gly Ala Gln Leu Pro Leu Gly Thr Pro His Gly Ile Ser Asp Ile Leu
    50                  55                  60

Gly Arg Pro Val Gly Ala Ala Gly Gly Leu Leu Gly Ser Leu Pro
65                  70                  75                  80

Arg Leu Asn Gly Leu Ala Ser Ser Ala Gly Val Tyr Phe Gly Pro Ala
                85                  90                  95

Ala Ala Val Ala Arg Gly Tyr Pro Lys Pro Leu Ala Glu Leu Pro Gly
            100                 105                 110

Arg Pro Pro Ile Phe Trp Pro Gly Val Val Gln Gly Ser Pro Trp Arg
        115                 120                 125

Asp Pro Arg Leu Ala Gly Ser Ala Gln Ala Gly Gly Val Leu Asp Lys
    130                 135                 140

Asp Gly Lys Lys Lys His Ser Arg Pro Thr Phe Ser Gly Gln Gln Ile
145                 150                 155                 160

Phe Ala Leu Glu Lys Thr Phe Glu Gln Thr Lys Tyr Leu Ala Gly Pro
                165                 170                 175

Glu Arg Ala Arg Leu Ala Tyr Ser Leu Gly Met Thr Glu Ser Gln Val
            180                 185                 190

Lys Val Trp Phe Gln Asn Arg Arg Thr Lys Trp Arg Lys Arg His Ala
        195                 200                 205

Ala Glu Met Ala Ser Ala Lys Lys Lys Gln Asp Ser Asp Ala Glu Lys
    210                 215                 220

Leu Lys Val Gly Gly Ser Asp Ala Glu Asp Asp Glu Tyr Asn Arg
225                 230                 235                 240

Pro Leu Asp Pro Asn Ser Asp Asp Glu Lys Ile Thr Arg Leu Leu Lys
                245                 250                 255

Lys His Lys Pro Ser Asn Leu Ala Leu Val Ser Pro Cys Gly Gly Ser
            260                 265                 270

Ala Gly Asp Ala Leu
        275
```

<210> SEQ ID NO 10
<211> LENGTH: 272
<212> TYPE: PRT
<213> ORGANISM: Chick

<400> SEQUENCE: 10

```
Met Asp Ala Asn Arg Gln Ser Ala Phe Val Leu Gly Ser Thr Pro Leu
1               5                   10                  15

Ala Ala Leu His Asn Met Ala Glu Met Lys Ser Ser Leu Phe Pro Tyr
                20                  25                  30

Ala Leu Gln Asn Pro Ser Ser Phe Lys Ala Pro Ala Leu Gly Gly Leu
            35                  40                  45

Asn Thr Gln Leu Pro Leu Gly Thr Pro His Gly Ile Ser Asp Ile Leu
        50                  55                  60

Gly Arg Pro Val Gly Ala Ala Gly Asn Leu Leu Gly Gly Leu Pro Arg
65                  70                  75                  80

Ile Asn Gly Leu Ala Ala Ser Ala Gly Val Tyr Phe Gly Pro Ala Ala
                85                  90                  95

Val Ser Arg Tyr Pro Lys Pro Leu Ala Glu Leu Pro Gly Arg Pro Pro
            100                 105                 110

Ile Phe Trp Pro Gly Val Val Gln Gly Ser Pro Trp Arg Asp Pro Arg
        115                 120                 125

Leu Thr Cys Pro Ala Gln Thr Gly Met Val Leu Asp Lys Asp Gly Lys
    130                 135                 140

Lys Lys His Ser Arg Pro Thr Phe Ser Gly Gln Gln Ile Phe Ala Leu
145                 150                 155                 160

Glu Lys Thr Phe Glu Gln Thr Lys Tyr Leu Ala Gly Pro Glu Arg Ala
                165                 170                 175

Arg Leu Ala Tyr Ser Leu Gly Met Thr Glu Ser Gln Val Lys Val Trp
            180                 185                 190

Phe Gln Asn Arg Arg Thr Lys Trp Arg Lys Arg His Ala Ala Glu Met
        195                 200                 205

Ala Ser Ala Lys Lys Lys His Asp Ser Glu Thr Glu Lys Leu Lys Glu
    210                 215                 220

Ser Ser Asp Asn Glu Asp Asp Glu Tyr Asn Lys Pro Leu Asp Pro
225                 230                 235                 240

Asn Ser Asp Asp Glu Lys Ile Thr Arg Leu Leu Lys Lys His Lys Ser
            245                 250                 255

Thr Asn Leu Ala Leu Val Ser Pro Cys Ser Thr Ser Ser Asp Thr Leu
        260                 265                 270
```

GENETIC DEMONSTRATION OF REQUIREMENT FOR NKX6.1, NKX2.2 AND NKX6.2 IN VENTRAL NEURON GENERATION

This application is a §371 national stage of PCT International Application No. PCT/US01/27256; filed Aug. 31, 2001, designating the United States of America, which claims priority and is a continuation-in-part of U.S. Ser. No. 09/654,462, filed Sep. 1, 2000, which is a continuation-in-part of U.S. Ser. No. 09/569,259, filed May 11, 2000, the contents of which are incorporated by reference.

The invention described herein was made with government support under NIH Grants DA12462, DK21344 and DK41822. Accordingly, the United States government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

During the development of the embryonic central nervous system (CNS) the mechanisms that specify regional identity and neuronal fate are intimately linked (Anderson et al. 1997; Lumsden and Krumlauf 1996; Rubenstein et al. 1998). In the ventral half of the CNS, for example, the secreted factor Sonic hedgehog (Shh) has a fundamental role in controlling both regional pattern and neuronal fate (Tanabe and Jessell 1996; Ericson et al. 19976; Hammerschmidth et al. 1997). Shh appears to function as a gradient signal. In the spinal cord, five distinct classes of neurons can be generated in vitro in response to two- to threefold changes in the concentration of Shh, and the position at which each neuronal class is generated in vivo is predicted by the concentration required for their induction in vivo (Ericson et al. 1997a; Briscoe et al. 2000). Thus, neurons generated in more ventral regions of the neural tube require progressively higher concentrations of Shh for their induction.

The genetic programs activated in neural progenitor cells in response to Shh signaling, however, remain incompletely defined. Emerging evidence suggests that homeobox genes function as critical intermediaries in the neural response to Shh signals (Lumsden and Krumlauf 1996; Tanabe and Jessell 1996; Ericson et al. 1997; Hammerschmidt et al. 1997; Rubenstein et al. 1998). Several homeobox genes are expressed by ventral progenitor cells, and their expression is regulated by Shh. Gain-of-function studies on homeobox gene action in the chick neural tube have provided evidence that homeodomain proteins are critical for the interpretation of graded Shh signaling and that they function to delineate progenitor domains and control neuronal subtype identity (Briscoe et al. 2000). Consistent with these findings, the pattern of generation of neuronal subtypes in the basal telencephalon and in the ventral-most region of the spinal cord is perturbed in mice carrying mutations in certain Shh-regulated homeobox genes (Ericson et al. 1997; Sussel et al. 1999; Pierani et al., unpublished).

Members of the Nkx class of homeobox genes are expressed by progenitor cells along the entire rostro-caudal axis of the ventral neural tube, and their expression is dependent on Shh signaling (Rubenstein and Beachy 1998). Mutation in the Nkx2.1 or Nkx2.2 genes leads to defects in ventral neural pattering (Briscoe et al. 1999; Sussel et al. 1999), raising the possibility that Nkx genes play a key role in the control of ventral patterning in the ventral region of the CNS. Genetic studies to assess the role of Nkx genes have, however, focused on only the most ventral region of the neural tube. A recently identified Nkx gene, Nkx6.1, is expressed more widely by most progenitor cells within the ventral neural tube (Pabst et al. 1998; Qiu et al. 1998; Briscoe et al. 1999), suggesting that it may have a prominent role in ventral neural patterning. Here experiments show that in mouse embryos Nkx6.1 is expressed by ventral progenitors that give rise to motor (MN), V2, and V3 neurons. Mice carrying a null mutation of Nkx6.1 exhibit a ventral-to-dorsal switch in the identity of progenitor cells and a corresponding switch in the identity of the neuronal subtype that emerges from the ventral neural tube. The generation of MN and V2 neurons is markedly reduced, and there is a ventral expansion in the generation of a more dorsal V1 neuronal subtype. Together, these findings indicate that Nkx6.1 has a critical role in the specification of MN and V2 neuron subtype identity and, more generally, that Nkx genes play a role in the interpretation of graded Shh signaling.

SUMMARY OF THE INVENTION

This invention provides a method of converting a stem cell into a ventral neuron which comprises introducing into the stem cell a nucleic acid which expresses homeodomain transcription factor Nkx6.1 protein in the stem cell so as to thereby convert the stem cell into the ventral neuron.

This invention also provides a method of diagnosing a motor neuron degenerative disease in a subject which comprises: a) obtaining a nucleic acid sample from the subject; b) sequencing the nucleic acid sample; and c) comparing the nucleic acid sequence of step (b) with a Nkx6.1 nucleic acid sequence from a subject without motor neuron degenerative disease, wherein a difference in the nucleic acid sequence of step (b) from the Nkx6.1 nucleic acid sequence from the subject without motor neuron degenerative disease indicates that the subject has the motor neuron degenerative disease.

This invention provides a method of diagnosing a motor neuron degenerative disease in a subject which comprises: a) obtaining a nucleic acid sample from the subject; b) performing a restriction digest of the nucleic acid sample with a panel of restriction enzymes; c) separating the resulting nucleic acid fragments by size fractionation; d) hybridizing the resulting separated nucleic acid fragments with a nucleic acid probe(s) of at least 15 nucleotide capable of specifically hybridizing with a unique sequence included within the sequence of a nucleic acid molecule encoding a human Nkx6.1 protein, wherein the sequence of the nucleic acid probe is labeled with a detectable marker, and hybridization of the nucleic acid probe(s) with the separated nucleic acid fragments results in labeled probe-fragment bands; e) detecting labeled probe-fragment bands, wherein the labeled probe-fragment bands have a band pattern specific to the nucleic acid of the subject; and f) comparing the band pattern of the detected labeled probe-fragment bands of step (d) with a previously determined control sample, wherein the control sample has a unique band pattern specific to the nucleic acid of a subject having the motor neuron degenerative disease, wherein identity of the band pattern of the detected labeled probe-fragment bands of step (d) to the control sample indicates that the subject has the motor neuron degenerative disease.

This invention provides a method of treating neuronal degeneration in a subject which comprises implanting in diseased neural tissue of the subject a neural stem cell which comprises an isolated nucleic acid molecule which is capable of expressing homeodomain Nkx6.1 protein under conditions such that the stem cell is converted into a motor neuron after implantation, thereby treating neuronal degeneration in the subject.

This invention provides a method of converting a stem cell into a ventral neuron which comprises introducing into the stem cell a nucleic acid which expresses homeodomain transcription factor Nkx6.2 protein in the stem cell so as to thereby convert the stem cell into the ventral neuron.

This invention provides a method of converting a stem cell into a ventral neuron which comprises introducing into the stem cell a polypeptide which expresses homeodomain transcription factor Nkx6.1 in the stem cell so as to thereby convert the stem cell into the ventral neuron.

This invention provides a method of converting a stem cell into a ventral neuron which comprises introducing into the stem cell a polypeptide which expresses homeodomain transcription factor Nkx6.2 in the stem cell so as to thereby convert the stem cell into the ventral neuron.

This invention provides a method of diagnosing a neurodegenerative disease in a subject which comprises: a) obtaining a suitable sample from the subject; b) extracting nucleic acid from the suitable sample; c) contacting the resulting nucleic acid with a nucleic acid probe, which nucleic acid probe (i) is capable of hybridizing with the nucleic acid of Nkx6.1 or Nkx6.2 and (ii) is labeled with a detectable marker; d) removing unbound labeled nucleic acid probe; and e) detecting the presence of labeled nucleic acid, wherein the presence of labeled nucleic acid indicates that the subject is afflicted with a chronic neurodegenerative disease, thereby diagnosing a chronic neurodegenerative disease in the subject.

BRIEF DESCRIPTION OF THE FIGURES

FIGS. 1A-1U selective changes in homeobox gene expression in ventral progenitor cells in Nkx6.1 mutant embryos. (FIGS. 1A-1C) Expression of Nkx6.1 in transverse sections of the ventral neural tube of mouse embryos E9.5. (FIG. 1A) Expression of Nkx6.1 is prominent in ventral progenitor cells and persists in some post-mitotic motor neurons at both caudal hindbrain, E10.5, (FIG. 1B) and spinal cord, E12.5, (FIG. 1C) levels. (FIGS. 1D, and 1E) Summary diagrams showing domains of homeobox gene expression in wild-type mouse embryos (FIG. 1D) and the change in pattern of expression of these genes in Nkx6. 1 mutants (FIG. 1E), based on analyses at E10.0-E12.5. (FIGS. 1F-1I) Comparison of the domains of expression of Nkx6.1 (FIGS. 1F, 1J) Dbx2 (FIGS. 1G, 1H, 1K, 1L) and Gsh1 (FIGS. 1I, 1M) in the caudal neural tube of wild-type (FIGS. 1F-1I) and Nkx6.1 mutant (FIGS. 1J-1H) embryos. (FIG. 1J) Horizontal lines, approximate position of dorsoventral boundary of the neural tube; vertical lines, expression of Dbx2 and Gsh1. Expression of Sonic hedgehog, Shh (FIGS. 1N, 1R), Pax7 (FIGS. 1N, 1R), Nkx2.2 (FIGS. 1O, 1S), Pax6 (FIGS. 1P, 1S), Dbx1 (FIGS. 1P, 1T) and Nkx2.9 (FIGS. 1Q, 1U) in wild-type (FIGS. 1N-1Q) or Nkx6.1 mutant (FIGS. 1R-1U) embryos at spinal (FIGS. 1N-1P, 1R-1T) and caudal hindbrain levels (FIGS. 1Q, 1U). Arrowheads, approximate position of the dorsal limit of Nkx6.1 expression. Scale bar shown in J=100 μm (FIGS. 1A-1C); 50 μm (FIGS. 1F-1M) or 60 μm (FIGS. 1N-1U).

(FIG. 2A) Isl1/2 motor neurons; (FIGS. 10Q-10T) Absence, position of Isl1/2 dorsal D2 interneurons. Scale bar shown in I=60 μm (FIGS. 2A-2D); 80 μm (FIGS. 2E-2L); 120 μm (FIGS. 2M-2T).

(FIGS. 4G and 4H) Sim1 expression by V3 neurons in the cervical spinal cord of wild-type (FIG. 4G) and Nkx6.1 mutant (FIG. 4H) embryos. Evx1 expression by V0 neurons at caudal hindbrain levels of wild-type (FIG. 4I) and Nkx6.1 mutant (FIG. 4J) embryos. En1 (red) and Lhx3 (green) expression by separate cell populations in the ventral spinal cord of E11 wild-type (FIG. 4K) and Nkx6.1 mutant (FIG. 4L) embryos. Scale bar shown in B=60 μm (FIGS. 4A-4D); 75 μm (FIGS. 4E, 4F); 70 μm (FIGS. 4G, 4J, 4H, 4J), 35 μm (FIGS. 4K and 4L).

FIGS. 5A-5B changes in progenitor domain identity and neuronal fate in the spinal cord of Nkx6.1 mutant embryos. (FIG. 5A). In wild-type mouse embryos, cells in the Nkx6.1 progenitor domain give rise to three classes of ventral neurons: V2 neurons, motor neurons (MN) and V3 neurons. V3 neurons derive from cells in the ventral most region of Nkx6.1 expression that also express Nkx2.2 and Nkx2.9. V1 neurons derive from progenitor cells that express Dbx2 but not Nkx6.1. (FIG. 5B). In Nkx6.1 mutant embryos the domain of Dbx2 expression by progenitor cells expands ventrally, and by embyonic day 12 [E12] occupies the entire dorsoventral extent of the ventral neural tube, excluding the floor plate. Checked area indicates the gradual onset of ventral Dbx2 expression. This ventral shift in Dbx2 expression is associated with a marked decrease in the generation of V2 neurons and motor neurons and a ventral expansion in the domain of generation of V1 neurons. A virtually complete loss of MN and V2 neurons is observed at cervical levels of the spinal cord. The generation of V3 neurons (and cranial visceral motor neurons at hindbrain levels) is unaffected by the loss of Nkx6.1 or by the ectopic expression of Dbx2.

FIG. 6 human Homeobox Protein Nkx6.1. NCBI Accession No. P78426. (Inoue, H. et al., "Isolation, characterization, and chromosomal mapping of the human Nkx6.1 gene (NKX6a), a new pancreatic islet homeobox gene" Genomics 40(2):367-370, 1997). Amino acid sequence of human homeobox protein Nkx6.1 (SEQ ID NO: 1). Nkx6.1.

FIG. 7 human NK Homeobox Protein (Nkx6.1) gene, exon 1. NCBI Accession No. U66797. Segment 1 of 3 (Inoue, H. et al., "Isolation, character-ization, and chromosomal mapping of the human Nkx6.1 gene (NKX6a), a new pancreatic islet homeobox gene" Genomics 40(2):367-370, 1997). Nucleic acid sequence encoding human homeobox protein Nkx6.1, bases 1-682 (SEQ ID NO: 2).

FIG. 8 human NK Homeobox Protein (Nkx6.1) gene, exon 2. NCBI Accession No. U66798. Segment 2 of 3 (Inoue, H. et al., "Isolation, character-ization, and chromosomal mapping of the human Nkx6.1 gene (NKX6a), a new pancreatic islet homeobox gene" Genomics 40(2):367-370, 1997). Nucleic acid sequence encoding human homeobox protein Nkx6.1, bases 1-185 (SEQ ID NO: 3).

FIG. 9 human NK Homeobox Protein (Nkx6.1) gene, exon 3 and complete cds. NCBI Accession No. U66799. Segment 3 of 3 (Inoue, H. et al., "Isolation, character-ization, and chromosomal mapping of the human Nkx6.1 gene (NKX6a), a new pancreatic islet homeobox gene" Genomics 40(2):367-370, 1997). Nucleic acid sequence encoding human homeobox protein Nkx6.1, bases 1-273 (SEQ ID NO: 4). Protein encoded is shown in FIG. 7.

(K-O) Spatial patterns of expression of Pax7 and Dbx1 in different Nkx6 mutant backgrounds. (P-T) Spatial patterns of generation of Evx1/2$^+$ V0 neurons and En1$^+$ V1 neurons in different Nkx6 mutant backgrounds. (Q) The generation of V0 neurons expands ventrally into the p1 domain in Nkx6.2$^{tlz/tlz}$ mutants at caudal spinal levels. (R, A') The number of En1$^+$ V1 neurons increases ~3-fold in the ventral spinal cord of Nkx6.1$^{-/-}$ mutants, and ectopic Evx1/2$^+$ cells are detected in position of the pMN domain in these mice (see also Sander et al., 2000). (S, T A') There is a progressive increase in Evx1/2$^+$ V0 neurons and a loss of En1$^+$ V1 neurons in the ventral spinal cord of Nkx6.1$^{-/-}$;Nkx6.2 $^{+/tlz}$ and Nkx6.1 $^{-/-}$; Nkx6.2$^{tlz/tlz}$ embryos. (U,V,Z) The generation of Evx1/2$^+$ V0 neurons correlates with the pattern of expression of Dbx1 in progenitors in wt, Nkx6.2$^{tlz/tlz}$ and Nkx6.1$^{-/-}$; Nkx6.2$^{tlz/tlz}$ mutant backgrounds. Note that only the most lateral progenitor cells express Dbx1 in Nkx6.1$^{-/-}$; Nkx6.2$^{tlz/tlz}$ embryos, suggesting that expression of Dbx1 in more medially-positioned progenitors is repressed by an as yet undefined gene. (X, Y) Ectopic ventral Evx1$^+$ V0 neurons derive from Dbx1$^-$ progenitors in Nkx6.1$^{-/-}$ and Nkx6.1$^{-/-}$; Nkx6.2$^{+/tlz}$ mutant embryos. Chx10$^+$ V2 neurons are generated at normal numbers in Nkx6.2$^{tlz/tlz}$ mutants, but are missing at spinal cord levels in Nkx6.1$^{-/-}$, Nkx6.1$^{-/-}$; Nkx6.2$^{+/tlz}$ and Nkx6.1$^{-/-}$; Nkx6.2$^{tlz/tlz}$ mutants (A'.

FIG. 18 human NK Homeobox Protein (Nkx6.2) gene, complete cds. NCBI Accession No. AF184215 (SEQ ID NO: 5).

FIG. 19 human Homeobox Protein Nkx6.2. NCBI Accession No. AAK13251. Amino acid sequence of human homeobox protein Nkx6.2 (SEQ ID NO: 6).

FIG. 20 comparison of Amino Acid Sequences of Nkx6.2 Protein of Various Species with Other Nkx Protein Sequences. mNk6.3=mouse amino acid sequence of Nkx6.3 protein (SEQ ID NO: 7); rNkx6.1=rat amino acid sequence of Nkx6.1 protein (SEQ ID NO: 8); mNkx6.2=mouse amino acid sequence of Nkx6.2 protein (SEQ ID NO: 9); and cNkx6.2=chick amino acid sequence of Nkx6.2 protein (SEQ ID NO: 10).

DETAILED DESCRIPTION OF THE INVENTION

Figure 1:
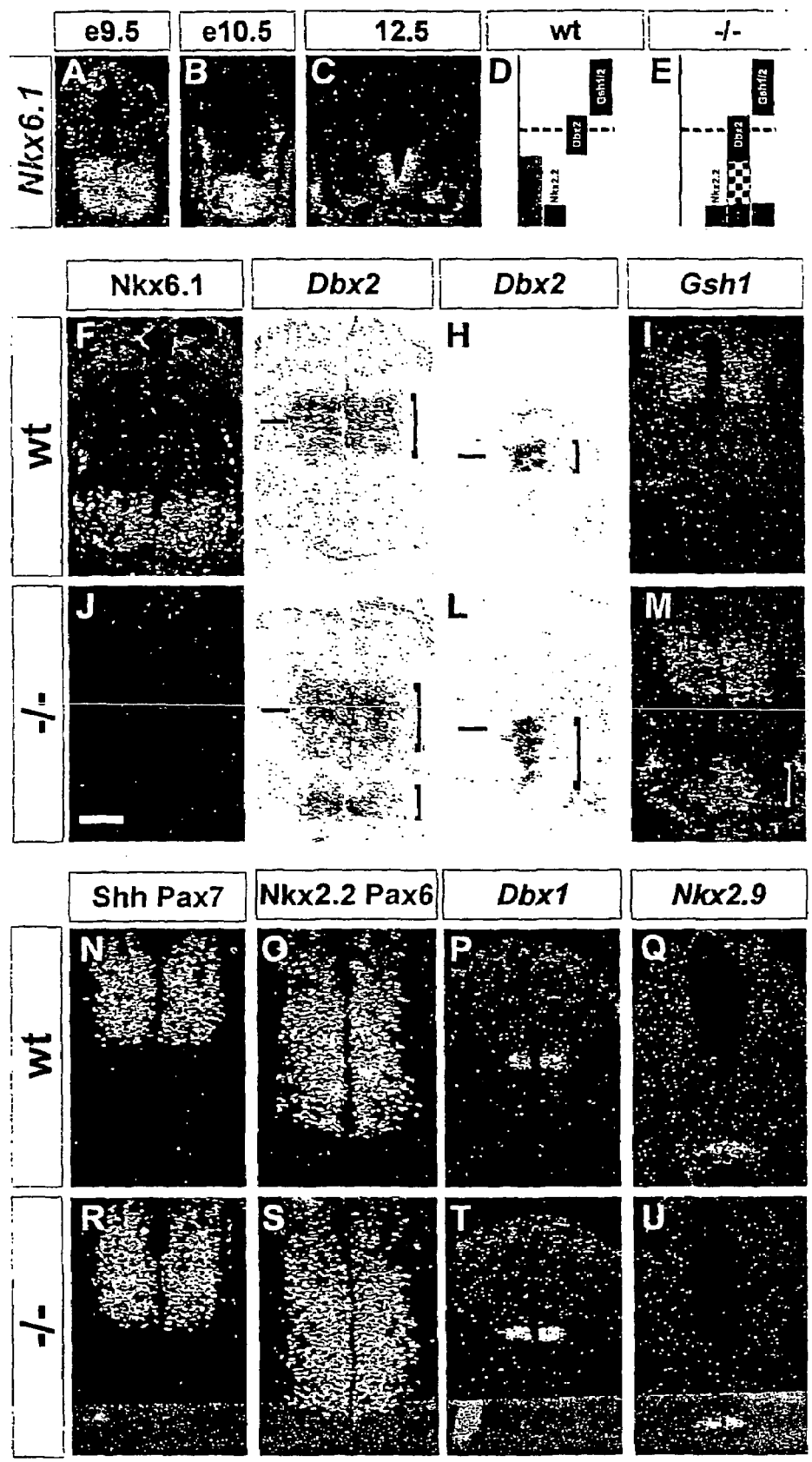
Figure 2:
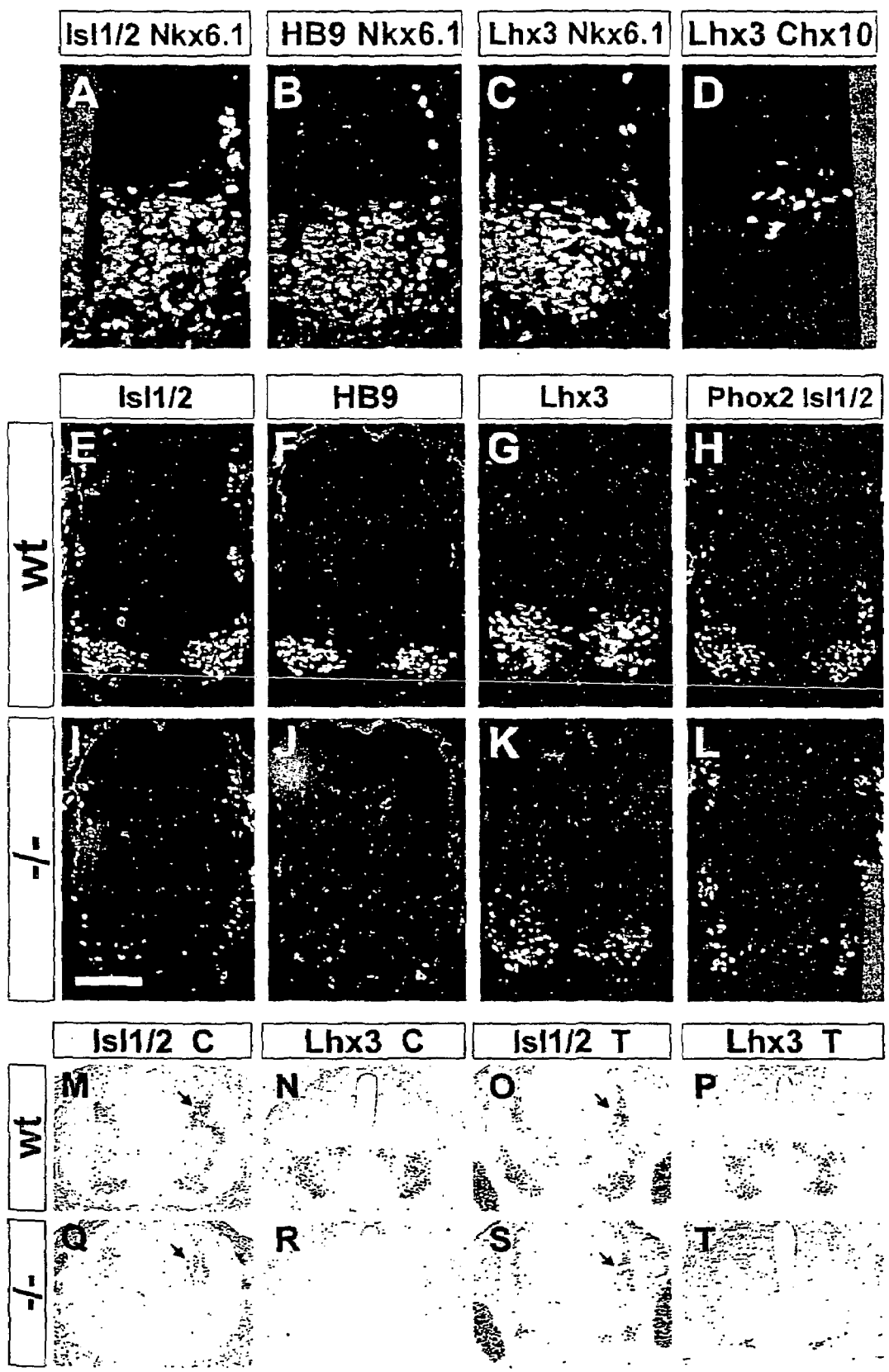
FIGS. 2A-2T disruption of motor neuron differentiation in Nkx6.1 mutant embryos. The relationship between the domain of Nkx6.1 expression (FIGS. 2A-2C, green) by ventral progenitors and the position of generation of motor neurons and V2 interneurons (FIGS. 2A-2D) in the ventral spinal cord of E10.5 wild-type embryos.
(FIG. 2B) HB9 motor neurons.
(FIG. 2C) Lhx3 (Lim3) expression (red) by motor neurons, V2 interneurons and their progenitors is confined to the Nkx6.1 progenitor domain.
(FIG. 2D) Chx10 (green) V2 interneurons coexpress Lhx3 (red). Expression of Isl1/2 (FIGS. 2E, 2I), HB9 (FIGS. 2F, 2J), Lhx3 (FIGS. 2G, 2K) and Phox2a/b (FIGS. 2H, 2L) in the ventral spinal cord (FIGS. 2E, 2F, 2G) and caudal hindbrain (FIG. 2H) of E10.5 wild-type (FIGS. 2E-2H) and Nkx6.1 mutant (FIGS. 2I-2L) embryos. Pattern of expression of Isl1/2 and Lhx3 at cervical (FIGS. 2M, 2N, 2Q, 2R) and thoracic (FIGS. 2O, 2P, 2S, 2T) levels of E12.5 wild-type (FIGS. 2M-2P) and Nkx6.1 mutant (FIGS. 2Q-2T) embryos. Arrows, position of Isl1 dorsal D2 interneurons.

As used herein, the following standard abbreviations are used throughout the specification to indicate specific amino acids:

A=ala=alanine R=arg=arginine

N=asn=asparagine D=asp=aspartic acid

C=cys=cysteine Q=gln=glutamine

E=glu=glutamic acid G=gly=glycine

H=his=histidine I=ile=isoleucine

L=leu=leucine K=lys=lysine

M=met=methionine F=phe=phenylalanine

P=pro=proline S=ser=serine

T=thr=threonine W=trp=tryptophan

Y=tyr=tyrosine V=val=valine

B=asx=asparagine or aspartic acid

Z=glx=glutamine or glutamic acid

As used herein, the following standard abbreviations are used throughout the specification to indicate specific nucleotides: C=cytosine; A=adenosine; T=thymidine; G=guanosine; and U=uracil.

This invention provides a method of converting a stem cell into a ventral neuron which comprises introducing into the stem cell a nucleic acid which expresses homeodomain transcription factor Nkx6.1 protein in the stem cell so as to thereby convert the stem cell into the ventral neuron.

In an embodiment of the above-described method of converting a stem cell into a ventral neuron, the nucleic acid introduced into the stem cell incorporates into the chromosomal DNA of the stem cell. In a further embodiment of the method, the nucleic acid is introduced by transfection or transduction. In another further embodiment of the method, the ventral neuron is a motor neuron, a V2 neuron or a V3 neuron.

As used herein, the term "nucleic acid" refers to either DNA or RNA, including complementary DNA (cDNA), genomic DNA and messenger RNA (mRNA). As used herein, "genomic" means both coding and non-coding regions of the isolated nucleic acid molecule. "Nucleic acid sequence" refers to a single- or double-stranded polymer of deoxyribonucleotide or ribonucleotide bases read from the 5' to the 3' end. It includes both replicating vectors, infectious polymers of DNA or RNA and nonfunctional DNA or RNA.

The nucleic acids of the subject invention also include nucleic acids coding for polypeptide analogs, fragments or derivatives which differ from the naturally-occurring forms in terms of the identity of one or more amino acid residues (deletion analogs containing less than all of the specified residues; substitution analogs wherein one or more residues are replaced by one or more residues; and addition analogs, wherein one or more resides are added to a terminal or medial portion of the polypeptide) which share some or all of the properties of the naturally-occurring forms.

The nucleic acid sequences include both the DNA strand sequence that is transcribed into RNA, the complementary DNA strand, and the RNA sequence that is translated into protein. The nucleic acid includes both the full length nucleic acid sequence as well as non-full length sequences. It being further understood that the sequence includes the degenerate codons of the native sequence or sequences which may be introduced to provide codon preference in a specific host cell.

As used herein, "protein", "peptide" and "polypeptide" are used to denote two or more amino acids linked by a peptidic bond between the α-carboxyl group of one amino acid and the α-amino group of the next amino acid. Peptide includes not only the full-length protein, but also partial-length fragments. Peptides may be produced by solid-phase synthetic methods that are well-known to those skilled in the art. In addition to the above set of twenty-two amino acids that are used for protein synthesis in vivo, peptides may contain additional amino acids, including but not limited to hydroxyproline, sarcosine, and γ-carboxyglutamate. The peptides may contain modifying groups including but not limited to sulfate and phosphate moieties. Peptides can be comprised of L- or D-amino acids, which are mirror-image forms with differing optical properties. Peptides containing D-amino acids have the advantage of being less susceptible to proteolysis in vivo.

Peptides may by synthesized in monomeric linear form, cyclized form or as oligomers such as branched multiple antigen peptide (MAP) dendrimers (Tam et al. Biopolymers 51:311, 1999). Nonlinear peptides may have increased binding affinity by virtue of their restricted conformations and/or oligomeric nature. Peptides may also be produced using recombinant methods as either isolated peptides or as a portion of a larger fusion protein that contains additional amino acid sequences.

Peptides may be chemically conjugated to proteins by a variety of well-known methods. Such peptide-protein conjugates can be formulated with a suitable adjuvant and administered parenterally for the purposes of generating polyclonal and monoclonal antibodies to the peptides of interest. Alternatively, unconjugated peptides can be formulated with adjuvant and administered to laboratory animals for the purposes of generating antibodies. Methods for generating and isolating such antibodies are well-known to those skilled in the art.

The nucleic acids of the subject invention include but are not limited to DNA, RNA, mRNA, synthetic DNA, genomic DNA, and cDNA.

The nucleic acid sequence of the Nkx6.2 gene for various species may be found under the following NCBI Accession Nos.: human: AF184215; N55046; N50716N; H49739; H46204; H18874; mouse: BB449783; AV331479; BB358883; BB355466; L08074; and D.melanogaster: AF220236.

The amino acid sequence of the Nkx6.2 protein for various species may be found under the following NCBI Accession Nos.: AAK13251; MXKN2; MXKN1; S35304; T28492; AAF33780; P01524; P01523; 9GSSB; 17GSB; 1BH5D; 4GSSB; 1PGTB; 1GSUB; 1GNWB; 2GLRB; 1AGSB.

As used herein, the term "introducing into a cell" includes but is not limited to transduction and transfection. Transfection can be achieved by calcium phosphate co-precipitates, conventional mechanical procedures such as microinjection, electroporation, insertion of a plasmid encased in liposomes, or virus vectors or any other method known to one skilled in the art. This invention provides an antibody produced by the above method.

This invention provides a method of diagnosing a motor neuron degenerative disease in a subject which comprises: a) obtaining a nucleic acid sample from the subject; b) sequencing the nucleic acid sample; and c) comparing the nucleic acid sequence of step (b) with a Nkx6.1 nucleic acid sequence from a subject without motor neuron degenerative disease, wherein a difference in the nucleic acid sequence of step (b) from the Nkx6.1 nucleic acid sequence from the subject without motor neuron degenerative disease indicates that the subject has the motor neuron degenerative disease.

In an embodiment of the above-described method of diagnosing a motor neuron degenerative disease in a subject the motor neuron degenerative disease is amyotrophic lateral sclerosis or spinal muscular atrophy.

As used herein, the term "sample" includes but is not limited to tonsil tissue, lymph nodes, spleen, skin lesions, blood, serum, plasma, cerebrospinal fluid, lymphocytes, urine, transudates, exudates, bone marrow cells, or supernatant from a cell culture.

As used herein, "subject" means any animal or artificially modified animal. Artificially modified animals include, but are not limited to, SCID mice with human immune systems. The subjects include but are not limited to mice, rats, dogs, guinea pigs, ferrets, rabbits, chicken and primates. In the preferred embodiment, the subject is a human being.

This invention provides a method of diagnosing a motor neuron degenerative disease in a subject which comprises: a) obtaining a nucleic acid sample from the subject; b) performing a restriction digest of the nucleic acid sample with a panel of restriction enzymes; c) separating the resulting nucleic acid fragments by size fractionation; d) hybridizing the resulting separated nucleic acid fragments with a nucleic acid probe(s) of at least 15 nucleotide capable of specifically hybridizing with a unique sequence included within the sequence of a nucleic acid molecule encoding a human Nkx6.1 protein, wherein the sequence of the nucleic acid probe is labeled with a detectable marker, and hybridization of the nucleic acid probe(s) with the separated nucleic acid fragments results in labeled probe-fragment bands; e) detecting labeled probe-fragment bands, wherein the labeled probe-fragment bands have a band pattern specific to the nucleic acid of the subject; and f) comparing the band pattern of the detected labeled probe-fragment bands of step (d) with a previously determined control sample, wherein the control sample has a unique band pattern specific to the nucleic acid of a subject having the motor neuron degenerative disease, wherein identity of the band pattern of the detected labeled probe-fragment bands of step (d) to the control sample indicates that the subject has the motor neuron degenerative disease.

In an embodiment of the above-described method of diagnosing a motor neuron degenerative disease in a subject the nucleic acid is DNA. In a further embodiment of the above-described method the nucleic acid is RNA. In another embodiment the size fractionation in step (c) is effected by a polyacrylamide or agarose gel. In another embodiment the detectable marker is radioactive isotope, enzyme, dye, biotin, a fluorescent label or a chemiluminescent label. In yet another embodiment the motor neuron degenerative disease is amyotrophic lateral sclerosis or spinal muscular atrophy.

As used herein, "detectable marker" includes but is not limited to a radioactive label, or a calorimetric, a luminescent, or a fluorescent marker. As used herein, "labels" include radioactive isotopes, fluorescent groups and affinity moieties such as biotin that facilitate detection of the labeled peptide. Other labels and methods for attaching labels to compounds are well-known to those skilled in the art.

The phrase "specifically hybridizing" and the phrase "selectively hybridizing" describe a nucleic acid that hybridizes, duplexes or binds only to a particular target DNA or RNA sequence when the target sequences are present in a preparation of total cellular DNA or RNA. By selectively hybridizing it is meant that a nucleic acid binds to a given target in a manner that is detectable in a different manner from non-target sequence under high stringency conditions of hybridization. "Complementary", "antisense" or "target" nucleic acid sequences refer to those nucleic acid sequences which selectively and specifically hybridize to a nucleic acid. Proper annealing conditions depend, for example, upon a nucleic acid's length, base composition, and the number of mismatches and their position on the nucleic acid, and must often be determined empirically. For discussions of nucleic acid design and annealing conditions for hybridization, see, for example, Sambrook et al. (1989) *Molecular Cloning: A Laboratory Manual* (2nd ed.), Cold Spring Harbor Laboratory, Vols. 1-3 or Ausubel, F., et al. (1987) *Current Protocols in Molecular Biology*, New York. The above hybridizing nucleic acids may vary in length. The hybridizing nucleic acid length includes but is not limited to a nucleic acid of at least 15 nucleotides in length, of at least 25 nucleotides in length, or at least 50 nucleotides in length.

This invention provides a method of treating neuronal degeneration in a subject which comprises implanting in diseased neural tissue of the subject a neural stem cell which comprises an isolated nucleic acid molecule which is capable of expressing homeodomain Nkx6.1 protein under conditions such that the stem cell is converted into a motor neuron after implantation, thereby treating neuronal degeneration in the subject.

This invention provides a method of converting a stem cell into a ventral neuron which comprises introducing into the stem cell a nucleic acid which expresses homeodomain transcription factor Nkx6.2 protein in the stem cell so as to thereby convert the stem cell into the ventral neuron.

In one embodiment of the above method, the nucleic acid introduced into the stem cell incorporates into the chromosomal DNA of the stem cell. In another embodiment of the above method, the nucleic acid is introduced by transfection or transduction. In a further embodiment of the above method, the ventral neuron is a motor neuron.

This invention provides a method of converting a stem cell into a ventral neuron which comprises introducing into the stem cell a polypeptide which expresses homeodomain transcription factor Nkx6.1 in the stem cell so as to thereby convert the stem cell into the ventral neuron. In one embodiment of the above method, the ventral neuron is a motor neuron, a V2 interneuron or a V3 interneuron.

This invention provides a method of converting a stem cell into a ventral neuron which comprises introducing into the stem cell a polypeptide which expresses homeodomain transcription factor Nkx6.2 in the stem cell so as to thereby convert the stem cell into the ventral neuron. In one embodiment of the above method, the ventral neuron is a motor neuron.

This invention provides a method of diagnosing a neurodegenerative disease in a subject which comprises: a) obtaining a suitable sample from the subject; b) extracting nucleic acid from the suitable sample; c) contacting the resulting nucleic acid with a nucleic acid probe, which nucleic acid probe (i) is capable of hybridizing with the nucleic acid of Nkx6.1 or Nkx6.2 and (ii) is labeled with a detectable marker; d) removing unbound labeled nucleic acid probe; and e) detecting the presence of labeled nucleic acid, wherein the presence of labeled nucleic acid indicates that the subject is afflicted with a chronic neurodegenerative disease, thereby diagnosing a chronic neurodegenerative disease in the subject.

In one embodiment of the above method, the suitable sample is spinal fluid. In another embodiment of the above method, the nucleic acid is DNA. In a further embodiment of the above method, the nucleic acid is RNA.

This invention will be better understood from the Experimental Details which follow. However, one skilled in the art will readily appreciate that the specific methods and results discussed are merely illustrative of the invention as described more fully in the claims which follow thereafter.

First Series of Experiments

Experimental Details

A. Materials and Methods

Generation of Nkx6.1 Null Mutation

A null mutation in Nkx6.1 was generated by using gene targeting in 129-strain ES cells by excising an 800-bp NotI fragment containing part of exon 1 and replacing it by a PGK-neo cassette (Sander and German, unpubl.) Mutants were born at Mendelian frequency and died soon after birth; they exhibited movements only upon tactile stimulation.

Immunocytochemistry and In Situ Hybridization

Localization of mRNA was performed by in situ hybridization following the method of Schaeren-Wiemers and Gerfin-Moser (1993). The Dbx2 riboprobe comprised the 5' EcoR1 fragment of the mouse cDNA (Pierani et al. 1999). Probes for other cDNAs were cited in the text and used as described therein. Protein expression was localized by indirect fluorescence immunocytochemistry or peroxidase immunocytochemistry (Briscoe et al. 1999; Ericson et al. 1997). Nkx6.1 was detected with a rabbit antiserum (Briscoe et al. 1999). Antisera against Shh, Pax7, Isl1/2, HB9, Lhx3, Chx10, Phox2a/b, En1, and Pax2 have been described (Briscoe et al. 1999; Ericson et al. 1997). Fluorescence detection was carried out using an MRC 1024 Confocal Microscope (BioRad).

B. Results and Discussion

To define the role of Nkx6.1 in neural development, we compared patterns of neurogenesis in the embryonic spinal cord and hindbrain of wild-type mice and mice lacking Nkx6.1 (Sander et al. 1998). In wild-type embryos, neural expression of Nkx6.1 is first detected at spinal cord and caudal hindbrain levels at about embryonic day 8.5 (E8.5; Qiu et al. 1998; data not shown), and by E9.5 the gene is expressed throughout the ventral third of the neural tube (FIG. 1A). The expression of Nkx6.1 persists until at least E12.5 (FIGS. 1B, 1C; data not shown). Nkx6.1 expression was also detected in mesodermal cells flanking the ventral spinal cord (FIGS. 1B, 1C). To define more precisely the domain of expression of Nkx6.1, we compared its expressions with that of ten homeobox genes—Pax3, Pax7, Gsh1, Gsh2, Irx3, Pax6, Dbx1, Dbx1, Dbx2 and Nkx2.9—that have been shown to define discrete progenitor cell domains along the dorsoventral axis of the ventral neural tube (Goulding et al. 1991; Valerius et al. 1995; Ericson et al. 1997; Pierani et al. 1999; Briscoe et al. 2000).

This analysis revealed that the dorsal boundary of Nkx6.1 expression is positioned ventral to the boundaries of four genes expressed by dorsal progenitor cells: Pax3, Pax7, Gsh1 and Gsh2 (FIGS. 1I, 1N; and data not shown). Within the ventral neural tube, the dorsal boundary of Nkx6.1 expression is positioned ventral to the domain of Dbx1 expression and close to the ventral boundary of Dbx2 expression (FIGS. 1G, 1H, and 1P). The domain of Pax6 expression extends ventrally into the domain of Nkx6.1 expression (FIG. 1O), whereas the expression of Nkx2.2 and Nkx2.9 overlaps with the ventral-most domain of Nkx6.1 expression (FIGS. 1O, 1Q).

To address the function of Nkx6.1 in neural development, we analyzed progenitor cell identity and the pattern of neuronal differentiation in Nkx6.1 null mutant mice (Sander et al. 1998). We detected a striking change in the profile of expression of three homeobox genes, Dbx2, Gsh1 and Gsh2, in Nkx6.1 mutants. The domains of expression of Dbx2, Gsh1 and Gsh2 each expanded into the ventral neural tube (FIGS. 1K-1M; data not shown). At E10.5, Dbx2 was expressed at high levels by progenitor cells adjacent to the floor plate, but at this stage ectopic Dbx2 expression was detected only at low levels in regions of the neural tube that generate motor neurons (FIG. 1K). By E12.5, however, the ectopic ventral expression of Dbx2 had become more uniform, and now clearly included the region of motor neuron and V2 neuron generation (FIG. 1L). Similarly, in Nkx6.1 mutants, both Gsh1 and Gsh2 were ectopically expressed in a ventral domain of the neural tube, and also in adjacent paraxial mesodermal cells (FIG. 1M; data not shown).

The ventral limit of Pax6 expression was unaltered in Nkx6.1 mutants, although the most ventrally located cells within this progenitor domain expressed a higher level of Pax6 protein than those in wild-type embryos (FIGS. 1O, 1S). We detected no change in the patterns of expression of Pax3, Pax7, Dbx1, Irx3, Nkx2.2, or Nkx2.9 in Nkx6.1 mutant embryos (FIGS. 1R-1U; data not shown). Importantly, the level of Shh expression by floor plate cells was unaltered in Nkx6.1 mutants (FIGS. 1N and 1R). Thus, the loss of Nkx6.1 function deregulates the patterns of expression of a selected subset of homeobox genes in ventral progenitor cells, without an obvious effect on Shh levels (FIGS. 1D, 1E). The role of Shh in excluding Dbx2 from the most ventral region of the neural tube (Pierani et al. 1999) appears therefore to be mediated through the induction of Nkx6.1 expression. Consistent with this view, ectopic expression of Nkx6.1 represses Dbx2 expression in chick neural tube (Briscoe et al. 2000). The detection of sites of ectopic Gsh1/2 expression in the paraxial mesoderm as well as the ventral neural tube, both sites of Nkx6.1 expression, suggests that Nkx6.1 has a general role in restricting Gsh1/2 expression. The signals that promote ventral Gsh1/2 expression in Nkx6.1 mutants remain unclear, but could involve factors other than Shh that are secreted by the notochord (Hebrok et al. 1998).

The domain of expression of Nkx6.1 within the ventral neural tube of wild-type embryos encompasses the progenitors of three main neuronal classes: V2 interneurons, motor neurons and V3 interneurons (Goulding et al. 1991; Ericson et al. 1997; Qiu et al. 1998; Briscoe et a. 1999, 2000; Pierani et al. 1999; FIGS. 2A-2D). We examined whether the generation of any of these neuronal classes is impaired in Nkx6.1 mutants, focusing first on the generation of motor neurons. In Nkx6.1 mutant embryos there was a marked reduction in the number of spinal motor neurons, as assessed by expression of the homeodomain proteins Lhx3, Isl1/2 and HB9 (Arber et al. 1999; Tsuchida et al. 1994; FIGS. 2E-2L), and by expression of the gene encoding the transmitter synthetic enzyme choline acetyltransferase (data not shown). In addition, few if any axons were observed to emerge from the ventral spinal cord (data not shown). The incidence of motor neuron loss, however, varied along the rostrocaudal axis of the spinal cord. Few if any motor neurons were detected at caudal cervical and upper thoracic levels of Nkx6.1 mutants analyzed at E11-E12.5 (FIGS. 2M, 2N, 2Q, 2R), whereas motor neuron number was reduced only by 50%-75% at more caudal levels (FIGS. 2O, 2P, 2S, 2T; data not shown). At all axial levels, the initial reduction in motor neuron number persisted at both E12.5 and p0 (FIGS. 2M-2T; data not shown), indicating that the loss of Nkx6.1 activity does not simply delay motor neuron generation. Moreover, we detected no increase in the incidence of TUNEL$^+$ cells in Nkx6.1 mutants (data not shown), providing evidence that the depletion of motor neurons does not result solely from apoptotic death.

Figure 3:
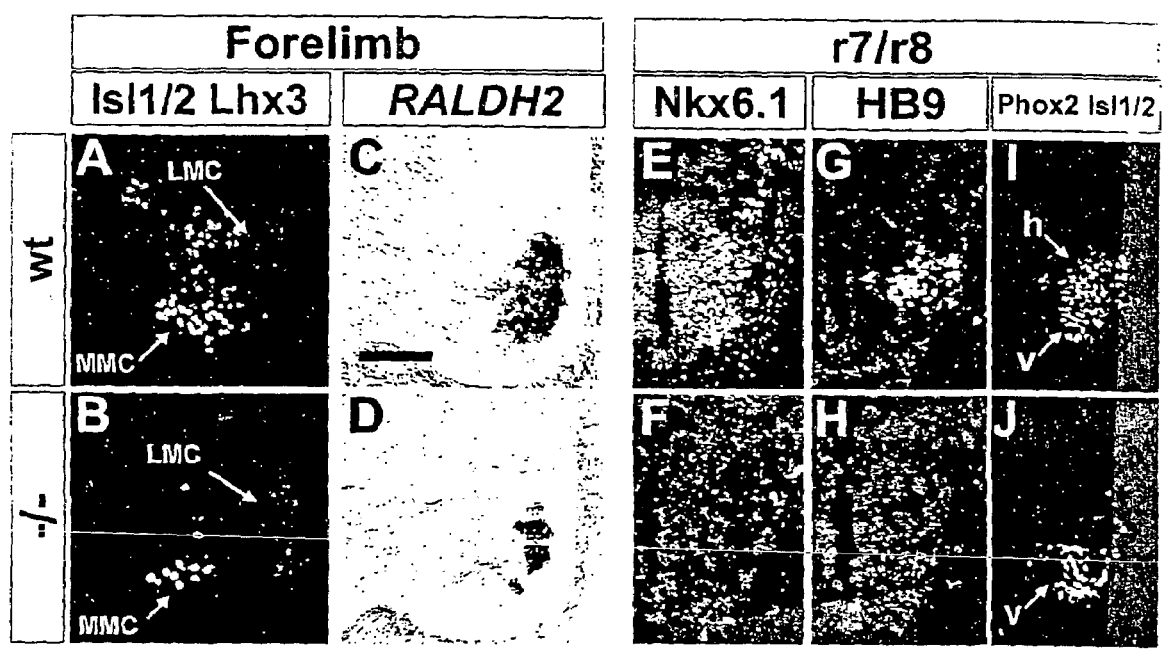
FIGS. 3A-3J motor neuron subtype differentiation in Nkx6.1 mutant mice. Depletion of both median motor column (MMC) and lateral motor column (LMC) neurons in Nkx6.1 mutant mice. Expression of Is1/2 (red) and Lxh3 (green) in E12.5 wilt-type (FIGS. 3A, 3C) and Nkx6.1 mutant (FIGS. 3B, 3D) mice spinal cord at forelimb levels (FIGS. 3E-3J). Motor neuron generation at caudal hindbrain level (FIGS. 3E, 3F) Nkx6.1 expression in progenitor cells and visceral motor neurons in the caudal hindbrain (rhombomere [r] 7/8) of E10.5-E11 wild-type (FIG. 3E) Nkx6.1 mutant (FIG. 3F) mice. HB9 expression in hypoglossal motor neurons in E10.5-E11 wild-type mice (FIG. 3G) and Nkx6.1 mutant (FIG. 3H) mice. Coexpression of Isl1 (green) and Phox2a/b (red) in wild-type (FIG. 3I) or Nkx6.1 mutant (FIG. 3J) mice. (h) hypoglossal motor neurons; (v) visceral vagal motor neurons. Scale bar shown in C=50 μm (FIGS. 3A-3D) or 70 μm (FIGS. 3E-3J).

The persistence of some spinal motor neurons in Nkx6.1 mutants raised the possibility that the generation of particular subclasses of motor neurons is selectively impaired. To address this issue, we monitored the expression of markers of distinct subtypes of motor neurons at both spinal and hindbrain levels of Nkx6.1 mutant embryos. At spinal levels, the extent of the reduction in the generation of motor neurons that populate the median (MMC) and lateral (LMC) motor columns was similar in Nkx6.1 mutants, as assessed by the number of motor neurons that coexpressed Isl1/2 and Lhx3 (defining MMC neurons, FIGS. 3A, 3B) and by the expression of Raldh2 (defining LMC neurons, Sockanathan and Jessell 1998; Arber et al. 1999; FIGS. 3C, 3D). In addition, the generation of autonomic visceral motor neurons was reduced to an extent similar to that of somatic motor neurons at thoracic levels of the spinal cord of E12.5 embryos (data not shown). Thus, the loss of Nkx6.1 activity depletes the major subclasses of spinal motor neurons to a similar extent.

At hindbrain levels, Nkx6.1 is expressed by the progenitors of both somatic and visceral motor neurons (FIGS. 3E, 3F; data not shown). We therefore examined whether the loss of Nkx6.1 might selectively affect subsets of cranial motor neurons. We detected a virtually complete loss in the generation of hypoglossal and abducens somatic motor neurons in Nkx6.1 mutants, as assessed by the absence of dorsally generated HB9$^+$ motor neurons (FIGS. 3G, 3H; data not shown, Arber et al. 1999; Briscoe et al. 1999). In contrast, there was no change in the initial generation of any of the cranial visceral motor neuron populations, assessed by coexpression of Isl1 and Phox2a (Briscoe et al. 1999; Pattyn et al. 1997) within ventrally generated motor neurons (FIGS. 3I, 3J; data not shown). Moroever, at rostral cervical levels, the generation of spinal accessory motor neurons (Ericson et al. 1997) was also preserved in Nkx6.1 mutants (data not shown). Thus, in the hindbrain the loss of Nkx6.1 activity selectively eliminates the generation of somatic motor neurons, while leaving visceral motor neurons intact. Cranial visceral motor neurons, unlike spinal visceral motor neurons, derive from progenitors that express the related Nkx genes Nkx2.2 and Nkx2.9 (Briscoe et al. 1999). The preservation of cranial visceral motor neurons in Nkx6.1 mutant embryos may therefore reflect the dominant activities of Nkx2.2 and Nkx2.9 within these progenitor cells.

Figure 4:
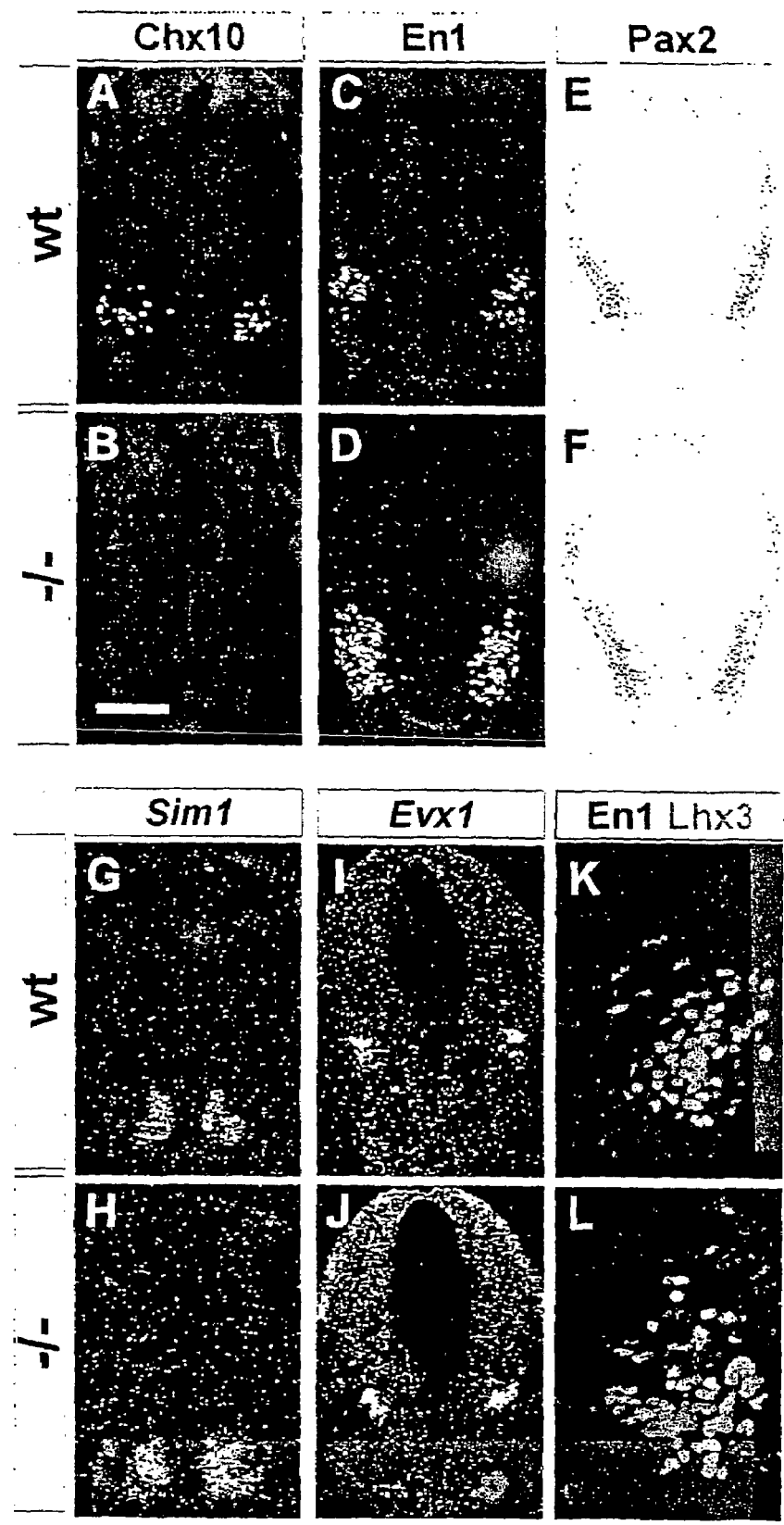
FIGS. 4A-4L a switch in ventral interneuron fates in Nkx6.1 mutant mice. Chx10 expression in V2 neurons at rostral cervical levels of E10.5 wild-type (FIG. 4A) and Nkx6.1 mutant (FIG. 4B) embryos. En1 expression by V1 neurons at rostral cervical levels of wild-type (FIG. 4C) and Nkx6.1 mutant (FIG. 4D) embryos. Pax2 expression in a set of interneurons that includes V1 neurons ((Burrill et al. 1997) at caudal hindbrain levels of wild-type (FIG. 4E) and Nkx6.1 mutant (FIG. 4F) embryos.

We next examined whether the generation of ventral interneurons is affected by the loss of Nkx6.1 activity. V2 and V3 interneurons are defined, respectively, by expression of Chx10 and Sim1 (Arber et al. 1999; Briscoe et al. 1999; FIGS. 4A, 4G). A severe loss of Chx10 V2 neurons was detected in Nkx6.1 mutants at spinal cord levels (FIG. 4B), although at hindbrain levels of Nkx6.1 mutants ~50% of V2 neurons persisted (data not shown). In contrast, there was no change in the generation of Sim1 V3 interneurons at any axial level of Nkx6.1 mutants (FIG. 4H). Thus, the elimination of Nkx6.1 activity affects the generation of only one of the two major classes of ventral interneurons that derive from the Nkx6.1 progenitor cell domain.

Evx1+, Pax2+ V1 interneurons derive from progenitor cells located dorsal to the Nkx6.1 progenitor domain, (FIG. 4B) within a domain that expresses Dbx2, but not Dbx1 (Burrill et al. 1997; Matise and Joyner 1997; Pierani et al. 1999). Because Dbx2 expression undergoes a marked ventral expansion in Nkx6.1 mutants, we examined whether there might be a corresponding expansion in the domain of generation of V1 neurons. In Nkx6.1 mutants, the region that normally gives rise to V2 neurons and motor neurons now also generated V1 neurons, as assessed by the ventral shift in expression of the En1 and Pax2 homeodomain proteins (FIGS. 4B, 4C, 4E, 4F). Consistent with this, there was a two- to threefold increase in the total number of V1 neurons generated in Nkx6.1 mutants (FIGS. 4C, 4D). In contrast, the domain of generation of Evx1/2 V0 neurons, which derive from the Dbx1 progenitor domain (Pierani et al. 1999), was unchanged in Nkx6.1 mutants (FIGS. 4I, 4J). Thus, the ventral expansion in Dbx2 expression is accompanied by a selective switch in interneuronal fates, from V2 neurons to V1 neurons. In addition, we observed that some neurons within the ventral spinal cord of Nkx6.1 mutants coexpressed the V1 marker En1 and the V2 marker Lhx3 (FIGS. 4K, 4L). The coexpression of these markers is rarely if ever observed in single neurons in wild type embryos (Ericson et al. 1996). Thus, within individual neurons in Nkx6.1 mutants, the ectopic program of V1 neurogenesis appears to be initiated in parallel with a residual, albeit transient, program of V2 neuron generation. This result complements observations in Hb9 mutant mice, in which the programs of V2 neuron and motor neuron generation coincide transiently within individual neurons (Arber et al. 1999; Thaler et al. 1999).

Figure 5:
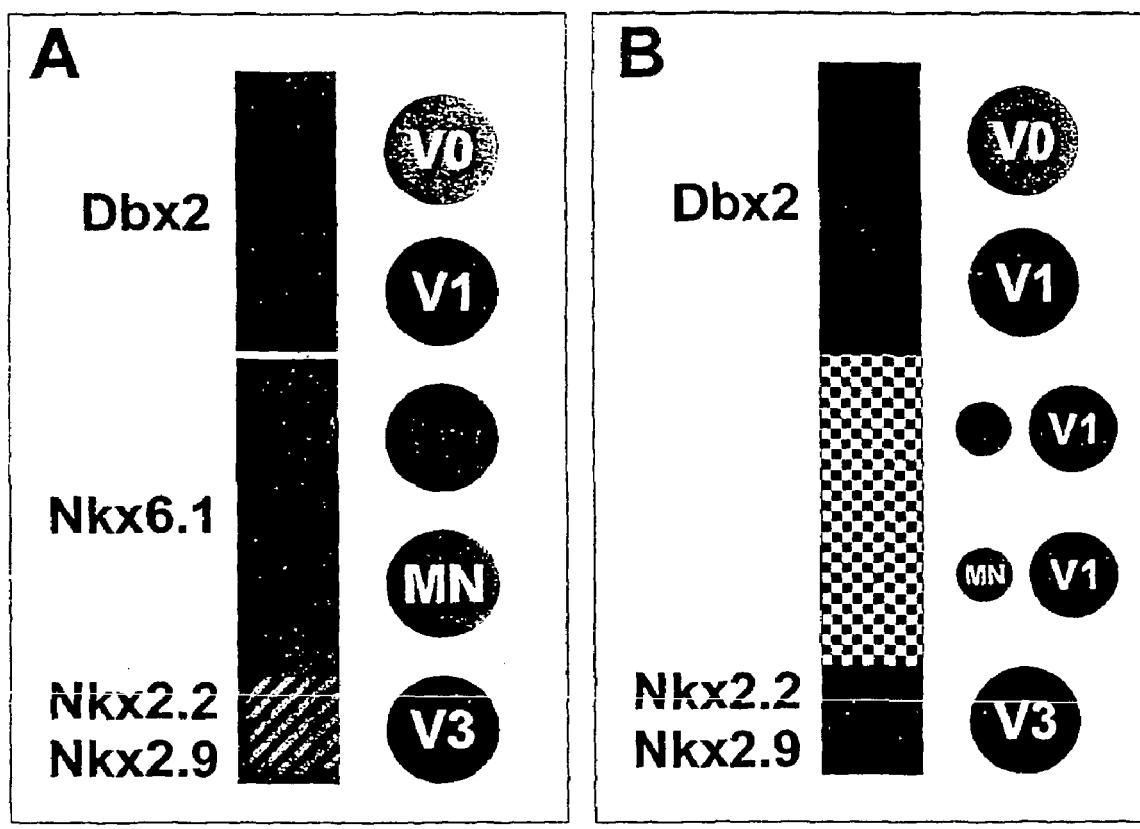
FIG. 5, see Sander et al., 2000).

Taken together, the findings herein reveal an essential role for the Nkx6.1 homeobox gene in the specification of regional pattern and neuronal fate in the ventral half of the mammalian CNS. Within the broad ventral domain within which Nkx6.1 is expressed (FIG. 5A), its activity is required to promote motor neuron and V2 interneuron generation and to restrict the generation of V1 interneurons (FIG. 5B). It is likely that the loss of motor neurons and V2 neurons is a direct consequence of the loss of Nkx6.1 activity, as the depletion of these two neuronal subtypes is evident at stages when only low levels of Dbx2 are expressed ectopically in most regions of the ventral neural tube. Nonetheless, it can not be excluded that low levels of ectopic ventral Dbx2 expression could contribute to the block in motor neuron generation. Consistent with this view, the ectopic expression of Nkx6.1 is able to induce both motor neurons and V2 neurons in chick neural tube (Briscoe et al. 2000). V3 interneurons and cranial visceral motor neurons derive from a set of Nkx6.1 progenitors that also express Nkx2.2 and Nkx2.9 (Briscoe et al. 1999, FIG. 5A). The generation of these two neuronal subtypes is unaffected by the loss of Nkx6.1 activity, suggesting that the actions of Nkx2.2 and Nkx2.9 dominate over that of Nkx6.1 within these progenitors. The persistence of some spinal motor neurons and V2 neurons in Nkx6.1 mutants could reflect the existence of a functional homologue within the caudal neural tube.

The role of Nkx6.1 revealed in these studies, taken together with previous findings, suggests a model in which the spatially restricted expression of Nkx genes within the ventral neural tube (FIG. 5) has a pivotal role in defining the identity of ventral cell types induced in response to graded Shh signaling. Strikingly, in Drosophila, the Nkx gene NK2 has been shown to have an equivalent role in specifying neuronal fates in the ventral nerve cord (Chu et al. 1998; McDonald et al. 1998). Moreover, the ability of Nkx6.1 to function as a repressor of the dorsally expressed Gsh1/2 homeobox genes parallels the ability of Drosophila NK2 to repress Ind, a Gsh1/2-like homeobox gene (Weiss et al. 1998). Thus, the evolutionary origin of regional pattern along the dorsoventral axis of the central nervous system may predate the divergence of invertebrate and vertebrate organisms.

REFERENCES

1. S. A. Anderson, D. D. Eisenstat, L. Shi, J. L. Rubenstein, *Science* 278:474-476 (1997).
2. S. Arber, B. Han, M. Mendelsohn, M. Smith, T. M. Jessell, S. Sockanathan, *Neuron* 23:659-674 (1999).
3. J. Briscoe, et al., *Nature* 398:622-627 (1999).
4. J. Briscoe et al., *Cell* 101:435-445 (2000).
5. J. D. Burrill, L. Moran, M. D. Goulding, H. Saueressig, *Development* 124:4493-4503 (1997).
6. H. Chu; C. Parras; K. White; F. Jimenez, *Genes & Dev.* 12:3613-3624 (1998).
7. J. Ericson, et al., *Cold Spring Harb. Symp. Quant. Biol.* 62:451-466 (1997a).
8. J. Ericson et al., *Cell* 87:661-673 (1996).
9. J. Ericson, et al., *Cell.* 90:169-180 (1997b).
10. M. D. Goulding et al., *EMBO J.* 10:1135-47 (1991).
11. M. Hammerschmidt, A. Brook, A. P. McMahon *Trends Genet.* 13:14-21 (1997)
12. M. Hebrok, S. K. Kim, D. A. Melton, *Genes & Dev.* 12:1705-1713 (1998).
13. A. Lumsden, R., and Krumlauf, R. *Science* 274: 1109-1115 (1996).
14. M. P. Matise, A. L. Joyner, *J. Neurosci.* 17:7805-7816 (1998).
15. J. A. McDonald, S. Holbrook, T. Isshiki, J. Weiss, C. Q. Doe, D. M. Mellerick. *Genes & Dev.* 12:3603-3612 (1998).
16. O. Pabst, H. Herbrand, H. H. Arnold, *Mech. Dev.* 73:85-93 (1998).
17. A. Pattyn, X. Morin, H. Cremer, C. Goridis, J. F. Brunet, *Development* 124:4065-4075 (1997).
18. A. Pierani, S. Brenner-Morton, C. Chiang, T. M. Jessell, *Cell* 97:903-915 (1999).
19. M. Qiu, K. Shimamura, L. Sussel, S. Chen, J. L. Rubenstein, *Mech. Dev.* 72:77-88 (1998).
20. J. L. Rubenstein and Beachy, P. A. *Curr. Opin. Neurobiol.* 8:18-26 (1998).
21. J. L. Rubenstein et al., *Annu Rev Neurosci.* 21:445-477 (1998).
22. Sander, M. et al. *Keystone symposium on vertebrate development.* Steamboat Springs, Colo. (1998).
23. Schaeren-Wiemers, N. and Gerlin-Moser, A. *Histochemistry* 100:431-440 (1993).

24. Sockanathan, S. and Jessell, T. M. *Cell* 94:503-514 (1998).
25. L. Sussel, O. Marin, S. Kimura, J. L. Rubenstein, *Development* 126:3359-3370 (1999).
26. Y. Tanabe, and T. M. Jessell, *Science* 274:1115-23 (1996).
27. J. Thaler et al., *Neuron* 23:675-687 (1999).
28. T. Tsuchida, et al., *Cell* 79:957-970 (1994).
29. M. T. Valerius, H. Li, J. L. Stock, M. Weinstein, S. Kaur, G. Singh, S. S. Potter, *Dev. Dyn.* 203:337-51 (1995).
30. J. B. Weiss, T. Von Ohlen, D. M. Mellerick, G. Dressler, C. Q. Doe, M. P.Scott, *Genes & Dev.* 12:3591-3602 (1998).

Second Series of Experiments

Introduction

During the development of the vertebrate central nervous system, the assignment of regional identity to neural progenitor cells has a critical role in directing the subtype identity of post-mitotic neurons. Within the ventral half of the neural tube, the specification of progenitor cell identity is initiated by the long-range signalling activity of the secreted factor, Sonic hedgehog (Shh) (Briscoe et al., 2001; Briscoe and Ericson, 2001). Shh signaling appears to establish ventral progenitor cell identities by regulating the spatial pattern of expression of homeodomain transcription factors of the Nkx, Pax, Dbx and Irx families (Ericson et al., 1997; Pierani et al., 1999; Briscoe et al., 2000). Members of all four gene families have been duplicated during evolution (Shoji et al., 1996; Wang et al., 2000; Hoshiyama et al., 1998, Peters et al., 2001), and the resulting homeodomain protein pairs are typically expressed in overlapping or nested domains within the neural tube (Briscoe and Ericson, 2001). Some of these homeodomain protein pairs have been proposed to have distinct, and others redundant, roles in spinal cord patterning (Mansouri and Gruss, 1998; Briscoe et al., 1999; Pierani et al., 2001), but the impact of such homeobox gene duplication on neuronal diversification has not been explored directly.

One unifying feature of this diverse array of progenitor homeodomain proteins is their subdivision into two general groups, termed class I and II proteins, on the basis of their mode of regulation by Shh signalling (Briscoe and Ericson, 2001). The class I proteins are constitutively expressed by neural progenitor cells, and their expression is repressed by Shh signaling, whereas neural expression of the class II proteins requires exposure to Shh (Ericson et al., 1997; Qiu et al., 1998; Briscoe et al., 1999; 2000; Pabst et al., 2000). Although the spatial pattern of expression of the class I proteins has revealed the existence of five ventral progenitor domains, class II proteins have been identified for only two of these domains (Briscoe et al., 2000), raising questions about the existence and identity of additional class II proteins. There is, however, emerging evidence that the combination of class I and II proteins that is expressed by neural progenitor cells directs the fate of their neuronal progeny. In support of this, misexpression of individual progenitor homeodomain proteins in the chick neural tube promotes the ectopic generation of neuronal subtypes, with a specificity predicted by the normal profile of progenitor homeodomain protein expression (Briscoe et al., 2000; Pierani et al., 2001). Conversely, the analysis of mouse mutants has provided genetic evidence that the activities of specific class I and II proteins are required to establish progenitor cell domains and to direct ventral neuronal fates (Ericson et al., 1997; Briscoe et al., 1999; Sander et al., 2000; Pierani et al., 2001).

The participation of progenitor homeodomain proteins in the conversion of graded Shh signals into all-or-none distinctions in progenitor cell identity depends on cross-repressive interactions between selected pairs of class I and II protein (Ericson et al., 1997; Briscoe et al., 2000; Sander et al., 2000; Muhr et al., 2001). In addition, most class I and II proteins have been shown to function directly as transcriptional repressors, through the recruitment of corepressors of the Gro/TLE class (Muhr et al., 2001). These findings have suggested a derepression model of neural patterning which invokes the idea that the patterning activities of individual class I or II proteins are achieved primarily through their ability to repress expression of complementary homeodomain proteins from specific progenitor domains. A central implication of this model is that homeodomain proteins direct progenitor cells to individual neuronal fates by suppressing alternative pathways of differentiation—a view that has strong parallels with proposed mechanisms of lineage restriction during lymphoid differentiation (Nutt et al., 1999; Rolink et al., 1999; Eberhard, et al., 2000).

Much of the evidence that has led to this general outline of ventral neural patterning has emerged from an analysis of members of the Nkx gene family. Two closely-related Nkx repressor proteins, Nkx2.2 and Nkx2.9, function as class II proteins that specify the identity of V3 neurons (Ericson et al., 1997; Briscoe et al., 1999, 2000). A more distantly related class II repressor protein, Nkx6.1, is expressed throughout the ventral third of the neural tube and when ectopically expressed, can direct motor neuron and V2 neuron fates (Briscoe et al., 2000; Sander et al., 2000). These gain-of-function studies are supported by an analysis of mice lacking Nkx6.1 function, which exhibit a virtually complete failure in V2 interneuron generation (Sander et al., 2000). Nkx6.1 null mice also show a reduction in motor neuron generation at rostral levels of the spinal cord, but at more caudal levels motor neurons are formed in near-normal numbers (Sander et al., 2000). This observation reveals the existence of an Nkx6.1-independent program of spinal motor neuron generation, although the molecular basis of this alternative pathway is unclear.

A close relative of Nkx6.1, termed Nkx6.2 (also known as Nkx6B or Gtx), has been identified (Komuro et al., 1993; Lee et al., 2001), and is expressed by neural progenitor cells (Cai et al., 1999). In its alias of Gtx, Nkx6.2 has been suggested to regulate myelin gene expression (Komuro et al., 1993), but its possible functions in neural patterning have not been examined. The identification of an Nkx6 gene pair prompted us to address three poorly resolved aspects of ventral neural patterning. First, do closely related pairs of repressor homeodomain proteins serve distinct or redundant roles in ventral neural patterning? Second, are class I repressor proteins always complemented by a corresponding class II repressor, and if so, is Nkx6.2 one of the missing class II proteins? Third, to what extent is the generation of spinal motor neurons dependent on the activity of Nkx6 class proteins?

To address these issues we mapped the profile of expression of Nkx6.2 and Nkx6.1 during neural tube development, and analysed mouse Nkx6 mutants to determine the respective contributions of these two genes to neural patterning. We show that Nkx6.2, like Nkx6.1, functions as a class II repressor homeodomain protein. Our analysis of Nkx6 mutants further indicates that the duplication of an ancestral Nkx6 gene has resulted in the expression of two proteins that exert markedly different levels of repressor activity in the ventral neural tube. This differential repressor activity of these two proteins appears to provide both a fail-safe mechanism during motor neuron generation, and the potential for enhanced diversification of ventral interneuron subtypes. Moreover, we find that under conditions of reduced Nkx6 gene dosage, ventral neuronal subtypes can be generated from progenitor cells that lack the class I or class II proteins normally required for their generation. This finding supports one of the central tenets of the derepression model of ventral neural patterning—that progenitor homeodomain proteins direct particular neuronal fates by actively suppressing cells from adopting alternative fates.

The specification of neuronal fate in the vertebrate central nervous system appears to depend on the profile of transcription factor expression by neural progenitor cells, but the precise roles of such factors in neurogenesis remain poorly understood. A pair of closely-related homeodomain proteins that function as transcriptional repressors, Nkx6.2 and Nkx6.1, are expressed by progenitor cells in overlapping domains of ventral spinal cord. We provide genetic evidence in the mouse that differences in the level of repressor activity of homeodomain proteins underlies the diversification of ventral interneuron subtypes, and provides a fail-safe mechanism during motor neuron generation. We also show that a reduction in Nkx6 protein activity permits V0 neurons to be generated from progenitor cells that lack the homeodomain proteins normally required for their generation. This finding provides direct evidence for a model of neuronal fate specification in which progenitor homeodomain proteins direct specific neuronal fates by actively suppressing the expression of transcription factors that direct alternative fates.

Experimental Details

A. Materials and Methods

Generation of Nkx6.2 Mutant Mice

Mouse Nkx6.2 genomic clones were isolated from a 129/Ola mouse genomic library. A targeting construct was constructed by inserting a tau-lacZ/pGKneo cassette into a 5 kb 5' HindIII-NcoI fragment and a 2.7 kb 3' SphI-AccI fragment. The linearized targeting construct was electroporated into E14.1 (129/Ola) ES cells. Cells were selected with G418 and screened by Southern blot analysis using a 200 bp 3' AccI fragment, which detected a 6 kb wild type band and a 2.9 kb mutant band. Recombinant clones were injected into C57BL/6J blastocysts to generate two chimeric founders, both of which transmitted the mutant allele. Mice homozygous for the mutant alleles were born at Mendelian frequency and survived through adulthood. All experiments involved mice maintained on a C57BL/6 background. The generation and genotyping of Nkx6.1 mutant mice have been described previously (Sander et al. 2000). Compound Nkx6 mutant mice were obtained by crossing Nkx6.2$^{+/tlz}$; Nkx6.1$^{+/-}$ double heterozygous mice. Genotyping was performed using Southern blot analysis.

Chick in Ovo Electroporation

Mouse Nkx6.2 was isolated by PCR (Komuro et al., 1993) and chick Nkx6.2 from a chick spinal cord library (Basler et al., 1993) using mouse Nkx6.1 and Nkx6.2 as probes. cDNAs encoding full-length mouse and chick Nkx6.2 were inserted into a RCASBP(B) retroviral vector and electroporated into the neural tube of stage HH (Hamburger and Hamilton, 1953) 10-12 chick embryos (Briscoe et al., 2000). After 24-48 h, embryos were fixed and processed for immunohistochemistry.

Immunohistochemistry and In Situ Hybridization Histochemistry

Immunohistochemical localization of proteins was performed as described (Yamada et al., 1993; Briscoe et al., 2000). Guinea-pig antisera were generated against an 11 amino acid N-terminal sequence of mouse Nkx6.2. Other antibodies used were rabbit anti-Lim3 (Ericson et al. 1997), mAb Hb9 (Tanabe et al., 1998), rabbit anti-Isl1/2 (Tsuchida et al., 1994), rabbit anti-Chx10 (Ericson et al., 1997), rabbit anti-En1 (Davis et al., 1991), mAb anti-Evx1/2, rabbit anti-Dbx1, rabbit anti-Dbx2 (Pierani et al., 1999), rabbit anti-Nkx6.1 (Jörgensen et al., 1999), mAb anti-Pax7 (Ericson et al., 1996), rabbit anti-bgal (Cappel) and goat anti-bgal (Biogeneseis). Images were collected on a Zeiss LSM510 confocal microscope. In situ hybridisation was performed as described (Schaeren-Wiemers and Gerfin-Moser, 1993), using chick probes for Dbx1, Dbx2 (Pierani et al., 1999), Nkx6.1 (Briscoe et al., 2000) and Nkx6.2. A mouse probe for the 5'UTR of Nkx6.2 comprised 346 bp upstream of the start ATG site. Whole-mount X-gal staining was performed as described (Mombaerts et al., 1996).

B. Results

Distinct Patterns of Nkx6.1 and Nkx6.2 Expression in Embryonic Spinal Cord

Figure 10:
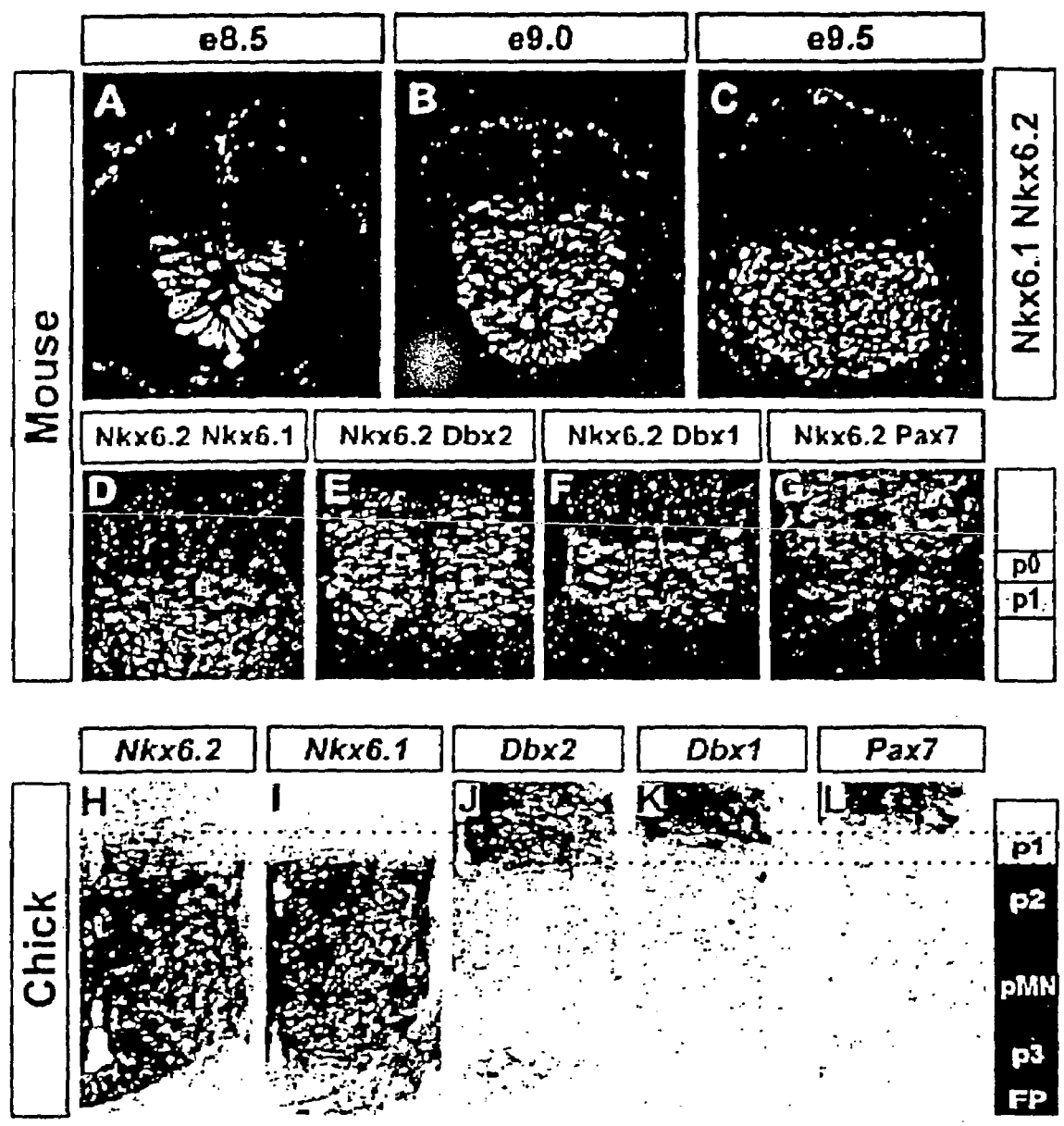
FIG. 10 expression of Nkx6.2 and Nkx6.1 in developing mouse and chick spinal cord. (A) At e8.5, Nkx6.2 and Nkx6.1 are expressed in a broad ventral domain of the mouse neural tube. (B) At e9.0, Nkx6.2 expression is largely confined to a narrow domain immediately dorsal to the domain of Nkx6.1 expression. A few scattered cells that co-express Nkx6.2 and Nkx6.1 are detected in more ventral positions at this stage. (C) At e9.5, Nkx6.2 is expressed in a narrow domain, dorsal to the Nkx6.1 boundary. (D-G) Comparative patterns of expression of Nkx6.2, Nkx6.1, Dbx2, Dbx1 and Pax7 in the intermediate region of e10.5 mouse spinal cord. (H-L) Expression pattern of Nkx6.2, Nkx6.1, Dbx2, Dbx1 and Pax7 in HH stage 20 chick spinal cord. Panels on right indicate progenitor domains, defined according to Briscoe et al., 2000.

To examine the roles of Nkx6 class genes in ventral neuronal specification we compared the patterns of expression of Nkx6.2 and Nkx6.1 with that of other progenitor homeodomain proteins in the spinal cord of mouse and chick embryos. In the caudal neural tube of the mouse, the expression of Nkx6.2 was first detected at ~e8.5, in a broad ventral domain that largely coincided with that of Nkx6.1 (FIG. 10A). Between e8.5 and e9.5, the expression of Nkx6.2 was lost from most Nkx6.1$^+$ cells in the ventral neural tube, although expression persisted in a narrow stripe of cells just dorsal to the limit of Nkx6.1 expression (FIG. 10B, C). At e10.0-e10.5, virtually all, Nkx6.2$^+$ cells coexpressed Dbx2 (FIG. 10E), and the ventral limit of expression of both Nkx6.2 and Dbx2 coincided with the dorsal limit of Nkx6.1 expression at the p1/p2 domain boundary (FIG. 10D, E). Nkx6.2 was expressed predominantly within the p1 domain, but scattered Nkx6.2$^+$ cells were detected within the p0 domain—the domain of expression of Pax7$^-$, Dbx1$^+$ cells (FIG. 10F). Within the p0 domain, however, individual Nkx6.2$^+$ cells did not coexpress Dbx1, although they did express Dbx2 (FIGS. 10E-G). Thus, the scattered Nkx6.2$^+$ cells found at the dorsoventral level of the p0 domain exhibit a p1, rather than p0, progenitor cell identity. Studies in chick have similarly shown that p0 and p1 progenitors are interspersed in the most dorsal domain of the ventral neural tube (Pierani et al., 1999).

In the chick neural tube, as in the mouse, Nkx6.1 and Nkx6.2 are initially coexpressed in a broad ventral domain (Cai et al., 1999; data not shown). But in contrast to the mouse, Nkx6.2 expression persists in ventral progenitor cells, with the consequence that the expression of Nkx6.2 and Nkx6.1 also overlaps at later developmental stages (FIG. 10H, I). Nevertheless, expression of chick Nkx6.2 is also detected in a thin stripe of cells dorsal to the limit of Nkx6.1 expression, within the p1 domain (FIG. 10H). Thus, in both species, p1 progenitors coexpress Nkx6.2 and Dbx2 and exclude Nkx6.1.

Nkx6.2 Regulates V0 and V1 Interneuron Fates by Repression of Dbx1 Expression

The establishment and maintenance of progenitor cell domains in the ventral neural tube has been proposed to depend on mutual repressive interactions between complementary pairs of class I and II homeodomain proteins (Briscoe et al., 2000; Muhr et al., 2001). But class II proteins have been identified for only two of the five known progenitor domain boundaries (the p1/p2 and pMN/p3 boundaries) (Ericson et al., 1997; Briscoe et al., 1999, 2000; Sander et al., 2000). The mutually exclusive pattern of expression of Nkx6.2 and Dbx1 within p1 and p0 progenitors led us to consider whether Nkx6.2 might function as a class II protein that represses Dbx1 expression, and thus help to establish the identity of p1 progenitor cells and the fate of their En1$^+$ V1 neuronal progeny.

Figure 11:
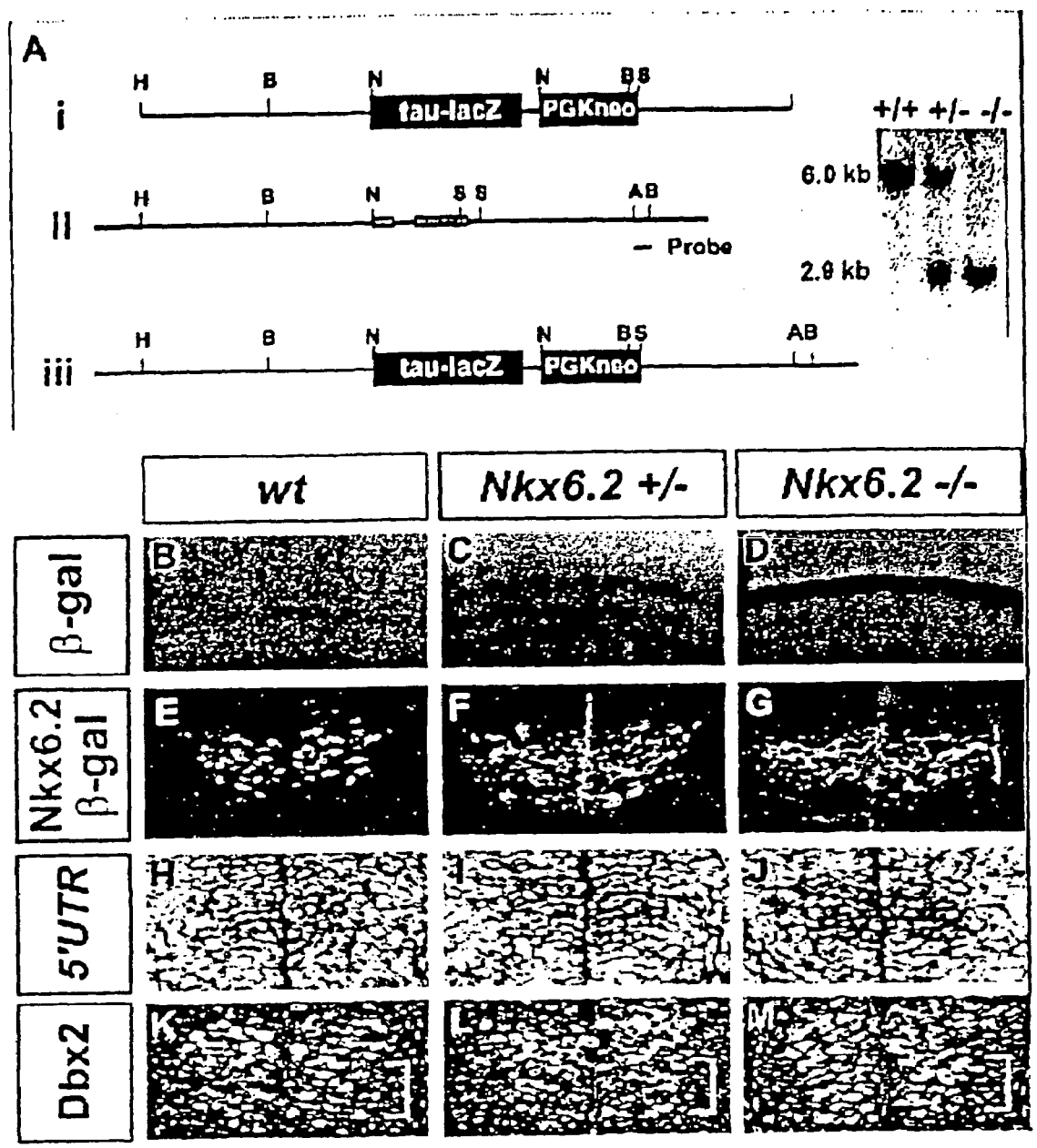
FIG. 11 elevation in Nkx6.2 and Dbx2 expression in p1 domain cells in Nkx6.2 mouse mutants. (A) Diagram of the targeting construct (i) used to replace the coding sequence of Nkx6.2 (ii) with a tau-lacZ PGK-neo cassette (iii). Red bar indicates region used as probe in genotyping. (B-D) Sagital view of e10.5 spinal cord showing LacZ expression, detected by X-gal staining, in wild type (wt) (B) Nkx6.2$^{+/tlz}$ (C) and Nkx6.2$^{tlz/tlz}$ (D) embryos. (E-G) Nkx6.2 and LacZ expression in the p1 domain of wt (E), Nkx6.2$^{+/tlz}$ (F), and Nkx6.2$^{tlz/tlz}$ (G) embryos at e10.5. (H-J) In situ hybridization with a 5'-UTR probe shows that expression of Nkx6.2 is elevated in the p1 domain of Nkx6.2$^{tlz/tlz}$ embryos (J), compared with wt (H) or Nkx6.2$^{+/tlz}$ (I) embryos. (K-M) Expression of Dbx2 is up regulated ~2- fold in cells within the p1 domain (yellow bracket) in Nkx6.2$^{tlz/tlz}$ embryos (M), compared with wt (K), or Nkx6.2$^{+/tlz}$ (L) embryos. Abbreviations in (A): H=HindIII, B=BamHI, N=NcoI, S=SphI, A=AccI.

To test this idea, we analysed the profile of expression of class I and II homeodomain proteins in Nkx6.2 mutant embryos. We inactivated the mouse Nkx6.2 gene by homologous recombination in embryonic stem (ES) cells. A targeted Nkx6.2 allele (Nkx6.2$^{tlz}$) was generated by replacing the coding sequence of Nkx6.2 with a tauLacZ cassette (FIG. 11A). In the spinal cord of Nkx6.2$^{+/tlz}$ embryos analysed at e10.5, expression of LacZ and Nkx6.2 coincided within the p1 progenitor domain (see FIG. 1E, F). In Nkx6.2$^{tlz/tlz}$ embryos, the location of LacZ$^+$ cells was also similar to that in Nkx6.2$^{+/tlz}$ embryos (FIG. 11F, G), but Nkx6.2 protein was not detected (FIG. 11G). These data provide evidence that the Nkx6.2$^{tlz}$ allele generates a null mutation, and that disruption of the Nkx6.2 locus does not perturb the normal spatial pattern of expression of this gene.

We did observe, however, that the level of LacZ expression was markedly elevated in Nkx6.2$^{tlz/tlz}$, when compared with Nkx6.2$^{+/tlz}$, embryos (FIGS. 11B-D). An elevation in level of expression of the residual 5' Nkx6.2 transcript was also detected in Nkx6.2$^{tlz/tlz}$ embryos (FIGS. 11H-J). These observations provide evidence that Nkx6.2 negatively regulates its own expression level within p1 progenitor cells.

Figure 12:
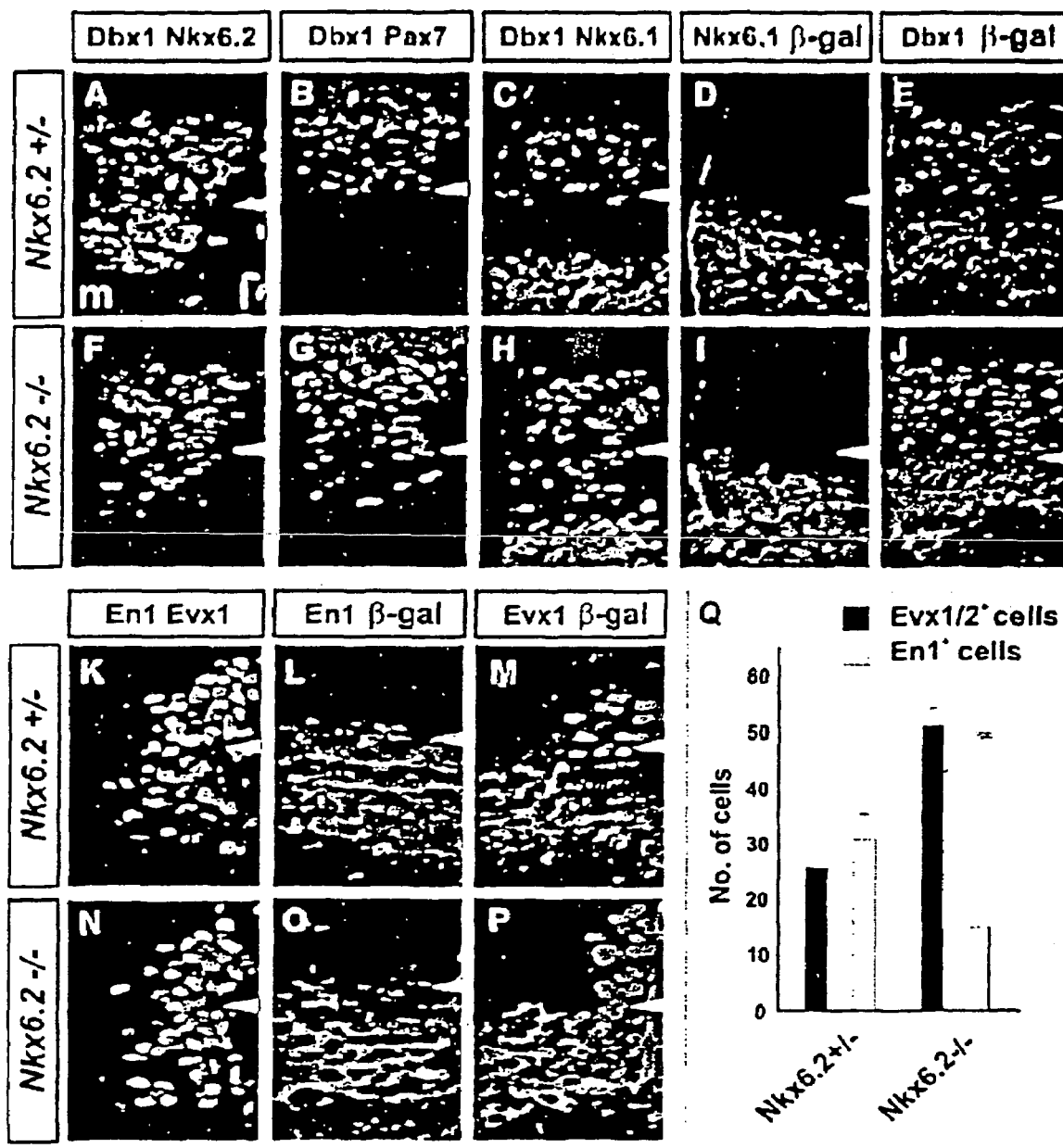
FIG. 12 a partial switch from V1 to V0 neuronal fate in Nkx6.2 mutant mice. (A-E) Expression of Nkx6.2 (A), Nkx6.1 (C, D), Dbx1 (B, C, E), and Pax7 (B) appears normal at caudal hindbrain levels of e10.5 Nkx6.2$^{+/tlz}$ embryos. The expression of Nkx6.1 (D) and Dbx1 (E) abuts the ventral and dorsal boundaries of LacZ expression.(F-J) In e10.5 Nkx6.2$^{tlz/tlz}$ embryos, expression of Nkx6.1 (H, I) and Pax7 (G) is unchanged but expression of Dbx1 (F, G, H) is expanded ventrally into the p1 domain. Many ventral ectopic Dbx1$^+$ cells in Nkx6.2$^{tlz/tlz}$ embryos express LacZ (J). (K-M) Evx1/2$^+$ V0 neurons are generated dorsal to En1$^+$ V1 neurons (K) and LacZ$^+$ cells (M) in Nkx6.2$^{+/tlz}$ embryos. En1$^+$ neurons express LacZ in Nkx6.2$^{+/tlz}$ (L) and Nkx6.2$^{tlz/tlz}$ (O) embryos. (N-P) Evx1/2$^+$ V0 neurons are generated in increased numbers and at ectopic ventral positions in the caudal hindbrain of Nkx6.2$^{tlz/tlz}$ embryos. (N) The number of En1$^+$ V1 neurons is reduced and the remaining En1$^+$ neurons are intermingled with ectopic Evx1/2$^+$ cells. (P) Many Evx1/2$^+$ neurons in Nkx6.2$^{tlz/tlz}$ embryos co-express LacZ. (Q) Quantitation of Evx1/2$^+$ V0, and En1$^+$ V1, neurons at the caudal hindbrain of Nkx6.2$^{+/tlz}$ and Nkx6.2$^{tlz/tlz}$ embryos at e10.5. Counts from 12 sections, mean+S.D. In panels (A-P), the white arrowhead indicates the p0/p1 boundary.

We next analysed the pattern of expression of class I and II homeodomain proteins in the spinal cord and caudal hindbrain of Nkx6.2$^{+/tlz}$ embryos. The domains of expression of the class II proteins Nkx2.2 and Nkx6.1, and of the class I proteins Pax7, Dbx2, Irx3 and Pax6 were similar in Nkx6.2$^{tlz/tlz}$, Nkx6.2$^{+/tlz}$, and wild type embryos (FIGS. 12B-D, G-I; data not shown). In addition, normal patterns of expression of Dbx2 and Nkx6.1 were detected at the p1/p2 domain boundary (data not shown), showing that establishment of the p1 progenitor domain does not require Nkx6.2 function. However, the level of Dbx2 expression in p1 domain progenitors was increased ~two-fold in Nkx6.2$^{tlz/tlz}$ mutants (FIGS. 11K-M), indicating that Nkx6.2 normally limits the level of Dbx2 expression in this domain.

Figure 15:
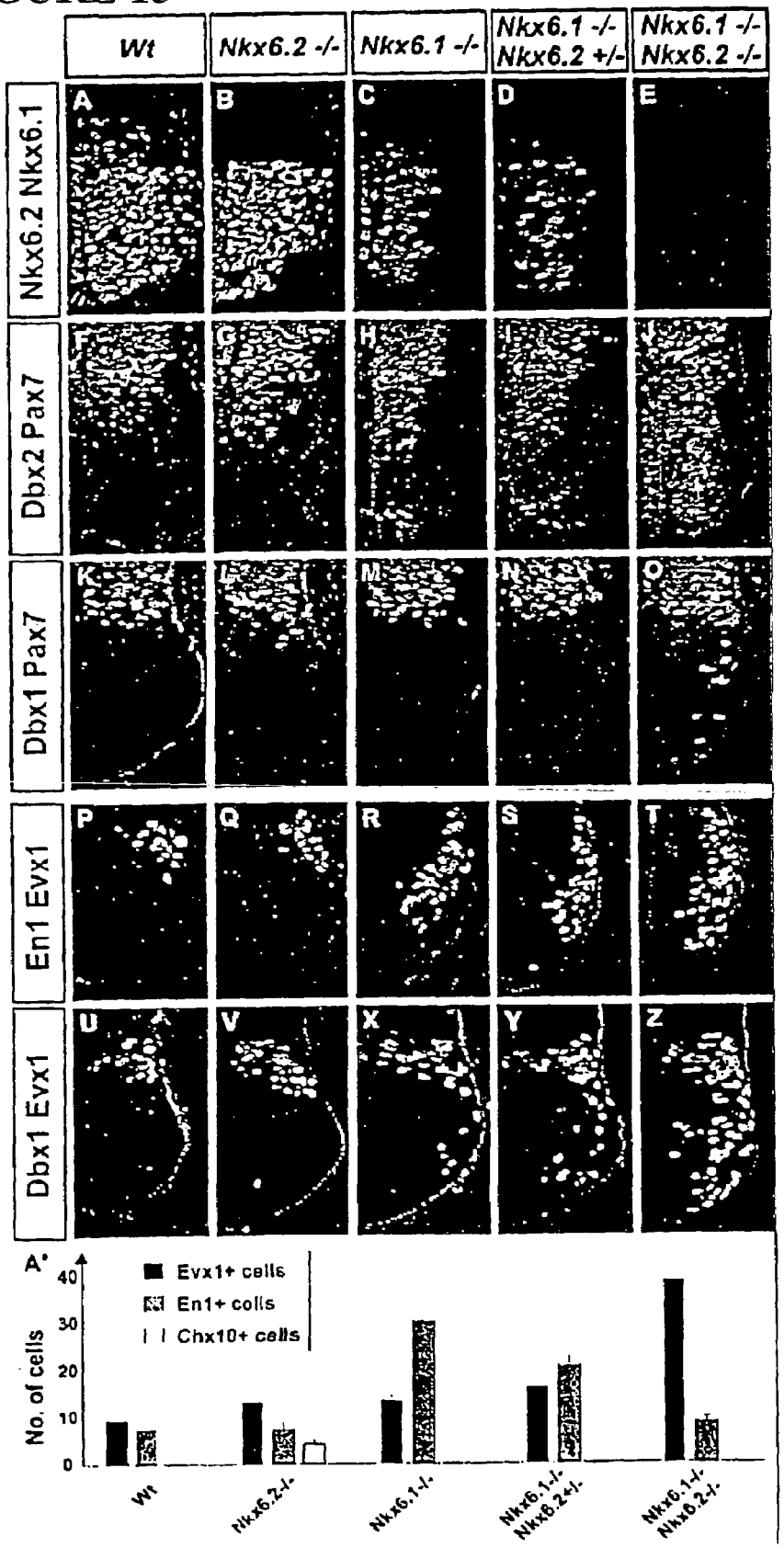
FIG. 15 changes in class I protein expression and ventral interneuron generation in Nkx6 mutants. (A-E) Expression of Nkx6.1 and Nkx6.2 in the spinal cord in different Nkx6 mutant backgrounds at e10.5. (F-J) Spatial patterns of Pax7 and Dbx2 expression in different Nkx6 mutant backgrounds. Note that the level of Dbx2 expression in the pMN domain of Nkx6.1$^{-/-}$; Nkx6.2$^{+/tlz}$ is very low, implying the existence of a pMN domain restricted gene that has the capacity to repress Dbx2 expression. Recent studies have provided evidence that the bHLH protein Olig2 possesses these properties (Novitch et al., 2001).

We also detected a marked change in the pattern of expression of the p0 progenitor cell marker Dbx1 in Nkx6.2$^{tlz/tlz}$ embryos. At caudal hindbrain levels, the number of ventral Dbx1$^+$ progenitor cells increased 1.7- fold (FIG. 12F), and the domain of Dbx1$^+$ cells expanded ventrally, extending through the p1 domain to the dorsal limit of Nkx6.1 expression (FIG. 12H). Moreover, in Nkx6.2$^{tlz/tlz}$ embryos all of the ectopic Dbx$^+$ cells found within the p1 domain coexpressed LacZ (FIG. 12J). Thus, many progenitors within the p1 domain initiate Dbx1 expression in the absence of Nkx6.2 function. Nevertheless in Nkx6.2$^{tlz/tlz}$ embryos, numerous LacZ$^+$ progenitors still lacked Dbx1 expression (FIG. 12J), implying the existence of an Nkx6.2-independent means of excluding Dbx1 expression from p1 progenitors. The ventral expansion of Dbx1 was most prominent at caudal hindbrain and cervical spinal levels of the neural tube but a similar, albeit less marked, expansion of Dbx1 expression was detected at caudal spinal levels (data not shown; see FIG. 15). Taken together, these data imply that within p1 domain progenitors Nkx6.2 functions as a weak repressor of Dbx2 expression and a more potent repressor of Dbx1 expression.

We next analysed the generation of interneuron subtypes in the ventral neural tube. In wild type embryos, Dbx1$^+$, Dbx2$^+$, Nkx6.2$^-$ p0 progenitors generate Evx1/2$^+$ V0 neurons (Pierani et al., 1999; 2001); Nkx6.2$^+$, Dbx1$^-$, Dbx2$^+$ p1 progenitors give rise to En1$^+$ V1 neurons (Burrill et al., 1997; Ericson et al., 1997), and Nkx6.1$^+$, Irx3$^+$, p2 progenitors give rise to Chx10$^+$ V2 neurons (Ericson et al., 1997; Briscoe et al., 2000). Dbx1 activity in p0 progenitors is required to promote V0 and suppress V1 neuronal fates (Pierani et al., 2001). The ventral expansion in Dbx1 expression in Nkx6.2$^{tlz/tlz}$ embryos therefore led us to examine whether the loss of Nkx6.2 function leads progenitor cells within the p1 domain to adopt a V0 rather than V1 neuronal fate.

Figure 14:
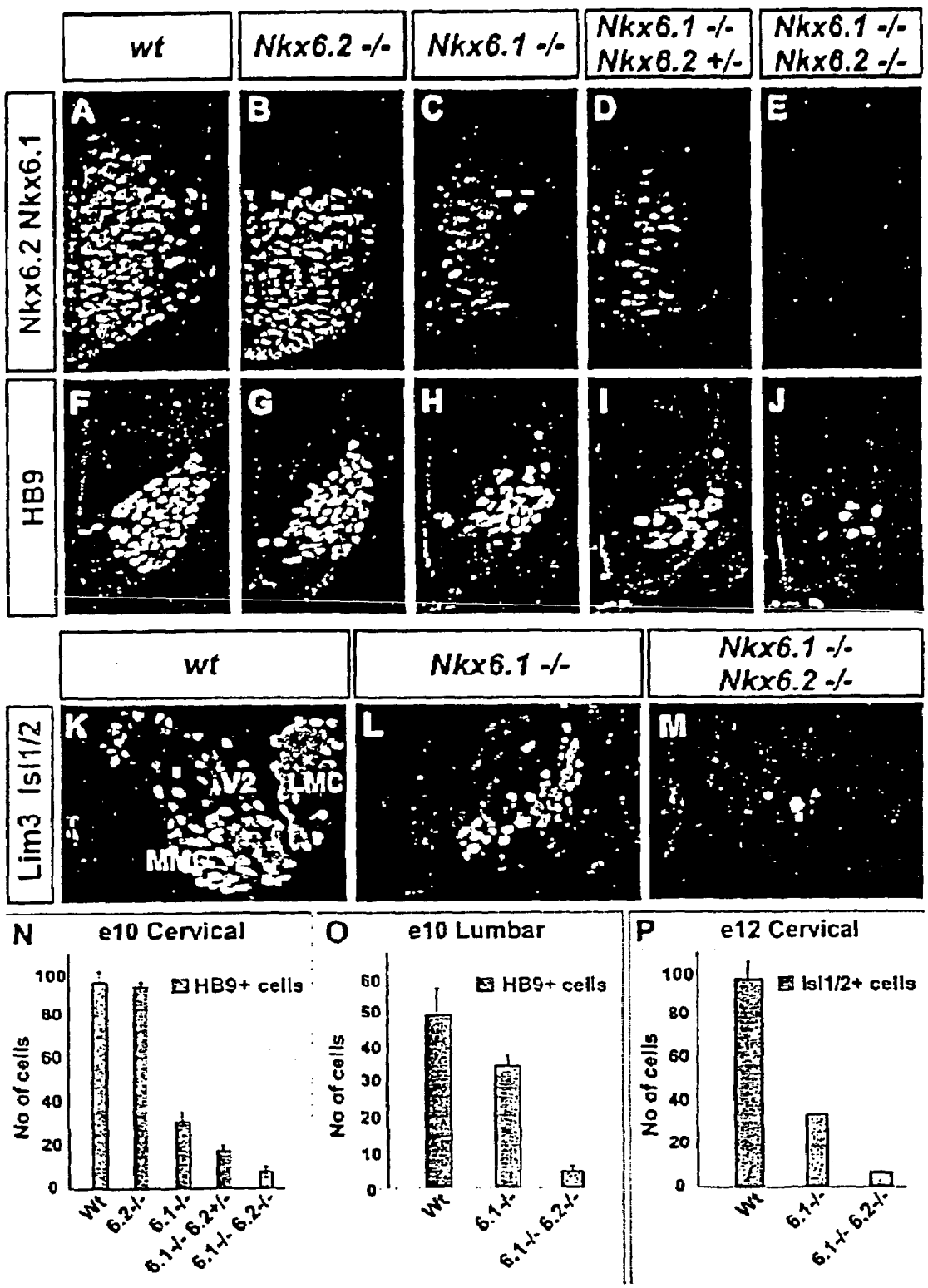
FIG. 14 the deregulated expression of Nkx6.2 underlies motor neuron generation in Nkx6.1 mutants. (A) In e10.5 wt embryos, Nkx6.2 expression is confined to the p1 domain and Nkx6.1 is expressed in the p2, pMN and p3 domains. (B) No change in the expression of Nkx6.1 is detected in Nkx6.2$^{tlz/tlz}$ embryos. (C, D) In Nkx6.1$^{-/-}$ and Nkx6.1$^{-/-}$; Nkx6.2$^{+/tlz}$ embryos, Nkx6.2 expression is derepressed in the p2, pMN and p3 domains. (E) No expression of Nkx6.2 or Nkx6.1 protein is detected in Nkx6.1$^{-/-}$; Nkx6.2$^{tlz/tlz}$ embryos. (F, G) HB9$^+$, Isl1/2$^+$ motor neurons are generated in normal numbers in Nkx6.2$^{tlz/tlz}$ embryos. The number of motor neurons is reduced by ~60% in Nkx6.1$^{-/-}$ embryos (H), by ~80% in Nkx6.1$^{-/-}$; Nkx6.2$^{+/tlz}$ embryos (I) and by >90% in Nkx6.1$^{-/-}$; Nkx6.2$^{tlz/tlz}$ at cervical levels of e10.5 spinal cord (J). (K-M) At e12, the number of motor neurons of medial (MMC) (Isl1$^+$, Lim3$^+$) and lateral (LMC) (Isl1[30]) subtype identity is reduced in similar proportions in Nkx6.1$^{-/-}$ and Nkx6.1$^{-/-}$; Nkx6.2$^{tlz/tlz}$ embryos. Lim3$^+$ V2 neurons are missing in Nkx6.1$^{-/-}$ embryos and Nkx6.1$^{-/-}$; Nkx6.2$^{tlz/tlz}$ embryos at this stage. (N-P) Quantitation of HB9$^+$ and Isl1/2$^+$ motor neurons at cervical and lumbar levels in wt, Nkx6.2 and Nkx6.1 single mutants and in Nkx6.2; Nkx6.1 compound mutants at e10 and e12. Counts from 12 sections, mean+S.D.

In the caudal hindbrain of Nkx6.2$^{tlz/tlz}$ embryos examined at e10.5, we detected a ~two-fold increase in the number of Evx1/2$^+$ V0 neurons and the domain of V0 neuronal generation expanded ventrally the normal position of the p1 domain (FIG. 12N). Consistent with this, many Evx1/2$^+$ neurons coexpressed LacZ (FIG. 12P), showing directly that some V0 neurons derive from p1 progenitors in the absence of Nkx6.2 function. Conversely, the total number of En1$^+$ V1 neurons generated in Nkx6.2$^{tlz/tlz}$ embryos was reduced by ~50% (FIG. 12Q). The dorsoventral position of generation of the remaining En1$^+$ V1 neurons was similar in Nkx6.2$^{tlz/tlz}$ embryos (FIG. 12N), and these neurons expressed LacZ (FIG. 12O) showing directly that Nkx6.2$^+$, Dbx2+ p1 progenitor cells generate V1 neurons. The total number of neurons generated from p1 domain progenitors, defined by Cyn1, TuJ1 and Lim1/2 expression was similar in Nkx6.2$^{tlz/tlz}$ and Nkx6.2$^{+/tlz}$ embryos examined at e10.5 (data not shown). In addition, the number of TUNEL$^+$ cells was similar in Nkx6.2$^{tlz/tlz}$ and Nkx6.2$^{+/tlz}$ embryos (data not shown). Chx10$^+$ V2 neurons and HB9$^+$, Isl1/2$^+$ motor neurons were present in normal numbers and positions in Nkx6.2$^{tlz/tlz}$ embryos (FIG. 14; data not shown). Together, these findings show that the activity of Nkx6.2 within p1 progenitors promotes V1 neuronal generation and helps to suppress the generation of V0 neurons, a finding consistent with the proposed role of Nkx6.2 in repressing Dbx1 expression from p1 progenitors.

Repression of Nkx6.2 by Nkx6.1 Underlies Nkx6 Gene Redundancy in Spinal Motor Neuron Generation We next addressed the respective contributions of Nkx6.1 and Nkx6.2 to motor neuron and V2 neuron generation. In the ventral neural tube, p2 and pMN progenitors express Nkx6.1 and give rise to V2 neurons and motor neurons respectively. Ectopic expression of Nkx6.1 is sufficient to induce motor neurons and V2 interneurons in dorsal regions of the neural tube, and in Nkx6.1 mutant mice V2 neurons are eliminated (Briscoe et al., 2000; Sander et al., 2000). Nevertheless, there is only a partial reduction in motor neuron generation in Nkx6.1 mutants (Sander et al., 2000), revealing the existence of an Nkx6.1-independent pathway of motor neuron generation. Nkx6.2 does not normally contribute to motor neuron specification in the mouse, since its expression is extinguished from ventral progenitors well before the appearance of post-mitotic motor neurons (FIGS. 10A-C), and there is no change in the number of motor neurons generated in Nkx6.2$^{tlz/tlz}$ embryos (see FIG. 14G).

Three lines of evidence, however, led us to consider a cryptic role for Nkx6.2 in motor neuron generation. First, Nkx6.2 and Dbx2 share the same ventral limit of expression at the p1/p2 domain boundary, and the expression of Dbx2 is repressed by Nkx6.1 (Briscoe et al., 2000; Sander et al., 2000). Second, Nkx6.2 negatively regulates its own expression level within p1 domain progenitors (FIG. 11D, G, J). Third, Nkx6.1 and Nkx6.2 possess similar Gro/TLE recruitment activities and DNA target site binding specificities (Muhr et al., 2001). We reasoned therefore that under conditions in which Nkx6.1 activity is reduced or eliminated, Nkx6.2 expression might be derepressed in p2 and pMN progenitors.

Figure 13:
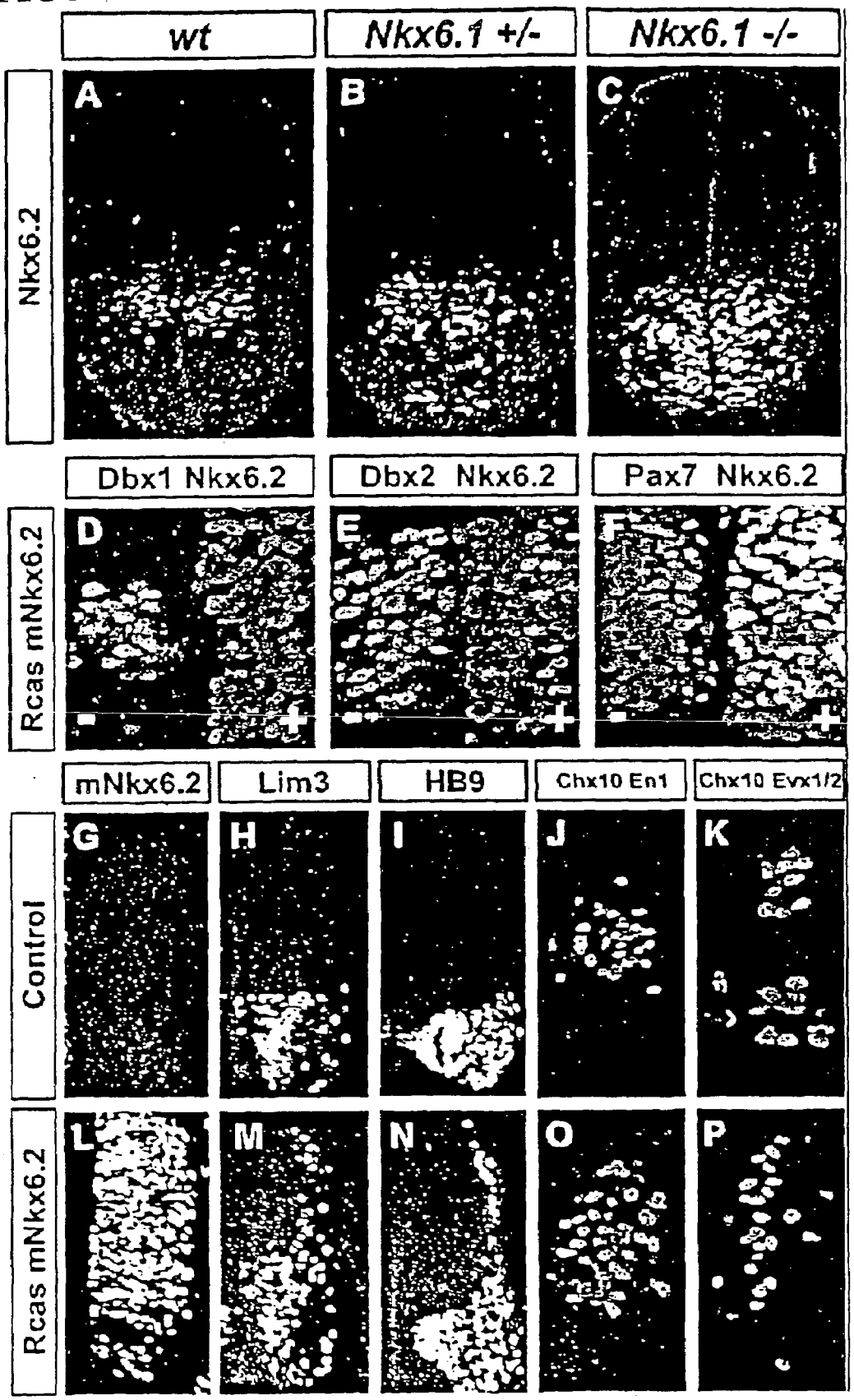
FIG. 13 deregulated expression of Nkx6.2 in Nkx6.1 mutant mice, and similar patterning activities of Nkx6 proteins in chick neural tube. (A) In e10.5 wt embryos, Nkx6.2 expression is confined to the p1 progenitor domain. (B) In Nkx6.1$^{+/-}$ embryos, scattered Nkx6.2$^+$ cells are detected in the p2, pMN and p3 domains. (C) In Nkx6.1$^{-/-}$ embryos, Nkx6.2 is expressed in most progenitors in the p2, pMN and p3 domains. (D-F) Misexpression of Nkx6.2 at high levels represses the expression of Dbx1 (D) and Dbx2 (E), but not Pax7 (F). (G-P) Expression of Nkx6.2 in dorsal positions of the chick neural tube result in ectopic dorsal generation of motor neurons, as indicated by ectopic induction of Lim3 and HB9 expression (G-I, L-N). Forced expression of Nkx6.2 at high levels in the p0 and p1 progenitor domains promotes the ectopic generation of Chx10$^+$ V2 neurons (J, K, O, P) and suppresses Evx1/2$^+$ V0 (K, P) and En1$^+$ V1 (J, O) neurons.

In support of this idea, in Nkx6.1$^{+/-}$ embryos examined at e10.5 we detected a marked increase in the number of Nkx6.2$^+$ cells within the p2 and pMN domains (FIG. 13B). And in Nkx6.1$^{-/-}$ embryos, expression of Nkx6.2 was detected in virtually all progenitor cells within the p2 and pMN domains (FIG. 13C). Indeed, in Nkx6.1$^{-/-}$ embryos, the level of Nkx6.2 expression in the nuclei of progenitor cells within the p2 and pMN domains was 1.9-fold greater than that in progenitor cells located within the p1 domain (FIG. 13C; data not shown). Together, these data show that Nkx6.1 activity normally represses Nkx6.2 expression from p2 and pMN progenitors in the mouse embryo.

In turn, these findings raised the possibility that in Nkx6.1$^{-/-}$ embryos, the derepression of Nkx6.2 expression substitutes for the loss of Nkx6.1 during motor neuron generation. If this is the case, Nkx6.2 would be predicted to mimic the ability of Nkx6.1 to induce motor neurons in vivo. Expression of chick or mouse Nkx6.2 in the neural tube of HH stage 10-12 chick embryos repressed Dbx2 and Dbx1 expression (FIGS. 13D-F), and induced ectopic motor neuron differentiation (FIGS. 13G-I, L-N) with an efficacy similar to that of Nkx6.1 (Briscoe et al., 2000). These data show that Nkx6.2 can induce ectopic motor neurons when expressed at high levels in the dorsal neural tube, supporting the idea that both Nkx6 proteins can exert similar patterning activities in vivo (FIGS. 13D-O; Briscoe et al., 2000). In addition, misexpression of Nkx6.2 in the p0 and p1 progenitor domains suppressed the generation of Evx1/2$^+$ V0 and En1$^+$ V1 neurons and promoted the generation of Chx10$^+$ V2 neurons (FIG. 13J, K, O, P). Thus, a high level of expression of Nkx6.2 is not compatible with the generation of either V0 or V1 neurons (FIG. 13O, P).

Based on these findings, we examined whether Nkx6.2 has a role in motor neuron generation in Nkx6.1 mutant mice by testing the impact of removing Nkx6.2 as well as Nkx6.1 on the generation of spinal motor neurons. In Nkx6.2$^{tlz/tlz}$ embryos there was no change in the number of motor neurons generated at any level of the spinal cord or hindbrain (FIG. 14G,N,O; data not shown). In Nkx6.1$^{-/-}$ mutants, the number of spinal motor neurons was reduced by ~60% at cervical levels, but by only 25% at lumbar levels (FIG. 14H,N,O, Sander et al., 2000). In Nkx6.1$^{-/-}$; Nkx6.2$^{+/tlz}$ embryos, motor neuron generation was reduced to ~25% of controls at both cervical and lumbar levels (FIG. 14I,N,O; data not shown). In Nkx6.1$^{-/-}$; Nkx6.2$^{tlz/tlz}$ embryos, the generation of motor neurons was reduced to <10% of wild type numbers, at all levels of the spinal cord (FIG. 14J). In these Nkx6 double mutant embryos, residual motor neurons were detected at e10.0, and no further increase in motor neuron number was evident at e12 (FIG. 14M, P; data not shown). Since there was no increase in apopototic cell death in the ventral neural tube over this period (data not shown), we infer that the few spinal motor neurons present in Nkx6 double mutants are generated prior to e10. Together, these findings demonstrate that Nkx6.2 substitutes for the loss of Nkx6.1 in spinal motor neuron generation, and reveal a link between Nkx6 gene dosage and the incidence of motor neuron generation.

A Dissociation in Neuronal Pate and Progenitor Cell Identity in Nkx6 Mutant Mice We next examined whether a reduction in Nkx6 gene dosage results in ectopic Dbx protein expression and V1 and V0 neuron generation in the p2 and pMN domains of the ventral spinal cord.

En1$^+$ V1 neurons are normally generated from Dbx2$^+$, Dbx1$^-$ p1 progenitor cells, and we therefore analysed the relationship between Dbx2 expression and En1l$^+$ V1 neuronal generation in Nkx6.1 and Nkx6.2 compound mutants. As reported previously (Sander et al., 2000), in Nkx6.1$^{-/-}$ embryos examined at e10.5, ectopic ventral expression of Dbx2 was detected at high levels in the p2 and p3 domains, although cells in the pMN expressed only very low levels of Dbx2 (FIG. 15H; see Sander et al., 2000). Moreover, in Nkx6.1$^{-/-}$ embryos, ectopic En1$^+$ neurons were generated in the p2 and pMN domains of the ventral neural tube (FIG. 15R). In Nkx6.1$^{-/-}$; Nkx6.2$^{+/tlz}$ embryos, Dbx2 expression was detected at intermediate levels in the pMN domain (FIG. 15I), and in Nkx6.1$^{-/-}$; Nkx6.2$^{tlz/tzl}$ double mutant embryos, Dbx2 was detected at uniformly high levels in the p2 and pMN domains (FIG. 15J). Strikingly, in these Nkx6.1 and Nkx6.2 compound mutant backgrounds, and despite the enhanced ectopic expression of Dbx2, the number of ectopic ventral En1$^+$ V1 neurons was reduced rather than increased, when compared with the number generated in Nkx6.1 single mutants (FIG. 15R, T).

Since Evx1$^+$ V0 neurons are normally generated from Dbx1$^+$, Dbx2$^+$ p0 progenitors, we examined whether the reduction in ectopic ventral En1$^+$ V1 neuron generation at low Nkx6 gene dosage might reflect a change in the pattern of expression of Dbx1, and the ectopic generation of V0 neurons. Consistent with this idea, in Nkx6.1$^{-/-}$; Nkx6.2$^{tlz/tlz}$ mutants, scattered Dbx$^+$ cells were detected in the p2, pMN and p3 domains (FIG. 15O), and ectopic ventral Evx1/2$^+$ V0 neurons were detected throughout the ventral neural tube (FIG. 15T, Z). Thus, in Nkx6 double mutants, the loss of V1 neurons is associated with the ectopic ventral expression of Dbx1 and the generation of ectopic V0 neurons.

But in Nkx6.1 single and Nkx6.1$^{-/-}$; Nkx6.2$^{+/tlz}$ compound mutant backgrounds, the normal link between expression of Dbx1 in progenitor cells and the generation of Evx1/2$^+$ V0 neurons was severed. In both these Nkx6 compound mutants backgrounds, the domain of expression of Dbx1 was unchanged (FIG. 15M, N): a result that can be accounted for by the maintained expression of Nkx6.2 within the p1 domain, and the deregulated expression of Nkx6.2 within the p2 and pMN domains. Nevertheless, Evx1/2$^+$ V0 neurons were generated from progenitor cells in the position of p2 and pMN domains, (FIG. 15R, S, X, Y).

We next considered whether these ectopic V0 neurons were generated from the position of the p2 and pMN domains, or whether they simply migrated ventrally from a more dorsal position of origin. Ectopic ventral Evx1/2$^+$ V0 neurons were detected as early as e10.0 (FIG. 16B), and many of them coexpressed LacZ (FIG. 16C, D), providing evidence that many of these neurons derive from progenitor cells within the position of the p2 and pMN domains. The finding that Evx1/2$^+$ V0 neurons are generated from the pMN domain in Nkx6.1$^{-/-}$; Nkx6.2$^{+/tlz}$ embryos is especially significant, since these progenitors express negligible levels of Dbx2 (FIG. 16E, 17), arguing against the possibility that Dbx2 expression compensates for the absence of Dbx1 during ectopic V0 neuronal generation. These results therefore provide evidence that even though Dbx1 activity is normally required for the generation of V0 neurons (Pierani et al., 2001), under conditions in which Nkx6 gene dosage is markedly reduced, V0 neurons can be generated from progenitor cells that lack Dbx1 expression.

Figure 16:
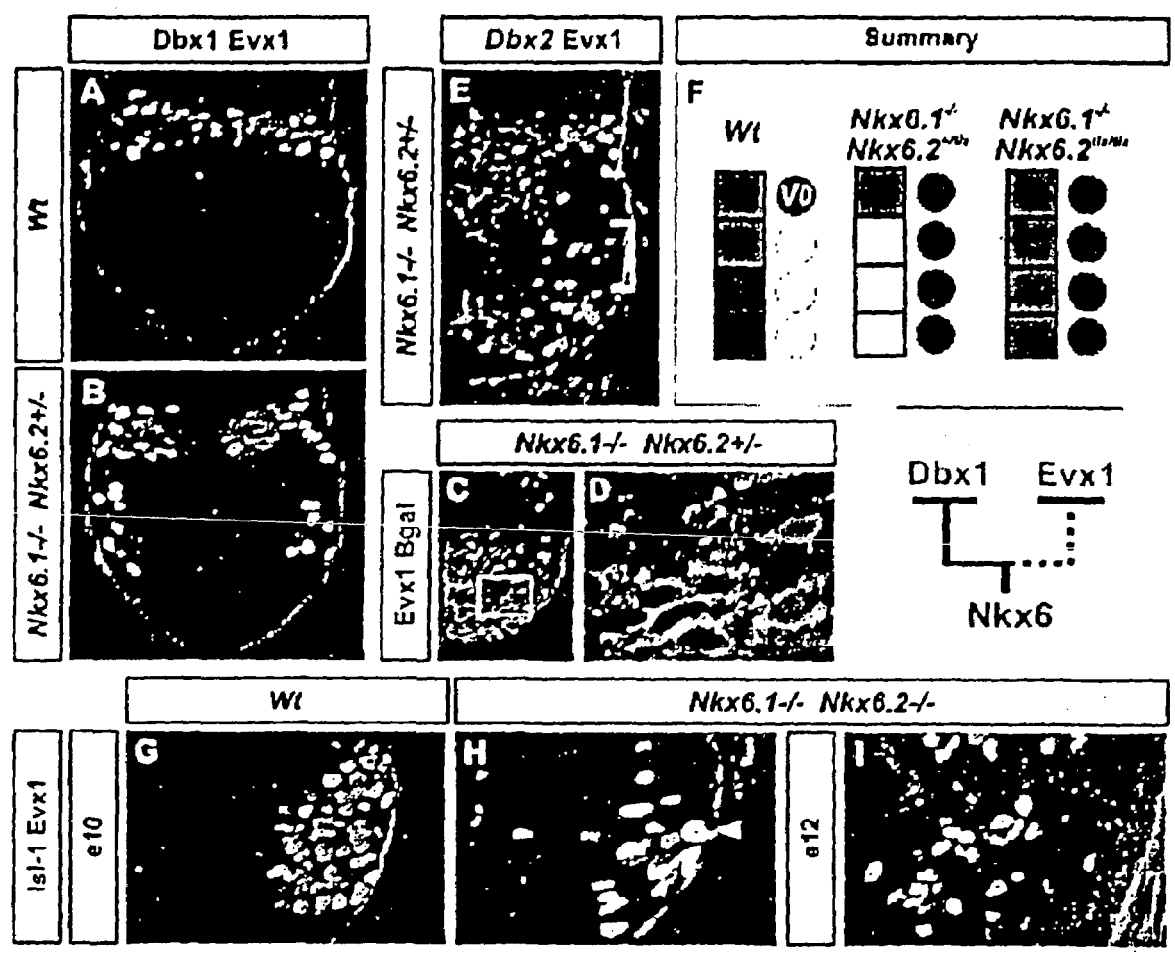
FIG. 16 dissociation of Dbx expression and V0 neuronal fate in mice with reduced Nkx6 protein activity. (A) In e10.0 wt embryos, p0 progenitor cells express Dbx1 and generate Evx1/2$^+$ V0 neurons. (B) In e10.0 Nkx6.1$^{-/-}$; Nkx6.2$^{+/tlz}$ embryos there is no change in the domain of expression of Dbx1, but Evx1/2$^+$ V0 neurons are generated in lateral positions, along much of the ventral neural tube. (C, D) In Nkx6.1$^{-/-}$; Nkx6.2$^{+/tlz}$ embryos examined at e10.0 many ectopic ventral Evx1/2$^+$ neurons express LacZ. Framed area in (C) is shown at high magnification in (D) and indicates Evx1/2$^+$ neurons that coexpress LacZ. (E) Evx1/2$^+$ neurons located at the level of the pMN domain (bracket) derive from progenitors that express low or negligible levels of Dbx2 mRNA. (F) Summary of Dbx1 expression and V0 neuron generation in wt, Nkx6.1$^{-/-}$; Nkx6.2 $^{+/tlz}$ and Nkx6.1; Nkx6.2$^{tlz/tlz}$ embryos. The dissociation of Dbx1 and Evx1/2 expression in Nkx6.1$^{-/-}$; Nkx6.2$^{+/tlz}$ embryo suggests that reduced Nkx6 repressor activity is sufficient to repress Dbx1 but insufficient to repress Evx1 expression.

Nevertheless, the pattern of ventral neurogenesis observed in Nkx6.1$^{-/-}$; Nkx6.2$^{+/tlz}$ mutants indicated that residual Isl1/2$^+$, HB9$^+$ neurons and ectopic Evx1$^+$ neurons were each generated from progenitors located in the position of the pMN domain. This observation raised the question of whether these two neuronal populations are, in fact, distinct. Strikingly, we found that in this compound Nkx6 mutant background, many of the residual Isl1/2$^+$, HB9$^+$ neurons transiently expressed Evx1 (FIG. 16H, I). Thus, under conditions of reduced Nkx6 gene dosage, progenitor cells at the position of the pMN domain initially generate neurons with a hybrid motor neuron/V0 neuron identity.

c. Discussion

The patterning of cell types in the ventral neural tube depends on the actions of a set of homeodomain proteins expressed by neural progenitor cells. Duplication of many of these genes has resulted in the overlapping neural expression of pairs of closely-related homeodomain proteins, and raises the question of whether these proteins have distinct or redundant roles during ventral neurogenesis. We have used genetic approaches in mouse to examine the respective contributions of one such homeodomain protein pair, Nkx6.1 and Nkx6.2, in ventral neural patterning. Our results imply that the duplication of an ancestral Nkx6 gene confers both redundant and distinct roles for Nkx6.1 and Nkx6.2 in ventral neuronal patterning. We discuss below how the specificity and efficacy of Nkx6-mediated transcriptional repression underlies the overlapping divergent patterning activities of the two proteins.

Redundant Activities of Nkx6 Proteins in Motor Neuron and V0 Neuron Generation

Our genetic studies in mice indicate that Nkx6.1 and Nkx6.2 have qualitatively similar activities in promoting the generation of motor neurons and in suppressing the generation of V0 neurons. How are these overlapping patterning activities achieved, given the distinct profiles of expression of these two genes?

Nkx6.1 has been shown to have a role in motor neuron generation (Sander et al., 2000), but the finding that large numbers of motor neurons are generated at caudal levels of the spinal cord in Nkx6.1 mutant mice, points to the existence of an Nkx6.1-independent pathway of motor neuron generation. At face value, Nkx6.2 would appear a poor candidate as a mediator of the Nkx6.1-independent pathway of motor neuron specification, since it is not expressed by motor neuron progenitors, nor is motor neuron generation impaired in Nkx6.2 mutant mice. Nevertheless, the activity of Nkx6.2 is responsible for the efficient generation of spinal motor neurons in Nkx6.1 mutants. The basis of this redundant function resides in the derepression of Nkx6.2 expression in motor neuron progenitors in Nkx6.1 mutant mice. Strikingly, Nkx6.2 is even derepressed in Nkx6.1$^{+/-}$ embryos, whereas there is no change in the patterns of expression of Dbx2 and other homeodomain proteins implicated in the repression of motor neuron generation. The propensity for Nkx6.2 derepression thus appears to establish a "fail-safe" mechanism that ensures that the net level of Nkx6 protein activity is maintained in motor neuron progenitors under conditions in which Nkx6.1 levels decrease.

A similar "fail-safe" regulatory mechanism may operate with other Nkx protein pairs. During pharyngeal pouch development, for example, the loss of Nkx2.6 expression appears to be compensated for by the up-regulation of Nkx2.5 (Tanaka et al., 2000).

The finding that Nkx6.2 is derepressed in the absence of Nkx6.1 function also offers a potential explanation for the divergent patterns of expression of Nkx6.2 in the ventral neural tube of mouse and chick embryos. We infer that the chick Nkx6.2 gene is not subject to repression by Nkx6.1, permitting its persistent expression in p3, pMN and p2 domain progenitor cells. Thus, in chick, the overlapping functions of Nkx6.1 and Nkx6.2 in motor neuron generation are associated with the coexpression of both genes by motor neuron progenitors, whereas in the mouse, Nkx6.2 activity is held in reserve, through its repression by Nkx6.1.

Nkx6.1 and Nkx6.2 also have an equivalent inhibitory influence on the generation of V0 neurons, albeit through activities exerted in different progenitor domains. In p1 progenitors, the repression of p0 identity and V0 neuron fate is accomplished by Nkx6.2. But ventral to the p1/p2 domain boundary it is Nkx6.1 that prevents Dbx1 expression and V0 neuronal generation. Thus, Nkx6.1 is a potent repressor of Dbx1 expression, despite the fact that these two proteins lack a common progenitor domain boundary. The repression of genes that are normally positioned in spatially distinct domains has been observed with other class I and II proteins (Sander et al., 2000). This feature of neural patterning also parallels the activities of gap proteins in anteroposterior patterning of the Drosophila embryo, where the repressive activities of individual gap proteins are frequently exerted on target genes with which they lack a common boundary (Kraut and Levine, 1991; Stanojevic et al., 1991).

Distinct Functions of Nkx6.1 and Nkx6.2 in Ventral Interneuron Generation

We now turn to the question of how Nkx6.1 and Nkx6.2 can exert distinct roles in interneuron generation, given the similarities of the two proteins in DNA target site specificity (Jorgensen et al., 1999; Muhr et al., 2001), and their overlapping functions in the patterning of motor neurons and V0 neurons.

One factor that contributes to the opponent influence of Nkx6.1 and Nkx6.2 on the specification of V1 interneuron fate is a distinction in the dorsal limit of expression of the two proteins in the neural tube, presumably a reflection of differences in the regulation of expression the two proteins by graded Shh signalling. Nkx6.1 expression stops at the p1/p2 domain boundary. And within the p2 domain, Nkx6.1 suppresses p1 progenitor identity through repression of Dbx2 and Nkx6.2 expression, in this way ensuring the generation of Chx10$^+$ V2 neurons. Nkx6.2, in contrast, occupies the p1 domain, where it is coexpressed with Dbx2. In p1 domain cells, Nkx6.2 promotes the generation of En$^+$ V1 neurons by repressing the expression of Dbx1 and Evx1, determinants of V0 neuronal fate (Pierani et al., 2001; Moran-Rivard et al., 2001). Nevertheless, only a fraction of p1 progenitors initiate Dbx1 expression and acquire V0 neuron fate in the absence of Nkx6.2 function, raising the possibility that Dbx2 may also have a role in repressing Dbx1 expression within p1 progenitors (see Pierani et al., 1999).

The second major factor that underlies the opponent activities of Nkx6.1 and Nkx6.2 in V1 interneuron specification appears to be a difference in the potency with which the two Nkx6 proteins repress a common set of target genes.

This view is supported by several observations. Nkx6.1 completely represses Nkx6.2, whereas Nkx6.2 exerts an incomplete negative regulation of its own expression in p1 domain progenitors. Thus, Nkx6.1 is evidently a better repressor of Nkx6.2 than is Nkx6.2 itself. Similarly, Nkx6.2 is coexpressed with Dbx2 in p1 domain progenitors, whereas Nkx6.1 excludes Dbx2 from p2 domain progenitors, indicating that Nkx6.1 also is a more effective repressor of Dbx2 expression than is Nkx6.2. Consistent with this view, Nkx6.2 fails to repress Dbx2 expression completely from ventral progenitors in Nkx6.1 mutants. The fact that Nkx6.2 is only a weak repressor of Dbx2 is critical for the formation of the p1 domain, since the maintained expression of Dbx2 in these cells ensures the exclusion of Nkx6.1 expression (Briscoe et al., 2000).

Our results do not resolve why Nkx6.2 is a weaker repressor is than Nkx6.1 in vivo. Differences in the primary structure of Nkx6.2 and Nkx6.1 (Cai et al., 1999; Muhr et al., 2001) could result in an intrinsically lower repressor activity of Nkx6.2, when compared with that of Nkx6.1. But our findings are also consistent with the possibility that the two Nkx6 proteins have inherently similar repressor activities, and that the Nkx6.2 protein is merely expressed at a lower level. Indeed within p1 progenitors, the level of Nkx6.2 expression is clearly subject to tight regulation, with significant consequences for neuronal specification. The selective expression of Nkx6.2 in p1 progenitors, coupled with its weak negative autoregulatory activity, ensures a level of Nkx6 activity that is low enough to permit Dbx2 expression but is still sufficient to repress Dbx1 expression, thus promoting the generation of V1 neurons.

Figure 17:
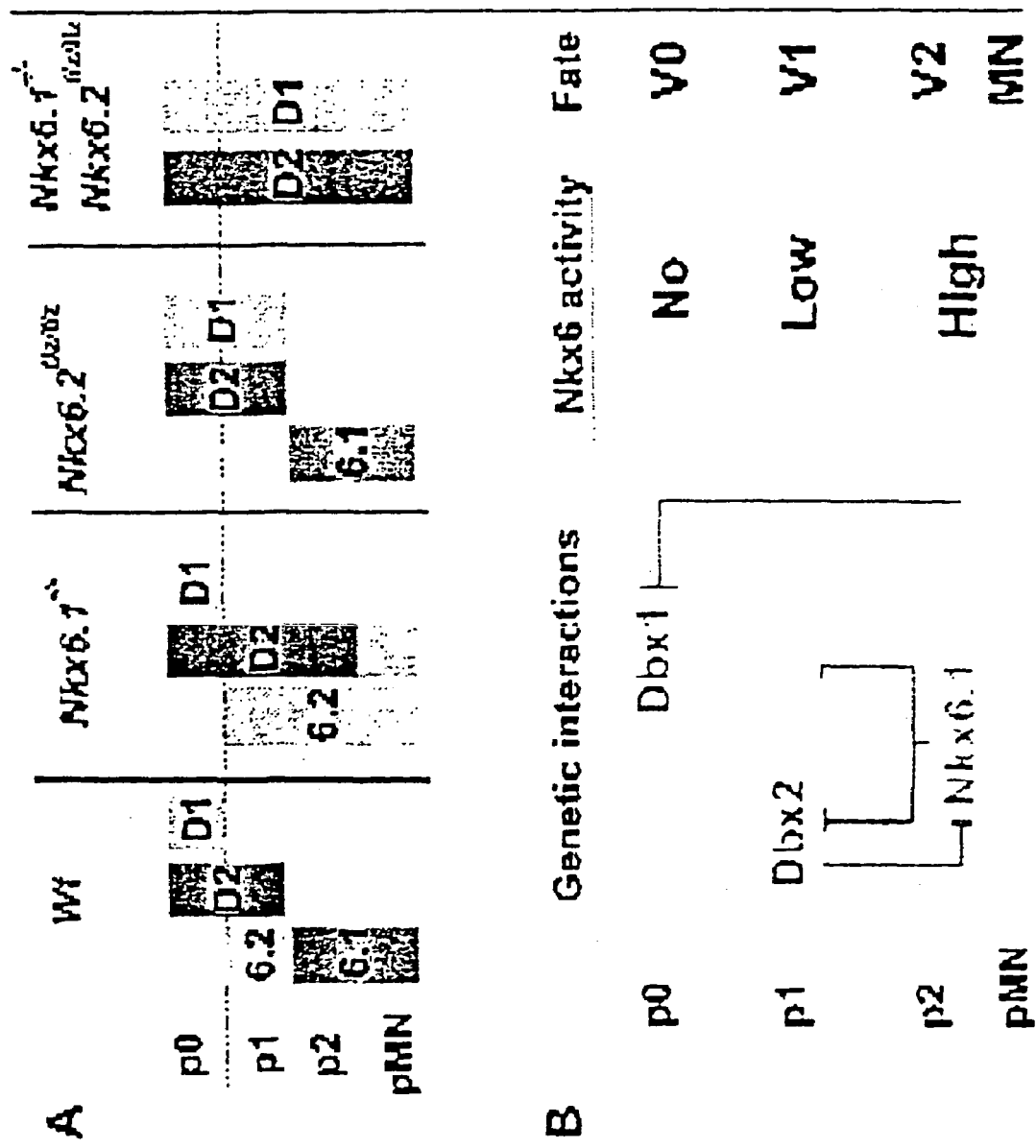
FIG. 17 genetic interactions between Nkx6 and Dbx proteins during the assignment of motor neuron and interneuron fate in the mouse neural tube. (A) Summary of domains of expression of Nkx6.1 (6.1), Nkx6.2 (6.2), Dbx1 (D1) and Dbx2 (D2) in the ventral neural tube of wild type (wt) and different Nkx6 mutant embryos. (B) Regulatory interactions between Nkx and Dbx proteins in the ventral neural tube. These interactions result in different levels of Nkx6 protein activity in distinct ventral progenitor domains, and thus promote the generation of distinct neuronal subtypes. For details see text.

Our findings therefore reveal that a gradient of extracellular Shh signalling is translated intracellularly into stepwise differences in the level of Nkx6 activity along the ventral-to-dorsal axis of the neural tube. Moreover, the different Nkx6 protein activity levels within ventral progenitor cells are a critical determinant of ventral neuronal fate. Cells that express low or negligible levels of Nkx6 activity (p0 progenitors) are directed to a V0 neuronal fate, cells that express an intermediate Nkx6 activity level (p1 progenitors) are directed to a V1 fate, and cells that express a high Nkx6 activity level (pMN and p2 progenitors) are directed to a motor neuron or V2 fate (FIG. 17).

Nkx6 Repressor Function and Neuronal Patterning by Derepression

The finding that many progenitor homeodomain proteins exert mutual-cross repressive interactions has led to a model of spinal neuronal patterning based on transcriptional derepression (Muhr et al., 2001). Similar cross-repressive interactions may establish regional progenitor domains in more rostral regions of the developing CNS (Toresson et al., 2000; Yun et al., 2001). A premise of this model is that transcriptional repression is exerted at two sequential steps in neurogenesis. One repressive step operates at the level of the progenitor homeodomain protein themselves, but a second repressive step is exerted on neuronal subtype determinant factors that have a downstream role in directing neuronal subtype fates (Briscoe et al., 2000; Muhr et al., 2001).

Our analysis of Nkx6 compound mutant mice provides direct support for this two-step repression model, and in addition indicates that progenitor homeodomain proteins and neuronal subtype determinants differ in their sensitivity to repression by the same class II protein. Normally, the functions of Dbx1 and Evx1 are required sequentially during the generation of V0 neurons (Pierani et al., 2001; Moran-Rivard et al., 2001). In Nkx6.1$^{-/-}$; Nkx6.2$^{+/tlz}$ mutants, however, the generation of Evx1/2$^+$ V0 neurons occurs in the absence of expression of Dbx1 by neural progenitor cells. Dbx1 expression is therefore dispensable for V0 neuron generation under conditions of reduced Nkx6 gene dosage. From these results, we infer that the net level of Nkx6 protein activity in ventral progenitor cells is still above threshold for repression of Dbx1 expression, but is below the level required for repression of Evx1 expression. These data therefore support the idea that Nkx6 proteins normally inhibit V0 neuronal fate by repressing the class I progenitor homeodomain protein Dbx1, and independently by repressing expression of the V0 neuronal subtype determinant Evx1.

A differential sensitivity of progenitor homeodomain proteins and neural subtype determinants to repression appears therefore to underlie the dissociation of progenitor cell identity and neuronal fate observed in Nkx6 mutants. Such two-tiered repression is, in principle, necessary to specify neuronal fate through transcriptional derepression. In the case of Nkx6.1, for example, repression of Dbx1 and Dbx2 (and possible other unidentified repressors) should be sufficient to derepress motor neuron subtype determinants such as MNR2 and Lim3 in pMN progenitors. But, unless Nkx6.1 also represses the expression of V0 determinants, Evx1 expression would also be initiated in differentiating motor neurons, resulting in a hybrid neuronal phenotype. Indeed, under conditions in which Nkx6 gene dosage is reduced or eliminated, some of the neurons generated from the position of the pMN domain do transiently express a hybrid motor neuron/V0 neuron phenotype.

The derepression model also invokes the idea that a major role of Nkx6 class proteins is to exclude the expression of Dbx2 and other proteins that inhibit motor neuron generation. This view offers a potential explanation of why a few residual motor neurons are generated in Nkx6 double mutants. We find that in the absence of Nkx6 gene function, residual motor neurons are generated only at early developmental stages, suggesting that progenitor cells within the position of the pMN domain have committed to a motor neuron fate prior to the onset of the deregulated ventral expression of Dbx2 and other motor neuron repressors. We note that a third Nkx6-like gene exists in the mouse, but this gene is not expressed in the spinal cord of wild type or Nkx6 mutant embryos (E. Anderson and J. Ericson, unpublished data), and thus its activity appears not to account for the residual motor neurons generated in Nkx6 double mutants. Importantly, the detection of residual motor neurons in Nkx6 double mutants also provides evidence that Nkx6 proteins do not have essential functions as transcriptional activators during motor neuron specification, further supporting their critical role as repressors.

Finally, the present studies and earlier work on neurogenesis in the ventral spinal cord (Ericson et al., 1996; Thaler et al., 1999; Arber et al., 1999; Sander et al., 2000) have provided evidence that newly-generated neurons can sometimes express mixed molecular identities. These observations raise the possibility that repressive interactions that select or consolidate individual neuronal identities are not restricted to progenitor cells. Consistent with this view, Evx1 is required to establish V0 and repress V1 neuronal identity through an action in post-mitotic neurons (Moran-Rivard et al., 2001), although it remains unclear whether Evx1 itself functions in this context as an activator or repressor. Similarly, the homeodomain protein HB9 has been implicated in the consolidation of motor neuron identity, through repression of V2 neuronal subtype genes (Arber et al., 1999; Thaler et al., 1999). HB9 possesses an eh-1 Gro/TLE recruitment domain (Muhr et al., 2001), suggesting that HB9 controls the identity of post-mitotic motor neurons through a direct action as a transcriptional repressor. The consolidation of neuronal subtype identity in the spinal cord may therefore depend on transcriptional repressive interactions within both progenitor cells and post-mitotic neurons.

REFERENCES

Arber, S., Han, B., Mendelsohn, M., Smith, M., Jessell, T. M., and Sockanathan, S. (1999). Requirement for the homeobox gene Hb9 in the consolidation of motor neuron identity. Neuron 23, 659-674.

Basler, K., Edlund, T., Jessell, T. M., and Yamada, T. (1993). Control of cell pattern in the neural tube: Regulation of cell differentiation by dorsalin-1, a novel TGF beta family member. Cell 73, 687-702.

Briscoe, J., Sussel, L., Serup, P., Hartigan-O'Connor, D., Jessell, T. M., Rubenstein, J. L., and Ericson, J. (1999). Homeobox gene Nkx2.2 and specification of neuronal identity by graded Sonic hedgehog signalling. Nature 398, 622-622.

Briscoe, J., Pierani, A., Jessell, T. M., and Ericson, J. (2000). A homeodomain code specifies progenitor cell identity and neuronal fate in the ventral neural tube. Cell 101, 435-445.

Briscoe, J., and Ericson, J. (2001). Specification of neuronal fates in the ventral neural tube. Curr Opin Neurobiol. 1, 43-49.

Briscoe, J., Chen, Y., Jessell, T. M. and Struhl, G. (2001). A hedgehog-insensitive form of patched provides evidence for direct long-range patterning activity of Sonic hedgehog in the neural tube. Molecular Cell, In Press.

Burrill, J. D., Moran, L., Goulding, M. D. and Saueressig, H. (1997). Pax2 is expressed in multiple spinal cord interneurons, including a population of EN1+ interneurons that require Pax6 for their development. Development 124, 4493-4503.

Cai, J., St Amand, T., Yin, H., Guo, H., Li, G., Zhang, Y., Chen, Y., and Qiu, M. (1999). Expression and regulation of the chicken Nkx-6.2 homeobox gene suggest its possible involvement in the ventral neural patterning and cell fate specification. *Dev Dyn* 216, 459-468.

Davis, C. A., Holmyard, D. P., Millen, K. J., and Joyner, A. L. (1991) Examining pattern formation in mouse, chicken and frog embryos with an En-specific antiserum. Development 111, 287-298.

Eberhard, D., Jimenez, G., Heavey, B. and Busslinger, M. (2000). Transcriptional repression by Pax5 (BSAP) through interaction with corepressors of the Groucho family. *EMBO J.* 19, 2292-2303.

Ericson, J., Morton, S., Kawakami, A., Roelink, H., and Jessell, T. M. (1996). Two critical periods of Sonic Hedgehog signaling required for the specification of motor neuron identity. Cell 87, 661-673.

Ericson, J., Rashbass, P., Schedl, A., Brenner-Morton, S., Kawakami, A., van Heyningen, V., Jessell, T. M., and Briscoe, J. (1997). Pax6 controls progenitor cell identity and neuronal fate in response to graded Shh signaling. Cell 90, 169-180.

Hamburger, H. and Hamilton, H. L. (1953). A series of normal stages in the development of the chick embryo. J. Morphol. 88, 49-92.

Hoshiyama, D., Suga, H., Iwabe, N., Koyanagi, M., Nikoh, N., Kuma, K., Matsuda, F., Honjo, T., and Miyata, T. (1998). Sponge Pax cDNA related to Pax-2/5/8 and ancient gene duplications in the Pax family. J. Mol. Evol. 47, 640-648.

Jörgensen, M. C., Vestergard Petersen, H., Ericson, J., Madsen, O. D., Serup, P. (1999). Cloning and DNA-binding properties of the rat pancreatic beta-cell-specific factor Nkx6.1. FEBS Lett. 461, 287-294.

Kraut, R. and Levine, M. (1991). Mutually repressive interactions between the gap genes giant and Kruppel define middle body regions of the Drosophila embryo. 111, 611-621.

Komuro, I., Schalling, M., Jahn, L., Bodmer, R., Jenkins, N. A., Copeland, N. G., Izumo, S. (1993). Gtx: a novel murine homeobox-containing gene, expressed specifically in glial cells of the brain and germ cells of testis, has a transcriptional repressor activity in vitro for a serum-inducible promoter. EMBO 12, 1387-1401.

Lee, S., Davison, J. A., Vidal, S. M., Belouchi, A. (2001). Cloning, expression and chromosomal location of NKX6B to 10q26, a region frequently deleted in brain tumors. Mammalian Genome 12, 157-162.

Mansouri, A., and Gruss, P. (1998). Pax3 and Pax7 are expressed in commissural neurons and restrict ventral neuronal identity in the spinal cord. Mech Dev 78, 171-178.

Moran-Rivard, L., Kagawa, T., Saueressig, H., Gross, M., Burrill, J., Goulding, M. (2001). Evx1 is a postmitotic determinant of V0 interneuron identity in the spinal cord. Neuron 29, 385-399.

Mombaerts, P., Wang, F., Dulac, C., Chao, S. K., Nemes, A., Mendelsohn, M., Edmondson. J., Axel, R. (1996). Visualizing an olfactory sensory map. Cell 87, 675-686.

Muhr, J. Andersson, E., Persson, M., Jessell, T M. Ericson, J. (2001). Groucho-mediated transcriptional repression establishes progenitor cell pattern and neuronal fate in the ventral neural tube. Cell 104, 861-873.

Novitch, B., Chen, A. I. and Jessell, T. M. (2001). Coordinate regulation of motor neuron subtype identity and pan-neural properties by the bHLH repressor Olig2. Submitted Nutt, S. L., Heavey, B., Rolink, A. G., and Busslinger, M. (1999). Commitment to the B-lymphoid lineage depends on the transcription factor Pax5. *Nature* 401, 556-562.

Pabst, O., Herbrand, H., Takuma, N., and Arnold, H. H. (2000). NKX2 gene expression in neuroectoderm but not in mesendodermally derived structures depends on sonic hedgehog in mouse embryos. *Dev Genes Evol* 210, 47-50.

Peters, T., Dildrop, R., Ausmeier, K., and Ruther U. (2001). Organization of mouse Iroquois homeobox genes in two clusters suggests a conserved regulation and function in vertebrate development. Genome Res. 10, 1453-62.

Pierani, A., Brenner-Morton, S., Chiang, C., and Jessell, T. M. (1999). A sonic hedgehog-independent, retinoid-activated pathway of neurogenesis in the ventral spinal cord. Cell 97, 903-915.

Pierani, A., Moran-Rivard, L., Sunshine, M. J., Littman, D. R., Goulding, M., and Jessell, T. M. (2001). Control of interneuron fate in the developing spinal cord by the progenitor homeodomain protein Dbx1. Neuron 29, 367-384.

Qiu, M., Shimamura, K., Sussel, L., Chen, S., and Rubenstein, J. L. (1998). Control of anteroposterior and dorsoventral domains of Nkx-6.1 gene expression relative to other Nkx genes during vertebrate CNS development. Mech Dev 72, 77-88.

Rolink, A. G., Nutt, S. L., Melchers, F., and Busslinger, M. (1999). Long-term in vivo reconstitution of T-cell development by Pax5-deficient B-cell progenitors. *Nature* 401, 603-606.

Sander, M., Paydar, S., Ericson, J., Briscoe, J., Berber, E., German, M., Jessell T. M., and Rubenstein J. L. (2000). Ventral neural patterning by Nkx homeobox genes: Nkx6.1 controls somatic motor neuron and ventral interneuron fates. Genes Dev. 17, 2134-2139.

Schaeren-Wiemers, N. and Gerfin-Moser, A. (1993). A single protocol to detect transcripts of various types and expression levels in neural tissue and cultured cells: in situ hybridization using digoxigenin-labeld cRNA probes. Histochemistry 100, 431-440.

Shoji H, Ito T, Wakamatsu Y, Hayasaka N, Ohsaki K, Oyanagi M, Kominami R, Kondoh H, Takahashi N. (1996) Regionalized expression of the Dbx family homeobox genes in the embryonic CNS of the mouse. Mech. Dev. 56, 25-39

Stanojevic, D., Small, S. and Levine, M. (1991). Regulation of a segmentation stripe by overlapping activators and repressors in the Drosophila embryo. Science 254, 1385-1387.

Tanabe, Y., William, C., and Jessell, T. M. (1998). Specification of motor neuron identity by the MNR2 homeodomain protein. Cell 95, 67-80.

Tanaka, M., Yamasaki, N., Izumo, S. (2000). Phenotypic characterization of the murine Nkx2.6 homeobox gene by gene targeting. Mol Cell Biol. 8, 2874-2879.

Thaler, J., Harrison, K., Sharma, K., Lettieri, K., Kehrl, J., and Pfaff S. L. (1999). Active suppression of interneuron programs within developing motor neurons revealed by analysis of homeodomain factor HB9. *Neuron* 23, 675-687.

Toresson, H., Potter, S. S. and Campbell, K. (2000). Genetic control of dorsal-ventral identity in the telencephalon: opposing roles for Pax6 and Gsh2. Development. 127, 4361-4371.

Tsuchida, T., Ensini, M., Morton, S. B., Baldassare, M., Edlund, T., Jessell, T. M., Pfaff, S. L. (1994). Topographic organization of embryonic motor neurons defined by expression of LIM homeobox genes. Cell 79, 957-970.

Wang, C. C., Brodnicki, T., Copeland, N. G., Jenkins, N. A., Harvey, R. P. (2000). Conserved linkage of NK-2-1/2-9 in mammals. Mamm. Genome 11, 466-468.

Yamada, T., Pfaff, S. L., Edlund, T., and Jessell, T. M. (1993). Control of cell pattern in the neural tube: motor neuron induction by diffusible factors from notochord and floor plate. Cell 73, 673-686.

Yun, K., Potter, S. and Rubenstein, J. L. (201. Gsh2 and Pax6 play complementary roles in dorsoventral patterning of the mammalian telencephalon. Development 128, 193-205.

---

What is claimed is:

1. A method of converting a neural stem cell into a ventral neuron which comprises introducing into the neural stem cell, in vitro, a nucleic acid encoding homeodomain transcription factor Nkx6.2 protein, wherein the encoded protein is expressed in the neural stem cell so as to thereby convert the neural stem cell into the ventral neuron.

2. The method of claim 1, wherein the nucleic acid introduced into the neural stem cell incorporates into the chromosomal DNA of the neural stem cell.

3. The method of claim 1, wherein the nucleic acid is introduced by transfection or transduction.

4. The method of claim 1, wherein the ventral neuron is a motor neuron.

* * * * *